US007378247B2

(12) United States Patent
Müller-Hermelink et al.

(10) Patent No.: US 7,378,247 B2
(45) Date of Patent: May 27, 2008

(54) NEOPLASM-SPECIFIC POLYPEPTIDES AND THEIR USES

(75) Inventors: Hans Konrad Müller-Hermelink, Würzburg (DE); Heinz Peter Vollmers, Würzburg (DE); Frank Hensel, Würzburg (DE)

(73) Assignee: Debiovision Inc., Montreal (CA)

( * ) Notice: Subject to any disclaimer, the term of this patent is extended or adjusted under 35 U.S.C. 154(b) by 0 days.

(21) Appl. No.: 10/764,730

(22) Filed: Jan. 26, 2004

(65) Prior Publication Data

US 2005/0032134 A1    Feb. 10, 2005

Related U.S. Application Data

(63) Continuation-in-part of application No. PCT/DE02/02699, filed on Jul. 23, 2002.

(30) Foreign Application Priority Data

Jul. 24, 2001   (DE)   ............... 101 36 009
Mar. 9, 2002   (DE)   ............... 102 10 425

(51) Int. Cl.
*G01N 33/53* (2006.01)
(52) U.S. Cl. ............... 435/7.1; 435/7.23
(58) Field of Classification Search ............... None
See application file for complete search history.

(56) References Cited

FOREIGN PATENT DOCUMENTS

| WO | WO 00/37489 A2 | 6/2000 |
|---|---|---|
| WO | WO 00/37489 A3 | 6/2000 |
| WO | WO 03/011907 A2 | 2/2003 |
| WO | WO 03/011907 A3 | 2/2003 |
| WO | WO 03/076472 A2 | 9/2003 |
| WO | WO 2004/005351 A2 | 1/2004 |

OTHER PUBLICATIONS

Hensel et al, Cancer Research 59:5299-5306, 1999.*
Applemelk et al., "Molecular Mimicry between *Helicobacter pylori* and the Host," *Trends in Microbiology* 5(2):70-73 (1997).
Burrus et al., "Identification of Cysteine-Rich Receptor for Fibroblast Growth Factors," *Molecular and Cellular Biology* 12(12):5600-5609 (1992).
Brändlein et al., "Human Monoclonal IgM Antibodies with Apoptotic Activity Isolated from Cancer Patients," *Hum. Antibodies* 11(4):107-119 (2002).
Brändlein et al., "Natural IgM Antibodies and Immunosurveillance Mechanisms Against Epithelial Cancer Cells in Humans," *Cancer Res.* 63:7995-8005 (2003).
Brändlein et al., "Cysteine-Rich Fibroblast Growth Factor Receptor 1, a New Marker for Precancerous Epithelial Lesions Defined by the Human Monoclonal Antibody PAM-1," *Cancer Research* 63:2052-2061 (2003).
Brändlein et al., "CFR-1 Receptor as Target for Tumor-Specific Apoptosis Induced by the Natural Human Monoclonal Antibody PAM-1," *Oncology Reports* 11:777-784 (2004).

Brown and Gatter, "Ki67 Protein: the Immaculate Deception," *Histopathology* 40:2-11 (2002).
Claeys et al., "The Gastric $H^+$, $K^+$—ATPase Is a Major Autoantigen in Chronic *Helicobacter pylori* Gastritis with Body Mucosa Atrophy," *Gastroenterology* 115:340-347 (1998).
Crabtree et al., "Gastric Interleukin-8 and IgA IL-8 Autoantibodies in *Helicobacter pylori* Infection," *Scand. J. Immunol.* 37:65-70 (1993).
Endl and Gerdes, "The Ki-67 Protein: Fascinating Forms and an Unknown Function," *Experimental Cell Research* 257:231-237 (2000).
Gonatas et al., "Truncations of the C-Terminal Cytoplasmic Domain of MG160, a Medial Golgi Sialoglycoprotein, Result in its Partial Transport to the Plasma Membrane and Filopodia," *Journal of Cell Science* 111:249-260 (1998).
Hensel et al., "Mitogenic Autoantibodies in *Helicobacter pylori*-Associated Stomach Cancerogenesis," *Int. J. Cancer* 081:229-235 (1999).
Hensel et al., "A Novel Proliferation-Associated Variant of CFR-1 Defined by a Human Monoclonal Antibody," *Lab Invest.* 81(8):1097-1108 (2001).
Hensel et al., "A New Variant of Cystein-Rich FGF Receptor (CFR-1) Specifically Expressed on Tumor Cells," *Proceedings of the American Association for Cancer Research Annual* 41 pp. 698 Abstract 4438 (2000).
Ma et al., "Positive Correlation between H,K-Adenosine Triphosphatase Autoantibodies and *Helicobacter pylori* Antibodies in Patients with Pernicious Anemia," *Scand. J. Gastroenterol.* 29(11):961-965 (1994).
Mourelatos et al., "Cloning and Sequence Analysis of the Human MG160, a Fibroblast Growth Factor and E-Selectin Binding Membrane Sialoglycoprotein of the Golgi Apparatus," *DNA and Cell Biology* 15:1121-1128 (1996).
Negrini et al., "Antigenic Mimicry between *Helicobacter pylori* and Gastric Mucosa in the Pathogenesis of Body Atrophic Gastritis," *Gastroenterology* 111:655-665 (1996).
Pfaff et al., "Human Monoclonal Antibody against a Tissue Polypeptide Antigen-Related Protein from a Patient with a Signet-Ring Cell Carcinoma of the Stomach," *Cancer Research* 50:5192-5198 (1990).
Ramires et al., "Ki67 Labelling Index in Gastric Carcinomas. An Immunohistochemical Study Using Double Staining for the Evaluation of the Proliferative Activity of Diffuse-Type Carcinomas," *Journal of Pathology.* 182:62-67 (1997).
Scholzen and Gerdes, "The Ki-67 Protein: From the Known and the Unknown," *Journal of Cellular Physiology* 182:311-322 (2000).
Smalheiser "Proteins in Unexpected Locations," *Molecular Biology of the Cell* 7:1003-1014 (1996).
Steegmaier et al., "The E-Selectin-Ligand ESL-1 Is a Variant of a Receptor for Fibroblast Growth Factor," *Nature* 373:615-620 (1995).

(Continued)

*Primary Examiner*—Misook Yu
*Assistant Examiner*—Mark Halvorson
(74) *Attorney, Agent, or Firm*—Clark & Elbing LLP

(57) ABSTRACT

The present invention features novel polypeptides and methods of using these polypeptides in the diagnosis, detection, monitoring, and treatment of neoplasms in a mammal, e.g., a human.

8 Claims, 20 Drawing Sheets

OTHER PUBLICATIONS

Steegmaier et al., "The E-Selectin-Ligand ESL-1 Is Located in the Golgi as well as on Microvilli on the Cell Surface," *Journal of Cell Science* 110:687-694 (1997).

Steininger et al., "Apoptosis in Chronic Gastritis and its Correlation with Antigastric Autoantibodies," *Virchows* Arch 433:13-18 (1998).

Stieber et al., "MG160, A Membrane Protein of the Golgi Apparatus which Is Homologous to a Fibroblast Growth Factor Receptor and to a Ligand for E-Selectin, Is Found only in the Golgi Apparatus and Appears early in Chicken Embryo Development," *Experimental Cell Research* 219:562-570 (1995).

Stulle et al., "Human Stomach Carcinoma-Specific T Cells Derived from the Tumour-Draining Lymph Nodes," Br. J. Cancer 70:1053-1059 (1994).

Vollmers et al., "Monoclonal Antibodies NORM-1 and NORM-2 Induce more Normal Behavior of Tumor Cells In Vitro and Reduce Tumor Growth In Vivo," *Cell* 40:547-557 (1985).

Vollmers et al., "Human Monoclonal Antibodies from Stomach Carcinoma Patients React with *Helicobacter pylori* and Stimulate Stomach Cancer Cells in Vitro," *Cancer* 74(5):1525-1532 (1994).

Vollmers et al., "Adjuvant Therapy for Gastric Adenocarcinoma with the Apoptosis-Inducing Human Monoclonal Antibody SC-1: First Clinical and Histopathological Results," *Oncology Reports* 5:549-552 (1998).

Vollmers et al., "Nature's Best Weapons to Fight Cancer. Revival of Human Monoclonal IgM Antibodies," *Human Antibodies* 11:131-142 (2002).

Vollmers and Birchmeier, "Monoclonal Antibodies Inhibit the Adhesion of Mouse B 16 Melanoma Cells in vitro and Block Lung Metastasis in vivo," *Proc. Natl. Acad. Sci.* 80:3729-3733 (1983).

Zuber et al., "Cysteine-Rich FGF Receptor Regulates Intracellular FGF-1 and FGF-2 Levels," *Journal of Cellular Physiology* 170:217-227 (1997).

Vollmers, et al., "PAM-1, a Human Monoclonal IGM Antibody Usefull for Diagnosis and Therapy of Precancerous and Cancerous Epithelial Lesions," Human Antibodies 11:3-7 (2002) (Sep. 16, 2002 Session Abstract).

Gonatas, et al., "MG-160, a Membrane Sialoglycoprotein of the Medial Cisternae of the Rat Golgi Apparatus, Binds Basic Fibroblast Growth Factor and Exhibits a High Level of Sequence Identity to a Chicken Fibroblast Growth Factor Receptor," *Journal of Cell Science* 108:457-467 (1995).

GenBank Accession No. AAB06460.

GenBank Accession No. AAB02178.

U.S. Appl. No. 10/586,229, filed Jul. 19, 2006, Vollmers et al.

International Search Report for PCT/IB2005/002480 (Nov. 17, 2005).

* cited by examiner

```
tcc tgc aag gct tct ggc tac acc ttc act gac tac tat ata aac      45
Ser Cys Lys Ala Ser Gly Tyr Thr Phe Thr Asp Tyr Tyr Ile Asn
 1               5                  10                  15 tgg gtg aag cag agg act gga cag ggc ctt gag tgg att gga gag      90
Trp Val Lys Gln Arg Thr Gly Gln Gly Leu Glu Trp Ile Gly Glu
                20                  25                  30 att tat cct gga agt ggt aat act tac tac aat gag aag ttc aag     135
Ile Tyr Pro Gly Ser Gly Asn Thr Tyr Tyr Asn Glu Lys Phe Lys
                    35                  40                  45 ggc aag gcc aca ctg act gca gac aaa tcc tcc agc aca gcc tac     180
Gly Lys Ala Thr Leu Thr Ala Asp Lys Ser Ser Ser Thr Ala Tyr
                50                  55                  60 atg cag ctc agc agc ctg aca tct gag gac tct gca gtc tat ttc     225
Met Gln Leu Ser Ser Leu Thr Ser Glu Asp Ser Ala Val Tyr Phe
                65                  70                  75 tgt gca aga tcg gga tta cga ccc tat gct atg gac tac tgg ggt     270
Cys Ala Arg Ser Gly Leu Arg Pro Tyr Ala Met Asp Tyr Trp Gly
                80                  85                  90 caa gga acc tca gtc acc
Gln Gly Thr Ser Val Thr
                95
```

Fig. 8A

Nucleotide sequence of the variable region of the heavy chain (VH) of antibody NM58-49/69

```
                                              CDR1
tcc tgc aag gct tct ggc tac acc ttc act gac tac tat ata aac
Ser Cys Lys Ala Ser Gly Tyr Thr Phe Thr Asp Tyr Tyr Ile Asn
 1                   5                  10                 15 tgg gtg aag cag agg act gga cag ggc ctt gag tgg att gga gag   90
Trp Val Lys Gln Arg Thr Gly Gln Gly Leu Glu Trp Ile Gly Glu
         20                  25                  30
                       CDR2
att tat cct gga agt ggt aat act tac aat gag aag ttc aag     135
Ile Tyr Pro Gly Ser Gly Asn Thr Tyr Asn Glu Lys Phe Lys
             35                  40                  45 ggc aag gcc aca ctg act gca gac aaa tcc tcc agc aca gcc tac   180
Gly Lys Ala Thr Leu Thr Ala Asp Lys Ser Ser Ser Thr Ala Tyr
                 50                  55                  60 atg cag ctc agc agc ctg aca tct gag gac tct gca gtc tat ttc   225
Met Gln Leu Ser Ser Leu Thr Ser Glu Asp Ser Ala Val Tyr Phe
                     65                  70                  75
                                           CDR3
tgt gca aga tcg gga tta cga ccc tat gct atg gac tac tgg ggt   270
Cys Ala Arg Ser Gly Leu Arg Pro Tyr Ala Met Asp Tyr Trp Gly
                         80                  85                  90
        D-gene                          J-gene caa gga acc tca gtc acc
Gln Gly Thr Ser Val Thr
                         95
```

Fig. 8B

```
cca ctc tcc ctg cct gtc agt ctt gga gat caa gcc tcc atc tct    45
Pro Leu Ser Leu Pro Val Ser Leu Gly Asp Gln Ala Ser Ile Ser
 1               5                  10                  15 tgc aga tct agt cag agc att gta cat agt aat gga aac acc tat    90
Cys Arg Ser Ser Gln Ser Ile Val His Ser Asn Gly Asn Thr Tyr
                20                  25                  30 tta gaa tgg tac ctg cag aaa cca ggc cag tct cca aag ctc ctg   135
Leu Glu Trp Tyr Leu Gln Lys Pro Gly Gln Ser Pro Lys Leu Leu
                35                  40                  45 atc tac aaa gtt tcc aac cga ttt tct ggg gtc cca gac agg ttc   180
Ile Tyr Lys Val Ser Asn Arg Phe Ser Gly Val Pro Asp Arg Phe
                50                  55                  60 agt ggc agt gga tca ggg aca gat ttc aca ctc aag atc agc aga   225
Ser Gly Ser Gly Ser Gly Thr Asp Phe Thr Leu Lys Ile Ser Arg
                65                  70                  75 gtg gag gct gag gat ctg gga gtt tat tac tgc ttt caa ggt tca   270
Val Glu Ala Glu Asp Leu Gly Val Tyr Tyr Cys Phe Gln Gly Ser
                80                  85                  90 cat gtt ccg tac acg ttc gga ggg ggg acc aag ctg gaa ata aaa   315
His Val Pro Tyr Thr Phe Gly Gly Gly Thr Lys Leu Glu Ile Lys
                95                  100                 105
```

Fig. 9A

Nucleotide sequence of the variable region of the light chain (VL) of antibody NM58-49/69

```
cca ctc tcc ctg cct gtc agt ctt gga gat caa gcc tcc atc tct  45
Pro Leu Ser Leu Pro Val Ser Leu Gly Asp Gln Ala Ser Ile Ser
 1                   5                  10                 15 tgc aga tct agt cag agc att gta cat agt aat gga aac acc tat  90
Cys Arg Ser Ser Gln Ser Ile Val His Ser Asn Gly Asn Thr Tyr
                    20                  25                 30
                         —————————CDR1————————— tta gaa tgg tac ctg cag aaa cca ggc cag tct cca aag ctc ctg 135
Leu Glu Trp Tyr Leu Gln Lys Pro Gly Gln Ser Pro Lys Leu Leu
                    35                  40                 45
    ———————————————— atc tac aaa gtt tcc aac cga ttt tct ggg gtc cca gac agg ttc 180
Ile Tyr Lys Val Ser Asn Arg Phe Ser Gly Val Pro Asp Arg Phe
                    50                  55                 60
    ——————CDR2—————— agt ggc agt gga tca ggg aca gat ttc aca ctc aag atc agc aga 225
Ser Gly Ser Gly Ser Gly Thr Asp Phe Thr Leu Lys Ile Ser Arg
                    65                  70                 75 gtg gag gct gag gat ctg gga gtt tat tac tgc ttt caa ggt tca 270
Val Glu Ala Glu Asp Leu Gly Val Tyr Tyr Cys Phe Gln Gly Ser
                    80                  85                 90
                                              ——————————
                                                   CDR3 cat gtt ccg tac acg ttc gga ggg ggg acc aag ctg gaa ata aaa 315
His Val Pro Tyr Thr Phe Gly Gly Gly Thr Lys Leu Glu Ile Lys
                    95                 100                105
——————————————————
```

Fig. 9B

```
gat gtg agg gag cct gaa aat gaa att tct tca gac tgc aat cat     45
Asp Val Arg Glu Pro Glu Asn Glu Ile Ser Ser Asp Cys Asn His
            5                   10                  15 ttg ttg tgc aat tat aag ctg aac cta act aca gat ccc aaa ttt     90
Leu Leu Trp Asn Tyr Lys Leu Asn Leu Thr Thr Asp Pro Lys Phe
            20                  25                  30 gaa tct gtg gcc aga gag gtt tgc aaa tct act ata aca gag att    135
Glu Ser Val Ala Arg Glu Val Cys Lys Ser Thr Ile Thr Glu Ile
            35                  40                  45 gaa gaa tgt gct gat gaa ccg gtt gga aaa ggt tac atg gtt tcc    180
Glu Glu Cys Ala Asp Glu Pro Val Gly Lys Gly Tyr Met Val Ser
            50                  55                  60 tgc ttg gtg gat cac cga ggc aac atc act gag tat cag tgt cac    225
Cys Leu Val Asp His Arg Gly Asn Ile Thr Glu Tyr Gln Cys His
            65                  70                  75 cag tac att acc aag atg acg gcc atc att ttt agt gat tac cgt    270
Gln Tyr Ile Thr Lys Met Thr Ala Ile Ile Phe Ser Asp Tyr Arg
            80                  85                  90 tta atc tgt ggc ttc atg gat gac tgc aaa aat gac atc aac att    315
Leu Ile Cys Gly Phe Met Asp Asp Cys Lys Asn Asp Ile Asn Ile
            95                  100                 105 ctg aaa tgt ggc agt att cgg ctt gga gaa aag gat gca cat tca    360
Leu Lys Cys Gly Ser Ile Arg Leu Gly Glu Lys Asp Ala His Ser
            110                 115                 120 caa ggt gag gtg gta tca tgc ttg gag aaa ggc ctg gtg aaa gaa    405
Gln Gly Glu Val Val Ser Cys Leu Glu Lys Gly Leu Val Lys Glu
            125                 130                 135 gca gaa gaa aga gaa ccc aag att caa gtt tct gaa ctc tgc aag    450
Ala Glu Glu Arg Glu Pro Lys Ile Gln Val Ser Glu Leu Cys Lys
            140                 145                 150 aaa gcc att ctc cgg gtg gct gag ctg tca tcg gat gac ttt cac    495
Lys Ala Ile Leu Arg Val Ala Glu Leu Ser Ser Asp Asp Phe His
            155                 160                 165 tta gac cgg cat tta tat ttt gct tgc cga gat gat cgg gag cgt    540
Leu Asp Arg His Leu Tyr Phe Ala Cys Arg Asp Asp Arg Glu Arg
            170                 175                 180 ttt tgt gaa aat aca caa gct ggt gag ggc aga gtg tat aag tgc    585
Phe Cys Glu Asn Thr Gln Ala Gly Glu Gly Arg Val Tyr Lys Cys
            185                 190                 195 ctc ttt aac cat aaa ttt gaa gaa tcc atg agt gaa aag tgt cga    630
Leu Phe Asn His Lys Phe Glu Glu Ser Met Ser Glu Lys Cys Arg
            200                 205                 210
```

Fig. 10-1

```
gaa gca ctt aca acc cgc caa aag ctg att gcc cag gat tat aaa         675
Glu Ala Leu Thr Thr Arg Gln Lys Leu Ile Ala Gln Asp Tyr Lys
            215                 220                 225 gtc agt tat tca ttg gcc aaa tcc tgt aaa agt gac ttg aag aaa         720
Val Ser Tyr Ser Leu Ala Lys Ser Cys Lys Ser Asp Leu Lys Lys
            230                 235                 240 tac cgg tgc aat gtg gaa aac ctt ccg cga tcg cgt gaa gcc agg         765
Tyr Arg Cys Asn Val Glu Asn Leu Pro Arg Ser Arg Glu Ala Arg
            245                 250                 255 ctc tcc tac ttg tta atg tgc ctg gag tca gct gta cac aga ggg         810
Leu Ser Tyr Leu Leu Met Cys Leu Glu Ser Ala Val His Arg Gly
            260                 265                 270 cga caa gtc agc agt gag tgc cag ggg gag atg ctg gat tac cga         855
Arg Gln Val Ser Ser Glu Cys Gln Gly Glu Met Leu Asp Tyr Arg
            275                 280                 285 cgc atg ttg atg gaa gac ttt tct ctg agc cct gag atc atc cta         900
Arg Met Leu Met Glu Asp Phe Ser Leu Ser Pro Glu Ile Ile Leu
            290                 295                 300 agc tgt cgg ggg gag att gaa cac cat tgt tcc gga tta cat cga         945
Ser Cys Arg Gly Glu Ile Glu His His Cys Ser Gly Leu His Arg
            305                 310                 315 aaa ggg cgg acc cta cac tgt ctg atg aaa gta gtt cga ggg gag         990
Lys Gly Arg Thr Leu His Cys Leu Met Lys Val Val Arg Gly Glu
            320                 325                 330 aag ggg aac ctt gga atg aac tgc cag cag gcg ctt caa aca ctg        1035
Lys Gly Asn Leu Gly Met Asn Cys Gln Gln Ala Leu Gln Thr Leu
            335                 340                 345 att cag gag act gac cct ggt gca gat tac cgc att gat cga gct        1080
Ile Gln Glu Thr Asp Pro Gly Ala Asp Tyr Arg Ile Asp Arg Ala
            350                 355                 360 ttg aat gaa gct tgt gaa tct gta atc cag aca gcc tgc aaa cat        1125
Leu Asn Glu Ala Cys Glu Ser Val Ile Gln Thr Ala Cys Lys His
            365                 370                 375 ata aga tct gga gac cca atg atc ttg tcg tgc ctg atg gaa cat        1170
Ile Arg Ser Gly Asp Pro Met Ile Leu Ser Cys Leu Met Glu His
            380                 385                 390 tta tac aca gag aag atg gta gaa gac tgt gaa cac cgt ctc tta        1215
Leu Tyr Thr Glu Lys Met Val Glu Asp Cys Glu His Arg Leu Leu
            395                 400                 405 gag ctg cag tat ttc atc tcc cgg gat tgg aag ctg gac cct gtc        1260
Glu Leu Gln Tyr Phe Ile Ser Arg Asp Trp Lys Leu Asp Pro Val
            410                 415                 420 ctg tac cgc aag tgc cag gga gac gct tct cgt ctt tgc cac acc        1305
Leu Tyr Arg Lys Cys Gln Gly Asp Ala Ser Arg Leu Cys His Thr
            425                 430                 435 cac ggt tgg aat gag acc agc gaa ttt atg cct cag gga gct gtg        1350
His Gly Trp Asn Glu Thr Ser Glu Phe Met Pro Gln Gly Ala Val
            440                 445                 450 ttc tct tgt tta tac aga cac gcc tac cgc act gag gaa cag gga        1395
Phe Ser Cys Leu Tyr Arg His Ala Tyr Arg Thr Glu Glu Gln Gly
            455                 460                 465
```

Fig. 10-2

```
agg agg ctc tca cgg gag tgc cga gct gaa gtc caa agg atc cta      1440
Arg Arg Leu Ser Arg Glu Cys Arg Ala Glu Val Gln Arg Ile Leu
                470             475             480 cac cag cgt gcc atg gat gtc aag ctg gat cct gcc ctc cag gat      1485
His Gln Arg Ala Met Asp Val Lys Leu Asp Pro Ala Leu Gln Asp
                485             490             495 aag tgc ctg att gat ctg gga aaa tgg tgc agt gag aaa aca gag      1530
Lys Cys Leu Ile Asp Leu Gly Lys Trp Cys Ser Glu Lys Thr Glu
                500             505             510 act gga cag aag ctg gag tgc ctt cag gac cat ctg gat gac tta      1575
Thr Gly Gln Lys Leu Glu Cys Leu Gln Asp His Leu Asp Asp Leu
                515             520             525 gtg gtg gag tgt aga gat ata gtt ggc aac ctc act gag tta gaa      1620
Val Val Glu Cys Arg Asp Ile Val Gly Asn Leu Thr Glu Leu Glu
                530             535             540 tca gag gat att caa ata gaa gcc ttg ctg atg aga gcc tgt gag      1665
Ser Glu Asp Ile Gln Ile Glu Ala Leu Leu Met Arg Ala Cys Glu
                545             550             555 ccc ata att cag aac ttc tgc cac gat gtg gca gat aac cag ata      1710
Pro Ile Ile Gln Asn Phe Cys His Asp Val Ala Asp Asn Gln Ile
                560             565             570 gac tcc ggg gac ctg atg gag tgt ctg ata cag aac aaa cac cag      1755
Asp Ser Gly Asp Leu Met Glu Cys Leu Ile Gln Asn Lys His Gln
                575             580             585 aag gac atg aac gag aag tgt gcc atc gga gtt acc cac ttc cag      1800
Lys Asp Met Asn Glu Lys Cys Ala Ile Gly Val Thr His Phe Gln
                590             595             600 ctg gtg cag atg aag gat ttt cgg ttt tct tac aag ttt aaa atg      1845
Leu Val Gln Met Lys Asp Phe Arg Phe Ser Tyr Lys Phe Lys Met
                605             610             615 gcc tgc aag gag gac gtg ttg aag ctt tgc cca aac ata aaa aag      1890
Ala Cys Lys Glu Asp Val Leu Lys Leu Cys Pro Asn Ile Lys Lys
                620             625             630 aag gtg gac gtg gtg atc tgc ctg agc acg acc gtg cgc aat gac      1935
Lys Val Asp Val Val Ile Cys Leu Ser Thr Thr Val Arg Asn Asp
                635             640             645 act ctg cag gaa gcc aag gag cac agg gtg tcc ctg aag tgc cgc      1980
Thr Leu Gln Glu Ala Lys Glu His Arg Val Ser Leu Lys Cys Arg
                650             655             660 agg cag ctc cgt gtg gag gag ctg gag atg acg gag gac atc cgc      2025
Arg Gln Leu Arg Val Glu Glu Leu Glu Met Thr Glu Asp Ile Arg
                665             670             675 ttg gag cca gat cta tac gaa gcc tgc aag agt gac atc aaa aac      2070
Leu Glu Pro Asp Leu Tyr Glu Ala Cys Lys Ser Asp Ile Lys Asn
                680             685             690 ttc tgt tcc gct gtg caa tat ggc aac gct cag att atc gaa tgt      2115
Phe Cys Ser Ala Val Gln Tyr Gly Asn Ala Gln Ile Ile Glu Cys
                695             700             705 ctg aaa gaa aac aag aag cag cta agc acc cgc tgc cac caa aaa      2160
Leu Lys Glu Asn Lys Lys Gln Leu Ser Thr Arg Cys His Gln Lys
                710             715             720
```

Fig. 10-3

```
gta ttt aag ctg cag gag aca gag atg atg gac cca gag cta gac      2205
Val Phe Lys Leu Gln Glu Thr Glu Met Met Asp Pro Glu Leu Asp
            725                 730                 735 tac acc ctc atg agg gtc tgc aag cag atg ata aag aag ttc tgt      2250
Tyr Thr Leu Met Arg Val Cys Lys Gln Met Ile Lys Lys Phe Cys
            740                 745                 750 ccg gaa gca gat tct aaa acc atg ttg cag tgc ttg aag caa aat      2295
Pro Glu Ala Asp Ser Lys Thr Met Leu Gln Cys Leu Lys Gln Asn
            755                 760                 765 aaa aac agt gaa ttg atg gat ccc aaa tgc aaa cag atg ata acc      2340
Lys Asn Ser Glu Leu Met Asp Pro Lys Cys Lys Gln Met Ile Thr
            770                 775                 780 aag cgc cag atc acc cag aac aca gat tac cgc tta aac ccc atg      2385
Lys Arg Gln Ile Thr Gln Asn Thr Asp Tyr Arg Leu Asn Pro Met
            785                 790                 795 tta aga aaa gcc tgt aaa gct gac att cct aaa ttc tgt cac ggt      2430
Leu Arg Lys Ala Cys Lys Ala Asp Ile Pro Lys Phe Cys His Gly
            800                 805                 810 atc ctg act aag gcc aag gat gat tca gaa tta gaa gga caa gtc      2475
Ile Leu Thr Lys Ala Lys Asp Asp Ser Glu Leu Glu Gly Gln Val
            815                 820                 825 atc tct tgc ctg aag ctg aga tat gct gac cag cgc ctg tct tca      2520
Ile Ser Cys Leu Lys Leu Arg Tyr Ala Asp Gln Arg Leu Ser Ser
            830                 835                 840 gac tgt gaa gac cag atc cga atc att atc cag gag tcc gcc ctg      2565
Asp Cys Glu Asp Gln Ile Arg Ile Ile Ile Gln Glu Ser Ala Leu
            845                 850                 855 gac tac cgc ctg gat cct cag ctc cag ctg cac tgc tca gac gag      2610
Asp Tyr Arg Leu Asp Pro Gln Leu Gln Leu His Cys Ser Asp Glu
            860                 865                 870 atc tcc agt cta tgt gct gaa gaa gca gca gcc caa gag cag aca      2655
Ile Ser Ser Leu Cys Ala Glu Glu Ala Ala Ala Gln Glu Gln Thr
            875                 880                 885 ggt cag gtg gag gag tgc ctc aag gtc aac ctg ctc aag atc aaa      2700
Gly Gln Val Glu Glu Cys Leu Lys Val Asn Leu Leu Lys Ile Lys
            890                 895                 900 aca gaa ttg tgt aaa aag gaa gtg cta aac atg ctg aag gaa agc      2745
Thr Glu Leu Cys Lys Lys Glu Val Leu Asn Met Leu Lys Glu Ser
            905                 910                 915 aaa gca gac atc ttt gtt gac ccg gta ctt cat act gct tgt gcc      2790
Lys Ala Asp Ile Phe Val Asp Pro Val Leu His Thr Ala Cys Ala
            920                 925                 930 ctg gac att aaa cac cac tgc gca gcc atc acc cct ggc cgc ggg      2835
Leu Asp Ile Lys His His Cys Ala Ala Ile Thr Pro Gly Arg Gly
            935                 940                 945 cgt caa atg tcc tgt ctc atg gaa gca ctg gag gat aag cgg gtc      2880
Arg Gln Met Ser Cys Leu Met Glu Ala Leu Glu Asp Lys Arg Val
            950                 955                 960 agg tta cag ccc gag tgc aaa aag cgc ctc aat gac cgg att gag      2925
Arg Leu Gln Pro Glu Cys Lys Lys Arg Leu Asn Asp Arg Ile Glu
            965                 970                 975
```

Fig. 10-4

```
atg tgg agt tac gca gca aag gtg gcc cca gca gat ggc ttc tct
Met Trp Ser Tyr Ala Ala Lys Val Ala Pro Ala Asp Gly Phe Ser      2970
            980         985                         990 gat ctt gcc atg caa gta atg acg tct cca tct aag aac tac att
Asp Leu Ala Met Gln Val Met Thr Ser Pro Ser Lys Asn Tyr Ile      3015
            995                 1000                1005 ctc tct gtg atc agt ggg agc atc tgt ata ttc ctg att ggc
Leu Ser Val Ile Ser Gly Ser Ile Cys Ile Leu Phe Leu Ile Gly      3060
            1010            1015                1020 ctg atg tgt gga cgg atc acc aag cga gtg aca cga gag ctc aag
Leu Met Cys Gly Arg Ile Thr Lys Arg Val Thr Arg Glu Leu LysA     3105
            1025            1030                1035 gac agg tag
Asp Arg ***
        1038
```

Fig. 10-5

```
23132        1  ------------ ---------- ---------- ---------- ---------- ---------- ---------- ---------- ---------- PPPAGGPP-P
CFR-1        1  MAACGRVERM FRLSAALHIL LLFAAGGRNS PARASHSGQ GPGANFVSFV GQAGGGGPAG QQLPQLPQSS QLQQQQQQQQ QQQQPQPPQP PPPAGGPPAR
MG160        1  MAACGRVBRM FRLSAALHIL LLFAAGAEKL PGHGVHSQGO ---------- GQAGGGGPAG QQLPQLQSS QLQQQQQQQQ QQQQLQPPQP PPPAGGPPAR 23132      101  ---------- ---------- ---------- ---------- -DVREPENE ISSDCNHLLW NYKLNLTTDP KFESVAREVC KSTITEIKSC ADEPVGKGYM
CFR-1      101  RSGAGAGGGW KLAEEESCRE DVTRVCPKHT WSNNLAVLEC LQDVREPENE ISSDCNHLLW NYKLNLTTDP KFESVAREVC KST-TEIKSC ADEPVGKGYM
MG160      101  RSGAGAGGGW KLAEEESCRE DVTRVCPKHT WSNNLAVLEC LQDVREPENE ISSDCNHLLW NYKLNLTTDP KFESVAREVC KSTITEIKSC ADEPVGKGYM 23132      201  VSCLVDHRGN ITEYQCHQYI TKMTAIIFSD YRLICGFMDD CKNDINILKC GSIRLGEKDA HSQGEVVSCL EKGLVKEAEE REPKIQVSEL CKKAILRVAE
CFR-1      201  VSCLVDHRGN ITEYQCHQYI TKNTAIIFSD YRLICGFMDD CKNDINILKC GSIRLGEKDA HSQGEVVSCL EKGLVKEAEE REPKIQVSEL CKKAILRVAE
MG160      201  VSCLVDHRGN TKMTAIIFSD YRLICGFMDD CKNDINILKC GSIRLGEKDA HSQGEVVSCL EKGLVKEAEE REPKIQVSEL CKKAILRVAE 23132      301  LSSDDFHLDR HLYFACRDDR ERFCENTQAG EGRVYKCLFN HKEEESMSEK CREALTTRQK LRAQDYKVSY SLAKSCKSDL KKYRCNVENL PRSREARLSY
CFR-1      301  LSSDDFHLDR HLYFACRDDR ERFCENTQAG EGRVYKCLFN HKEEESMSEK CREALTTRQK LRAQDYKVSY SLAKSCKSDL KKYRCNVENL PRSREARLSY
MG160      301  LSSDDFHLDR HLYFACRDDR ERFCENTQAG EGRVYKCLFN HKEEESMSEK CREALTTRQK LRAQDYKVSY SLAKSCKSDL KKYRCNVENL PRSREARLSY 23132      401  LLMCLESAVH KGRQVSSECQ GEMLDYRRML MEDFSLSPEI LLSCRGEIEH HCSGLHRKGR TLHCLMKVVR GEKGNLGMNC QQALQTLIQE TDPGADYRID
CFR-1      401  LLMCLESAVH KGRQVSSRCQ GEMLDYRRML MEDFSLSPEI ILSCRGEIEH HCSGLHRKGR TLHCLMKVVR GEKGNLGMNC QQALQTLIQE TDPGADYRID
MG160      401  LLMCLESAVH KGRQVSSCQ GEMLDYRRML MEDFSLSPEI ILSCRGEIEH HCSGLHRKGR TLHCLMKVVR GEKGNLGMNC QQALQTLIQE TDPGADYRID 23132      501  RALNEACESV IQTACKHIRS GDPMILSCLM EHLYTEKMVE DCEHRLLELQ YFISRDWKLD PVLYRKCQGD ASRLCHTHGW NETSEFMPQG AVFSCLYRHA
CFR-1      501  RALNEACESV IQTACKHIRS GDPMISSCLM EHLYTEKMVE DCEHRLLELQ YFISRDWKLD PVLYRKCQGD ASRLCHTHGW NETSEFMPQG AVFSCLYRHA
MG160      501  RALNEACESV IQTACKHIRS GDPMILSCLM EHLYTEKMVE DCEHRLLELQ YFISRDWKLD PVLYRKCQGD ASRLCHTHGW NETSEFMPQG AVFSCLYRHA 23132      601  YRTEEQGRRL SRECRAEVQR ILHQRAMDVK LDPALQDKCL IDLGKWNCSEK TETGQELECL QDHLDDLVVE CRDIVGNLTE LESEDIQIEA LLMRACEPII
CFR-1      601  YRTEEQGRRL SRECRAEVQR ILHQRAMDVK LDPALQDKCL IDLGKWNCSEK TETGQELECL QDHLDDLVVE CRDIVGNLTE LESEDIQIEA LLMRACEPII
MG160      601  YRTEEQGRRL LDPALQDKCL IDLGKWCSEK TETGQELECL ILHQRAMDVK SRECRAEVQR QDHLDDLVVE CRDIVGNLTE LESEDIQIEA LLMRACEPII 23132      701  QNFCHQVADN QIDSGDLMEC LIQNKHQKDM NEKCAIGVTH FQLVQMKDFR FSYKFKMACK EDVLKLCPNI KKKVDVVICL STTVRNDTLQ EAKEHRVSLK
CFR-1      701  QTFCFD-ADN QIDSGDLMEC LIQNKHQKDM NEKCAIGVTH FQLVQMKDFR FSYKFKMACK EDVLKLCPNI KKKVDVVICL STTVRNDTLQ EAKEHRVSLK
MG160      701  QNFCHQVADN QIDSGDLMEC LIQNKHQKDM NEKCAIGVTH FQLVQMKDFR FSYKFKMACK EDVLKLCPNI KKKVDVVICL STTVRNDTLQ EAKEHRVSLK 23132      801  CRRQLRVEEL EMTEDIRLEP DLYEACKSDI KNFCSAVQYG NAQIIECLKE NKKQLSTRCH QKVFKLQETE MMDPELDYTL MRVCKQMIKK FCPEADSKTM
CFR-1      801  CRRQLRVEEL EMTEDIRLEP DLYEACKSDI KNFCSAVQYG NAQIIECLKE NKKQLSTRCH QKVFKLQETE MMDPELDYTL MRVCKQMIKR FCPEADSKTM
MG160      801  CRRQLRVEEL EMTEDIRLEP DLYEACKSDI KNFCSAVQYG NAQIIECLKE NKKQLSTRCH QKVFKLQETE MMDPELDYTL MRVCKQMIKR FCPEADSKTM 23132      901  LQCLKQNKNS ELMDPKCKQM ITKRQITQNT DYRLNPMLRK ACKADIPKFC HGILTKARDD SELEGQVISC LKLRYADQRL SSDCEDQIRI IIQESALDYR
CFR-1      901  LQCLKQNKNS ELMDPKCKQM ITKRQITQNT DYRLNPMLRK ACKADIPKFC HGILTKAKDD SELEGQVISC LKLRYADQRL SSDCEDQIRI IIQESALDYR
MG160      901  LQCLKQNKNS ELMDPKCKQM ITKRQITQNT DYRLNPMLRK ACKADIPKFC HGILTKAKDD SELEGQVISC LKLRYADQRL SSDCEDQIRI IIQESALDYR 23132     1001  LDPQLQLHCS DEISSLCAEE AAAQEQTGQV EECLKVNLLK IKTELCKKEV LNMLKESEAD IFVDPVLHTA CALDIKHHCA AITPGRGRQM SCLMEALEDK
CFR-1     1001  LDPQLQLHCS DEISSLCAEE AAAQEQTGQV EECLKVNLLK IKTELCKKEV LNMLKESKAD IFVDPVLHTA CALDIKHHCA AITPGRGRQM SCLMEALEDK
MG160     1001  LDPQLQLHCS DEISSLCREE AAAQEQTGQV EECLKVNLLK IKTELCKKEV LNMLKESKAD IFVDPVLHTA CALDIKHHCA AITPGRGRQM SCLMEALEDK 23132     1101  RVRLQPECKK RLNDRIEMWS YAAKVAPADG FSDLAMQVMT SPSKNYILSV ISGSCILFL IGLMCGRITK RVTRELKDR*
CFR-1     1101  RVRLQPECKK RLNDRIEMWS YAAKVAPADG FSDLAMQVMT SPSKNYILSV ISGSCILFL IGLMCGRITK RVTRELKDR*
MG160     1101  RVRLQPECKK RLNDRIEMWS YAAKVAPADG FSDLAMQVMT SPSKNYILSV ISGSCILFL IGLMCGRITK RVTRELKDR*
```

Fig. 16

Human antibody PAM-1 (clone 103/51)

Heavy chain sequence

```
                                          CDR I
                                    ─────────────────────────────
AGG TCC CTG AGA CTC TCC TGT GCA GCC TCT GGA TTC ACC TTC AGT AGC TAT GGC    54
Arg Ser Leu Arg Leu Ser Cys Ala Ala Ser Gly Phe Thr Phe Ser Ser Tyr Gly
             5                  10                  15
                                                              ───────────
ATG CAC TGG GTC CGC CAG GCT CCA GGC AAG GGG CTG GAG TGG GTG GCA GTT ATA   108
Met His Trp Val Arg Gln Ala Pro Gly Lys Gly Leu Glu Trp Val Ala Val Ile
     20                  25                  30                  35

CDR II
─────────────────────────────────────────────────
TCA TAT GAT GGA AGT AAT AAA TAC TAT GCA GAC TCC GTG AAG GGC CGA TTC ACC   162
Ser Tyr Asp Gly Ser Asn Lys Tyr Tyr Ala Asp Ser Val Lys Gly Arg Phe Thr
             40                  45                  50

ATC TCC AGA GAC AAT TCC AAG AAC ACG CTG TAT CTG CAA ATG AAC AGC CTG AGA   216
Ile Ser Arg Asp Asn Ser Lys Asn Thr Leu Tyr Leu Gln Met Asn Ser Leu Arg
55                  60                  65                  70
                                                        CDR III
                                                    ─────────────────────
GCT GAG GAC ACG GCT GTG TAT TAC TGT GCG AGG TCG ACT ACG AGG TCT TAT CCT   270
Ala Glu Asp Thr Ala Val Tyr Tyr Cys Ala Arg Ser Thr Thr Arg Ser Tyr Pro
             75                  80                  85                90

CDR III
─────────────────────────────────────
CTA TAC GGT ATG GAC GTT TGG GGC CAA GGG AAC CCT GTC ACC                   312
Leu Tyr Gly Met Asp Val Trp Gly Gln Gly Asn Pro Val Thr
             95                  100
```

Fig. 17

Human antibody PAM-1 (clone 103/51)

Light chain sequence

```
GTG ACC TCC TAT GTG CTG ACT CAG CCA CCC TCG GTG TCA GTG GCC CCA GGA CAG   54
Val Thr Ser Tyr Val Leu Thr Gln Pro Pro Ser Val Ser Val Ala Pro Gly Gln
            5                   10                  15
                                    CDR I
                            ─────────────────────────────────────────────
ACG GCC AGT ATT ACC TGT GGG GGA AAT AAC ATT GGA AGT AAA AGT GTG CAC TGG  108
Thr Ala Ser Ile Thr Cys Gly Gly Asn Asn Ile Gly Ser Lys Ser Val His Trp
        20              25                  30                  35
                                                            CDR II
                                                        ────────────────
TAC CAT CAG AAG CCA GGC CAG GCC CCT GTG CTG GTC GTC TAT GAT GAT AGC GAC  162
Tyr His Gln Lys Pro Gly Gln Ala Pro Val Leu Val Val Tyr Asp Asp Ser Asp
                40                  45                  50
────

CGG CCC TCA GGG ATC CCT GAG CGA TTC TCT GGC TCC AAC TCT GGG AAC ACG GCC  216
Arg Pro Ser Gly Ile Pro Glu Arg Phe Ser Gly Ser Asn Ser Gly Asn Thr Ala
55                  60                  65                  70

ACC CTG ACC ATC ACC AGG GTC GAA GCC GGG GAT GAG GCC GAC TAT TAC TGT CAG  270
Thr Leu Thr Ile Thr Arg Val Glu Ala Gly Asp Glu Ala Asp Tyr Tyr Cys Gln
        75                  80                  85                  90

CDR III
─────────────────────────────────────────────
GTG TGG GAT AGT AGT AGT GAT CTC AAT TGG GTG TTC GGC GGA AGG ACC CAA GCT  324
Val Trp Asp Ser Ser Ser Asp Leu Asn Trp Val Phe Gly Gly Arg Thr Gln Ala
                95                  100                 105

GAC CGT CCT ACG TCA GCC CAA GGC TGC CCC TCC GGT CAC TCT GTT CCC CGC CCC  378
Asp Arg Pro Thr Ser Ala Gln Gly Cys Pro Ser Gly His Ser Val Pro Arg Pro
        110                 115                 120                 125

CCT CTG AAG AGC TTC AAG CTT  399
Pro Leu Lys Ser Phe Lys Leu
            130
```

Fig. 18

SEQUENCE LISTING

```
<160> NUMBER OF SEQ ID NOS: 30

<210> SEQ ID NO 1
<211> LENGTH: 288
<212> TYPE: DNA
<213> ORGANISM: Mus musculus
<220> FEATURE:
<221> NAME/KEY: CDS
<222> LOCATION: (1)...(288)

<400> SEQUENCE: 1 tcc tgc aag gct tct ggc tac acc ttc act gac tac tat ata aac tgg      48
Ser Cys Lys Ala Ser Gly Tyr Thr Phe Thr Asp Tyr Tyr Ile Asn Trp
 1               5                  10                  15 gtg aag cag agg act gga cag ggc ctt gag tgg att gga gag att tat      96
Val Lys Gln Arg Thr Gly Gln Gly Leu Glu Trp Ile Gly Glu Ile Tyr
             20                  25                  30 cct gga agt ggt aat act tac tac aat gag aag ttc aag ggc aag gcc     144
Pro Gly Ser Gly Asn Thr Tyr Tyr Asn Glu Lys Phe Lys Gly Lys Ala
         35                  40                  45 aca ctg act gca gac aaa tcc tcc agc aca gcc tac atg cag ctc agc     192
Thr Leu Thr Ala Asp Lys Ser Ser Ser Thr Ala Tyr Met Gln Leu Ser
     50                  55                  60 agc ctg aca tct gag gac tct gca gtc tat ttc tgt gca aga tcg gga     240
Ser Leu Thr Ser Glu Asp Ser Ala Val Tyr Phe Cys Ala Arg Ser Gly
 65                  70                  75                  80 tta cga ccc tat gct atg gac tac tgg ggt caa gga acc tca gtc acc     288
Leu Arg Pro Tyr Ala Met Asp Tyr Trp Gly Gln Gly Thr Ser Val Thr
                 85                  90                  95

<210> SEQ ID NO 2
<211> LENGTH: 96
<212> TYPE: PRT
<213> ORGANISM: Mus musculus
```

<400> SEQUENCE: 2

| Ser | Cys | Lys | Ala | Ser | Gly | Tyr | Thr | Phe | Thr | Asp | Tyr | Tyr | Ile | Asn | Trp |
|---|---|---|---|---|---|---|---|---|---|---|---|---|---|---|---|
| 1 | | | | 5 | | | | | 10 | | | | | 15 | |

| Val | Lys | Gln | Arg | Thr | Gly | Gln | Gly | Leu | Glu | Trp | Ile | Gly | Glu | Ile | Tyr |
|---|---|---|---|---|---|---|---|---|---|---|---|---|---|---|---|
| | | | 20 | | | | | 25 | | | | | 30 | | |

| Pro | Gly | Ser | Gly | Asn | Thr | Tyr | Tyr | Asn | Glu | Lys | Phe | Lys | Gly | Lys | Ala |
|---|---|---|---|---|---|---|---|---|---|---|---|---|---|---|---|
| | | | | 35 | | | | | 40 | | | | | 45 | |

| Thr | Leu | Thr | Ala | Asp | Lys | Ser | Ser | Thr | Ala | Tyr | Met | Gln | Leu | Ser |
|---|---|---|---|---|---|---|---|---|---|---|---|---|---|---|
| | 50 | | | | | 55 | | | | | 60 | | | |

| Ser | Leu | Thr | Ser | Glu | Asp | Ser | Ala | Val | Tyr | Phe | Cys | Ala | Arg | Ser | Gly |
|---|---|---|---|---|---|---|---|---|---|---|---|---|---|---|---|
| 65 | | | | | 70 | | | | | 75 | | | | | 80 |

| Leu | Arg | Pro | Tyr | Ala | Met | Asp | Tyr | Trp | Gly | Gln | Gly | Thr | Ser | Val | Thr |
|---|---|---|---|---|---|---|---|---|---|---|---|---|---|---|---|
| | | | | 85 | | | | | 90 | | | | | 95 | |

<210> SEQ ID NO 3
<211> LENGTH: 315
<212> TYPE: DNA
<213> ORGANISM: Mus musculus
<220> FEATURE:
<221> NAME/KEY: CDS
<222> LOCATION: (1)...(315)

<400> SEQUENCE: 3

| cca | ctc | tcc | ctg | cct | gtc | agt | ctt | gga | gat | caa | gcc | tcc | atc | tct | tgc | 48 |
|---|---|---|---|---|---|---|---|---|---|---|---|---|---|---|---|---|
| Pro | Leu | Ser | Leu | Pro | Val | Ser | Leu | Gly | Asp | Gln | Ala | Ser | Ile | Ser | Cys | |
| 1 | | | | 5 | | | | | 10 | | | | | 15 | | |

| aga | tct | agt | cag | agc | att | gta | cat | agt | aat | gga | aac | acc | tat | tta | gaa | 96 |
|---|---|---|---|---|---|---|---|---|---|---|---|---|---|---|---|---|
| Arg | Ser | Ser | Gln | Ser | Ile | Val | His | Ser | Asn | Gly | Asn | Thr | Tyr | Leu | Glu | |
| | | | 20 | | | | | 25 | | | | | 30 | | | |

| tgg | tac | ctg | cag | aaa | cca | ggc | cag | tct | cca | aag | ctc | ctg | atc | tac | aaa | 144 |
|---|---|---|---|---|---|---|---|---|---|---|---|---|---|---|---|---|
| Trp | Tyr | Leu | Gln | Lys | Pro | Gly | Gln | Ser | Pro | Lys | Leu | Leu | Ile | Tyr | Lys | |
| | | | | 35 | | | | | 40 | | | | | 45 | | |

| gtt | tcc | aac | cga | ttt | tct | ggg | gtc | cca | gac | agg | ttc | agt | ggc | agt | gga | 192 |
|---|---|---|---|---|---|---|---|---|---|---|---|---|---|---|---|---|
| Val | Ser | Asn | Arg | Phe | Ser | Gly | Val | Pro | Asp | Arg | Phe | Ser | Gly | Ser | Gly | |
| | 50 | | | | | 55 | | | | | 60 | | | | | |

| tca | ggg | aca | gat | ttc | aca | ctc | aag | atc | agc | aga | gtg | gag | gct | gag | gat | 240 |
|---|---|---|---|---|---|---|---|---|---|---|---|---|---|---|---|---|
| Ser | Gly | Thr | Asp | Phe | Thr | Leu | Lys | Ile | Ser | Arg | Val | Glu | Ala | Glu | Asp | |
| 65 | | | | | 70 | | | | | 75 | | | | | 80 | |

| ctg | gga | gtt | tat | tac | tgc | ttt | caa | ggt | tca | cat | gtt | ccg | tac | acg | ttc | 288 |
|---|---|---|---|---|---|---|---|---|---|---|---|---|---|---|---|---|
| Leu | Gly | Val | Tyr | Tyr | Cys | Phe | Gln | Gly | Ser | His | Val | Pro | Tyr | Thr | Phe | |
| | | | | 85 | | | | | 90 | | | | | 95 | | |

| gga | ggg | ggg | acc | aag | ctg | gaa | ata | aaa | 315 |
|---|---|---|---|---|---|---|---|---|---|
| Gly | Gly | Gly | Thr | Lys | Leu | Glu | Ile | Lys | |
| | | | 100 | | | | | 105 | |

<210> SEQ ID NO 4
<211> LENGTH: 105
<212> TYPE: PRT
<213> ORGANISM: Mus musculus

<400> SEQUENCE: 4

| Pro | Leu | Ser | Leu | Pro | Val | Ser | Leu | Gly | Asp | Gln | Ala | Ser | Ile | Ser | Cys |
|---|---|---|---|---|---|---|---|---|---|---|---|---|---|---|---|
| 1 | | | | 5 | | | | | 10 | | | | | 15 | |

| Arg | Ser | Ser | Gln | Ser | Ile | Val | His | Ser | Asn | Gly | Asn | Thr | Tyr | Leu | Glu |
|---|---|---|---|---|---|---|---|---|---|---|---|---|---|---|---|
| | | | 20 | | | | | 25 | | | | | 30 | | |

| Trp | Tyr | Leu | Gln | Lys | Pro | Gly | Gln | Ser | Pro | Lys | Leu | Leu | Ile | Tyr | Lys |
|---|---|---|---|---|---|---|---|---|---|---|---|---|---|---|---|
| | | | | 35 | | | | | 40 | | | | | 45 | |

| Val | Ser | Asn | Arg | Phe | Ser | Gly | Val | Pro | Asp | Arg | Phe | Ser | Gly | Ser | Gly |
|---|---|---|---|---|---|---|---|---|---|---|---|---|---|---|---|
| | 50 | | | | | 55 | | | | | 60 | | | | |

```
Ser Gly Thr Asp Phe Thr Leu Lys Ile Ser Arg Val Glu Ala Glu Asp
 65                  70                  75                  80

Leu Gly Val Tyr Tyr Cys Phe Gln Gly Ser His Val Pro Tyr Thr Phe
                 85                  90                  95

Gly Gly Gly Thr Lys Leu Glu Ile Lys
            100                 105

<210> SEQ ID NO 5
<211> LENGTH: 3114
<212> TYPE: DNA
<213> ORGANISM: Homo sapiens
<220> FEATURE:
<221> NAME/KEY: CDS
<222> LOCATION: (1)...(3114)

<400> SEQUENCE: 5 gat gtg agg gag cct gaa aat gaa att tct tca gac tgc aat cat ttg     48
Asp Val Arg Glu Pro Glu Asn Glu Ile Ser Ser Asp Cys Asn His Leu
 1               5                  10                  15 ttg tgg aat tat aag ctg aac cta act aca gat ccc aaa ttt gaa tct     96
Leu Trp Asn Tyr Lys Leu Asn Leu Thr Thr Asp Pro Lys Phe Glu Ser
             20                  25                  30 gtg gcc aga gag gtt tgc aaa tct act ata aca gag att gaa gaa tgt    144
Val Ala Arg Glu Val Cys Lys Ser Thr Ile Thr Glu Ile Glu Glu Cys
         35                  40                  45 gct gat gaa ccg gtt gga aaa ggt tac atg gtt tcc tgc ttg gtg gat    192
Ala Asp Glu Pro Val Gly Lys Gly Tyr Met Val Ser Cys Leu Val Asp
     50                  55                  60 cac cga ggc aac atc act gag tat cag tgt cac cag tac att acc aag    240
His Arg Gly Asn Ile Thr Glu Tyr Gln Cys His Gln Tyr Ile Thr Lys
 65                  70                  75                  80 atg acg gcc atc att ttt agt gat tac cgt tta atc tgt ggc ttc atg    288
Met Thr Ala Ile Ile Phe Ser Asp Tyr Arg Leu Ile Cys Gly Phe Met
             85                  90                  95 gat gac tgc aaa aat gac atc aac att ctg aaa tgt ggc agt att cgg    336
Asp Asp Cys Lys Asn Asp Ile Asn Ile Leu Lys Cys Gly Ser Ile Arg
            100                 105                 110 ctt gga gaa aag gat gca cat tca caa ggt gag gtg gta tca tgc ttg    384
Leu Gly Glu Lys Asp Ala His Ser Gln Gly Glu Val Val Ser Cys Leu
        115                 120                 125 gag aaa ggc ctg gtg aaa gaa gca gaa gaa aga gaa ccc aag att caa    432
Glu Lys Gly Leu Val Lys Glu Ala Glu Glu Arg Glu Pro Lys Ile Gln
    130                 135                 140 gtt tct gaa ctc tgc aag aaa gcc att ctc cgg gtg gct gag ctg tca    480
Val Ser Glu Leu Cys Lys Lys Ala Ile Leu Arg Val Ala Glu Leu Ser
145                 150                 155                 160 tcg gat gac ttt cac tta gac cgg cat tta tat ttt gct tgc cga gat    528
Ser Asp Asp Phe His Leu Asp Arg His Leu Tyr Phe Ala Cys Arg Asp
                165                 170                 175 gat cgg gag cgt ttt tgt gaa aat aca caa gct ggt gag ggc aga gtg    576
Asp Arg Glu Arg Phe Cys Glu Asn Thr Gln Ala Gly Glu Gly Arg Val
            180                 185                 190 tat aag tgc ctc ttt aac cat aaa ttt gaa gaa tcc atg agt gaa aag    624
Tyr Lys Cys Leu Phe Asn His Lys Phe Glu Glu Ser Met Ser Glu Lys
        195                 200                 205 tgt cga gaa gca ctt aca acc cgc caa aag ctg att gcc cag gat tat    672
Cys Arg Glu Ala Leu Thr Thr Arg Gln Lys Leu Ile Ala Gln Asp Tyr
    210                 215                 220 aaa gtc agt tat tca ttg gcc aaa tcc tgt aaa agt gac ttg aag aaa    720
Lys Val Ser Tyr Ser Leu Ala Lys Ser Cys Lys Ser Asp Leu Lys Lys
```

```
                    225                 230                 235                 240
tac cgg tgc aat gtg gaa aac ctt ccg cga tcg cgt gaa gcc agg ctc        768
Tyr Arg Cys Asn Val Glu Asn Leu Pro Arg Ser Arg Glu Ala Arg Leu
                245                 250                 255 tcc tac ttg tta atg tgc ctg gag tca gct gta cac aga ggg cga caa        816
Ser Tyr Leu Leu Met Cys Leu Glu Ser Ala Val His Arg Gly Arg Gln
            260                 265                 270 gtc agc agt gag tgc cag ggg gag atg ctg gat tac cga cgc atg ttg        864
Val Ser Ser Glu Cys Gln Gly Glu Met Leu Asp Tyr Arg Arg Met Leu
        275                 280                 285 atg gaa gac ttt tct ctg agc cct gag atc atc cta agc tgt cgg ggg        912
Met Glu Asp Phe Ser Leu Ser Pro Glu Ile Ile Leu Ser Cys Arg Gly
    290                 295                 300 gag att gaa cac cat tgt tcc gga tta cat cga aaa ggg cgg acc cta        960
Glu Ile Glu His His Cys Ser Gly Leu His Arg Lys Gly Arg Thr Leu
305                 310                 315                 320 cac tgt ctg atg aaa gta gtt cga ggg gag aag ggg aac ctt gga atg       1008
His Cys Leu Met Lys Val Val Arg Gly Glu Lys Gly Asn Leu Gly Met
                325                 330                 335 aac tgc cag cag gcg ctt caa aca ctg att cag gag act gac cct ggt       1056
Asn Cys Gln Gln Ala Leu Gln Thr Leu Ile Gln Glu Thr Asp Pro Gly
            340                 345                 350 gca gat tac cgc att gat cga gct ttg aat gaa gct tgt gaa tct gta       1104
Ala Asp Tyr Arg Ile Asp Arg Ala Leu Asn Glu Ala Cys Glu Ser Val
        355                 360                 365 atc cag aca gcc tgc aaa cat ata aga tct gga gac cca atg atc ttg       1152
Ile Gln Thr Ala Cys Lys His Ile Arg Ser Gly Asp Pro Met Ile Leu
    370                 375                 380 tcg tgc ctg atg gaa cat tta tac aca gag aag atg gta gaa gac tgt       1200
Ser Cys Leu Met Glu His Leu Tyr Thr Glu Lys Met Val Glu Asp Cys
385                 390                 395                 400 gaa cac cgt ctc tta gag ctg cag tat ttc atc tcc cgg gat tgg aag       1248
Glu His Arg Leu Leu Glu Leu Gln Tyr Phe Ile Ser Arg Asp Trp Lys
                405                 410                 415 ctg gac cct gtc ctg tac cgc aag tgc cag gga gac gct tct cgt ctt       1296
Leu Asp Pro Val Leu Tyr Arg Lys Cys Gln Gly Asp Ala Ser Arg Leu
            420                 425                 430 tgc cac acc cac ggt tgg aat gag acc agc gaa ttt atg cct cag gga       1344
Cys His Thr His Gly Trp Asn Glu Thr Ser Glu Phe Met Pro Gln Gly
        435                 440                 445 gct gtg ttc tct tgt tta tac aga cac gcc tac cgc act gag gaa cag       1392
Ala Val Phe Ser Cys Leu Tyr Arg His Ala Tyr Arg Thr Glu Glu Gln
    450                 455                 460 gga agg agg ctc tca cgg gag tgc cga gct gaa gtc caa agg atc cta       1440
Gly Arg Arg Leu Ser Arg Glu Cys Arg Ala Glu Val Gln Arg Ile Leu
465                 470                 475                 480 cac cag cgt gcc atg gat gtc aag ctg gat cct gcc ctc cag gat aag       1488
His Gln Arg Ala Met Asp Val Lys Leu Asp Pro Ala Leu Gln Asp Lys
                485                 490                 495 tgc ctg att gat ctg gga aaa tgg tgc agt gag aaa aca gag act gga       1536
Cys Leu Ile Asp Leu Gly Lys Trp Cys Ser Glu Lys Thr Glu Thr Gly
            500                 505                 510 cag aag ctg gag tgc ctt cag gac cat ctg gat gac tta gtg gtg gag       1584
Gln Lys Leu Glu Cys Leu Gln Asp His Leu Asp Asp Leu Val Val Glu
        515                 520                 525 tgt aga gat ata gtt ggc aac ctc act gag tta gaa tca gag gat att       1632
Cys Arg Asp Ile Val Gly Asn Leu Thr Glu Leu Glu Ser Glu Asp Ile
    530                 535                 540 caa ata gaa gcc ttg ctg atg aga gcc tgt gag ccc ata att cag aac       1680
```

```
        Gln Ile Glu Ala Leu Leu Met Arg Ala Cys Glu Pro Ile Ile Gln Asn
        545                 550                 555                 560 ttc tgc cac gat gtg gca gat aac cag ata gac tcc ggg gac ctg atg             1728
Phe Cys His Asp Val Ala Asp Asn Gln Ile Asp Ser Gly Asp Leu Met
                565                 570                 575 gag tgt ctg ata cag aac aaa cac cag aag gac atg aac gag aag tgt             1776
Glu Cys Leu Ile Gln Asn Lys His Gln Lys Asp Met Asn Glu Lys Cys
            580                 585                 590 gcc atc gga gtt acc cac ttc cag ctg gtg cag atg aag gat ttt cgg             1824
Ala Ile Gly Val Thr His Phe Gln Leu Val Gln Met Lys Asp Phe Arg
        595                 600                 605 ttt tct tac aag ttt aaa atg gcc tgc aag gag gac gtg ttg aag ctt             1872
Phe Ser Tyr Lys Phe Lys Met Ala Cys Lys Glu Asp Val Leu Lys Leu
    610                 615                 620 tgc cca aac ata aaa aag aag gtg gac gtg gtg atc tgc ctg agc acg             1920
Cys Pro Asn Ile Lys Lys Lys Val Asp Val Val Ile Cys Leu Ser Thr
625                 630                 635                 640 acc gtg cgc aat gac act ctg cag gaa gcc aag gag cac agg gtg tcc             1968
Thr Val Arg Asn Asp Thr Leu Gln Glu Ala Lys Glu His Arg Val Ser
                645                 650                 655 ctg aag tgc cgc agg cag ctc cgt gtg gag gag ctg gag atg acg gag             2016
Leu Lys Cys Arg Arg Gln Leu Arg Val Glu Glu Leu Glu Met Thr Glu
            660                 665                 670 gac atc cgc ttg gag cca gat cta tac gaa gcc tgc aag agt gac atc             2064
Asp Ile Arg Leu Glu Pro Asp Leu Tyr Glu Ala Cys Lys Ser Asp Ile
        675                 680                 685 aaa aac ttc tgt tcc gct gtg caa tat ggc aac gct cag att atc gaa             2112
Lys Asn Phe Cys Ser Ala Val Gln Tyr Gly Asn Ala Gln Ile Ile Glu
    690                 695                 700 tgt ctg aaa gaa aac aag aag cag cta agc acc cgc tgc cac caa aaa             2160
Cys Leu Lys Glu Asn Lys Lys Gln Leu Ser Thr Arg Cys His Gln Lys
705                 710                 715                 720 gta ttt aag ctg cag gag aca gag atg atg gac cca gag cta gac tac             2208
Val Phe Lys Leu Gln Glu Thr Glu Met Met Asp Pro Glu Leu Asp Tyr
                725                 730                 735 acc ctc atg agg gtc tgc aag cag atg ata aag aag ttc tgt ccg gaa             2256
Thr Leu Met Arg Val Cys Lys Gln Met Ile Lys Lys Phe Cys Pro Glu
            740                 745                 750 gca gat tct aaa acc atg ttg cag tgc ttg aag caa aat aaa aac agt             2304
Ala Asp Ser Lys Thr Met Leu Gln Cys Leu Lys Gln Asn Lys Asn Ser
        755                 760                 765 gaa ttg atg gat ccc aaa tgc aaa cag atg ata acc aag cgc cag atc             2352
Glu Leu Met Asp Pro Lys Cys Lys Gln Met Ile Thr Lys Arg Gln Ile
    770                 775                 780 acc cag aac aca gat tac cgc tta aac ccc atg tta aga aaa gcc tgt             2400
Thr Gln Asn Thr Asp Tyr Arg Leu Asn Pro Met Leu Arg Lys Ala Cys
785                 790                 795                 800 aaa gct gac att cct aaa ttc tgt cac ggt atc ctg act aag gcc aag             2448
Lys Ala Asp Ile Pro Lys Phe Cys His Gly Ile Leu Thr Lys Ala Lys
                805                 810                 815 gat gat tca gaa tta gaa gga caa gtc atc tct tgc ctg aag ctg aga             2496
Asp Asp Ser Glu Leu Glu Gly Gln Val Ile Ser Cys Leu Lys Leu Arg
            820                 825                 830 tat gct gac cag cgc ctg tct tca gac tgt gaa gac cag atc cga atc             2544
Tyr Ala Asp Gln Arg Leu Ser Ser Asp Cys Glu Asp Gln Ile Arg Ile
        835                 840                 845 att atc cag gag tcc gcc ctg gac tac cgc ctg gat cct cag ctc cag             2592
Ile Ile Gln Glu Ser Ala Leu Asp Tyr Arg Leu Asp Pro Gln Leu Gln
    850                 855                 860
```

```
ctg cac tgc tca gac gag atc tcc agt cta tgt gct gaa gaa gca gca      2640
Leu His Cys Ser Asp Glu Ile Ser Ser Leu Cys Ala Glu Glu Ala Ala
865                 870                 875                 880 gcc caa gag cag aca ggt cag gtg gag gag tgc ctc aag gtc aac ctg      2688
Ala Gln Glu Gln Thr Gly Gln Val Glu Glu Cys Leu Lys Val Asn Leu
                885                 890                 895 ctc aag atc aaa aca gaa ttg tgt aaa aag gaa gtg cta aac atg ctg      2736
Leu Lys Ile Lys Thr Glu Leu Cys Lys Lys Glu Val Leu Asn Met Leu
            900                 905                 910 aag gaa agc aaa gca gac atc ttt gtt gac ccg gta ctt cat act gct      2784
Lys Glu Ser Lys Ala Asp Ile Phe Val Asp Pro Val Leu His Thr Ala
        915                 920                 925 tgt gcc ctg gac att aaa cac cac tgc gca gcc atc acc cct ggc cgc      2832
Cys Ala Leu Asp Ile Lys His His Cys Ala Ala Ile Thr Pro Gly Arg
    930                 935                 940 ggg cgt caa atg tcc tgt ctc atg gaa gca ctg gag gat aag cgg gtg      2880
Gly Arg Gln Met Ser Cys Leu Met Glu Ala Leu Glu Asp Lys Arg Val
945                 950                 955                 960 agg tta cag ccc gag tgc aaa aag cgc ctc aat gac cgg att gag atg      2928
Arg Leu Gln Pro Glu Cys Lys Lys Arg Leu Asn Asp Arg Ile Glu Met
                965                 970                 975 tgg agt tac gca gca aag gtg gcc cca gca gat ggc ttc tct gat ctt      2976
Trp Ser Tyr Ala Ala Lys Val Ala Pro Ala Asp Gly Phe Ser Asp Leu
            980                 985                 990 gcc atg caa gta atg acg tct cca tct aag aac tac att ctc tct gtg      3024
Ala Met Gln Val Met Thr Ser Pro Ser Lys Asn Tyr Ile Leu Ser Val
        995                 1000                1005 atc agt ggg agc atc tgt ata ttg ttc ctg att ggc ctg atg tgt gga      3072
Ile Ser Gly Ser Ile Cys Ile Leu Phe Leu Ile Gly Leu Met Cys Gly
    1010                1015                1020 cgg atc acc aag cga gtg aca cga gag ctc aag gac agg tag             3114
Arg Ile Thr Lys Arg Val Thr Arg Glu Leu Lys Asp Arg *
1025                1030                1035
```

<210> SEQ ID NO 6
<211> LENGTH: 1037
<212> TYPE: PRT
<213> ORGANISM: Homo sapiens

<400> SEQUENCE: 6

```
Asp Val Arg Glu Pro Glu Asn Glu Ile Ser Ser Asp Cys Asn His Leu
1               5                   10                  15

Leu Trp Asn Tyr Lys Leu Asn Leu Thr Thr Asp Pro Lys Phe Glu Ser
            20                  25                  30

Val Ala Arg Glu Val Cys Lys Ser Thr Ile Thr Glu Ile Glu Glu Cys
        35                  40                  45

Ala Asp Glu Pro Val Gly Lys Gly Tyr Met Val Ser Cys Leu Val Asp
    50                  55                  60

His Arg Gly Asn Ile Thr Glu Tyr Gln Cys His Gln Tyr Ile Thr Lys
65                  70                  75                  80

Met Thr Ala Ile Ile Phe Ser Asp Tyr Arg Leu Ile Cys Gly Phe Met
                85                  90                  95

Asp Asp Cys Lys Asn Asp Ile Asn Ile Leu Lys Cys Gly Ser Ile Arg
            100                 105                 110

Leu Gly Glu Lys Asp Ala His Ser Gln Gly Glu Val Val Ser Cys Leu
        115                 120                 125

Glu Lys Gly Leu Val Lys Glu Ala Glu Glu Arg Glu Pro Lys Ile Gln
    130                 135                 140
```

-continued

```
Val Ser Glu Leu Cys Lys Lys Ala Ile Leu Arg Val Ala Glu Leu Ser
145                 150                 155                 160

Ser Asp Asp Phe His Leu Asp Arg His Leu Tyr Phe Ala Cys Arg Asp
                165                 170                 175

Asp Arg Glu Arg Phe Cys Glu Asn Thr Gln Ala Gly Glu Gly Arg Val
            180                 185                 190

Tyr Lys Cys Leu Phe Asn His Lys Phe Glu Glu Ser Met Ser Glu Lys
        195                 200                 205

Cys Arg Glu Ala Leu Thr Thr Arg Gln Lys Leu Ile Ala Gln Asp Tyr
    210                 215                 220

Lys Val Ser Tyr Ser Leu Ala Lys Ser Cys Lys Ser Asp Leu Lys Lys
225                 230                 235                 240

Tyr Arg Cys Asn Val Glu Asn Leu Pro Arg Ser Arg Glu Ala Arg Leu
                245                 250                 255

Ser Tyr Leu Leu Met Cys Leu Glu Ser Ala Val His Arg Gly Arg Gln
            260                 265                 270

Val Ser Ser Glu Cys Gln Gly Glu Met Leu Asp Tyr Arg Arg Met Leu
        275                 280                 285

Met Glu Asp Phe Ser Leu Ser Pro Glu Ile Ile Leu Ser Cys Arg Gly
    290                 295                 300

Glu Ile Glu His His Cys Ser Gly Leu His Arg Lys Gly Arg Thr Leu
305                 310                 315                 320

His Cys Leu Met Lys Val Val Arg Gly Glu Lys Gly Asn Leu Gly Met
                325                 330                 335

Asn Cys Gln Gln Ala Leu Gln Thr Leu Ile Gln Glu Thr Asp Pro Gly
            340                 345                 350

Ala Asp Tyr Arg Ile Asp Arg Ala Leu Asn Glu Ala Cys Glu Ser Val
        355                 360                 365

Ile Gln Thr Ala Cys Lys His Ile Arg Ser Gly Asp Pro Met Ile Leu
370                 375                 380

Ser Cys Leu Met Glu His Leu Tyr Thr Glu Lys Met Val Glu Asp Cys
385                 390                 395                 400

Glu His Arg Leu Leu Glu Leu Gln Tyr Phe Ile Ser Arg Asp Trp Lys
                405                 410                 415

Leu Asp Pro Val Leu Tyr Arg Lys Cys Gln Gly Asp Ala Ser Arg Leu
            420                 425                 430

Cys His Thr His Gly Trp Asn Glu Thr Ser Glu Phe Met Pro Gln Gly
        435                 440                 445

Ala Val Phe Ser Cys Leu Tyr Arg His Ala Tyr Arg Thr Glu Glu Gln
    450                 455                 460

Gly Arg Arg Leu Ser Arg Glu Cys Arg Ala Glu Val Gln Arg Ile Leu
465                 470                 475                 480

His Gln Arg Ala Met Asp Val Lys Leu Asp Pro Ala Leu Gln Asp Lys
                485                 490                 495

Cys Leu Ile Asp Leu Gly Lys Trp Cys Ser Glu Lys Thr Glu Thr Gly
            500                 505                 510

Gln Lys Leu Glu Cys Leu Gln Asp His Leu Asp Asp Leu Val Val Glu
        515                 520                 525

Cys Arg Asp Ile Val Gly Asn Leu Thr Glu Leu Glu Ser Glu Asp Ile
    530                 535                 540

Gln Ile Glu Ala Leu Leu Met Arg Ala Cys Glu Pro Ile Ile Gln Asn
545                 550                 555                 560

Phe Cys His Asp Val Ala Asp Asn Gln Ile Asp Ser Gly Asp Leu Met
```

-continued

```
                565                 570                 575
Glu Cys Leu Ile Gln Asn Lys His Gln Lys Asp Met Asn Glu Lys Cys
            580                 585                 590

Ala Ile Gly Val Thr His Phe Gln Leu Val Gln Met Lys Asp Phe Arg
            595                 600                 605

Phe Ser Tyr Lys Phe Lys Met Ala Cys Lys Glu Asp Val Leu Lys Leu
            610                 615                 620

Cys Pro Asn Ile Lys Lys Val Asp Val Ile Cys Leu Ser Thr
625                 630                 635                 640

Thr Val Arg Asn Asp Thr Leu Gln Glu Ala Lys Glu His Arg Val Ser
            645                 650                 655

Leu Lys Cys Arg Arg Gln Leu Arg Val Glu Glu Leu Glu Met Thr Glu
            660                 665                 670

Asp Ile Arg Leu Glu Pro Asp Leu Tyr Glu Ala Cys Lys Ser Asp Ile
            675                 680                 685

Lys Asn Phe Cys Ser Ala Val Gln Tyr Gly Asn Ala Gln Ile Ile Glu
            690                 695                 700

Cys Leu Lys Glu Asn Lys Lys Gln Leu Ser Thr Arg Cys His Gln Lys
705                 710                 715                 720

Val Phe Lys Leu Gln Glu Thr Glu Met Met Asp Pro Glu Leu Asp Tyr
            725                 730                 735

Thr Leu Met Arg Val Cys Lys Gln Met Ile Lys Lys Phe Cys Pro Glu
            740                 745                 750

Ala Asp Ser Lys Thr Met Leu Gln Cys Leu Lys Gln Asn Lys Asn Ser
            755                 760                 765

Glu Leu Met Asp Pro Lys Cys Lys Gln Met Ile Thr Lys Arg Gln Ile
            770                 775                 780

Thr Gln Asn Thr Asp Tyr Arg Leu Asn Pro Met Leu Arg Lys Ala Cys
785                 790                 795                 800

Lys Ala Asp Ile Pro Lys Phe Cys His Gly Ile Leu Thr Lys Ala Lys
            805                 810                 815

Asp Asp Ser Glu Leu Glu Gly Gln Val Ile Ser Cys Leu Lys Leu Arg
            820                 825                 830

Tyr Ala Asp Gln Arg Leu Ser Ser Asp Cys Glu Asp Gln Ile Arg Ile
            835                 840                 845

Ile Ile Gln Glu Ser Ala Leu Asp Tyr Arg Leu Asp Pro Gln Leu Gln
            850                 855                 860

Leu His Cys Ser Asp Glu Ile Ser Ser Leu Cys Ala Glu Glu Ala Ala
865                 870                 875                 880

Ala Gln Glu Gln Thr Gly Gln Val Glu Glu Cys Leu Lys Val Asn Leu
            885                 890                 895

Leu Lys Ile Lys Thr Glu Leu Cys Lys Lys Glu Val Leu Asn Met Leu
            900                 905                 910

Lys Glu Ser Lys Ala Asp Ile Phe Val Asp Pro Val Leu His Thr Ala
            915                 920                 925

Cys Ala Leu Asp Ile Lys His His Cys Ala Ala Ile Thr Pro Gly Arg
            930                 935                 940

Gly Arg Gln Met Ser Cys Leu Met Glu Ala Leu Glu Asp Lys Arg Val
945                 950                 955                 960

Arg Leu Gln Pro Glu Cys Lys Lys Arg Leu Asn Asp Arg Ile Glu Met
            965                 970                 975

Trp Ser Tyr Ala Ala Lys Val Ala Pro Ala Asp Gly Phe Ser Asp Leu
            980                 985                 990
```

```
Ala Met Gln Val Met Thr Ser Pro Ser Lys Asn Tyr Ile Leu Ser Val
        995                 1000                1005

Ile Ser Gly Ser Ile Cys Ile Leu Phe Leu Ile Gly Leu Met Cys Gly
        1010                1015                1020

Arg Ile Thr Lys Arg Val Thr Arg Glu Leu Lys Asp Arg
1025                1030                1035

<210> SEQ ID NO 7
<211> LENGTH: 1177
<212> TYPE: PRT
<213> ORGANISM: Homo sapiens

<400> SEQUENCE: 7

Met Ala Ala Cys Gly Arg Val Arg Arg Met Phe Arg Leu Ser Ala Ala
  1               5                  10                  15

Leu His Leu Leu Leu Leu Phe Ala Ala Gly Gly Arg Asn Ser Pro Ala
             20                  25                  30

Arg Ala Ser His Ser Gln Gly Gln Gly Pro Gly Ala Asn Phe Val Ser
         35                  40                  45

Phe Val Gly Gln Ala Gly Gly Gly Pro Ala Gly Gln Gln Leu Pro
     50                  55                  60

Gln Leu Pro Gln Ser Ser Gln Leu Gln Gln Gln Gln Gln Gln Gln Gln
 65                  70                  75                  80

Gln Gln Gln Gln Pro Gln Pro Pro Gln Pro Pro Phe Pro Ala Gly Gly
                 85                  90                  95

Pro Pro Arg Arg Gly Gly Ala Gly Ala Gly Gly Gly Trp Lys Leu Ala
            100                 105                 110

Glu Glu Glu Ser Cys Arg Glu Asp Val Thr Arg Val Cys Pro Lys His
            115                 120                 125

Thr Trp Ser Asn Asn Leu Ala Val Leu Glu Cys Leu Gln Asp Val Arg
        130                 135                 140

Glu Pro Glu Asn Glu Ile Ser Ser Asp Cys Asn His Leu Leu Trp Asn
145                 150                 155                 160

Tyr Lys Leu Asn Leu Thr Thr Asp Pro Lys Phe Glu Ser Val Ala Arg
                165                 170                 175

Glu Val Cys Lys Ser Thr Ile Thr Glu Ile Lys Glu Cys Ala Asp Glu
            180                 185                 190

Pro Val Gly Lys Gly Tyr Met Val Ser Cys Leu Val Asp His Arg Gly
            195                 200                 205

Asn Ile Thr Glu Tyr Gln Cys His Gln Tyr Ile Thr Lys Met Thr Ala
        210                 215                 220

Ile Ile Phe Ser Asp Tyr Arg Leu Ile Cys Gly Phe Met Asp Asp Cys
225                 230                 235                 240

Lys Asn Asp Ile Asn Ile Leu Lys Cys Gly Ser Ile Arg Leu Gly Glu
                245                 250                 255

Lys Asp Ala His Ser Gln Gly Glu Val Val Ser Cys Leu Glu Lys Gly
            260                 265                 270

Leu Val Lys Glu Ala Glu Arg Glu Pro Lys Ile Gln Val Ser Glu
            275                 280                 285

Leu Cys Lys Lys Ala Ile Leu Arg Val Ala Glu Leu Ser Ser Asp Asp
        290                 295                 300

Phe His Leu Asp Arg His Leu Tyr Phe Ala Cys Arg Asp Asp Arg Glu
305                 310                 315                 320

Arg Phe Cys Glu Asn Thr Gln Ala Cys Glu Gly Arg Val Tyr Lys Cys
```

-continued

```
                325                 330                 335
Leu Phe Asn His Lys Phe Glu Glu Ser Met Ser Glu Lys Cys Arg Glu
            340                 345                 350

Ala Leu Thr Thr Arg Gln Lys Leu Ile Ala Gln Asp Tyr Lys Val Ser
            355                 360                 365

Tyr Ser Leu Ala Lys Ser Cys Lys Ser Asp Leu Lys Lys Tyr Arg Cys
        370                 375                 380

Asn Val Glu Asn Leu Pro Arg Ser Arg Glu Ala Arg Leu Ser Tyr Leu
385                 390                 395                 400

Leu Met Cys Leu Glu Ser Ala Val His Arg Gly Arg Gln Val Ser Ser
                405                 410                 415

Glu Cys Gln Gly Glu Met Leu Asp Tyr Arg Arg Met Leu Met Glu Asp
            420                 425                 430

Phe Ser Leu Ser Pro Glu Ile Ile Leu Ser Cys Arg Gly Glu Ile Glu
        435                 440                 445

His His Cys Ser Gly Leu His Arg Lys Gly Arg Thr Leu His Cys Leu
    450                 455                 460

Met Lys Val Val Arg Gly Glu Lys Cys Asn Leu Gly Met Asn Cys Gln
465                 470                 475                 480

Gln Ala Leu Gln Thr Leu Ile Gln Glu Thr Asp Pro Gly Ala Asp Tyr
                485                 490                 495

Arg Ile Asp Arg Ala Leu Asn Glu Ala Cys Glu Ser Val Ile Gln Thr
            500                 505                 510

Ala Cys Lys His Ile Arg Ser Gly Asp Pro Met Ile Ser Ser Cys Leu
        515                 520                 525

Met Glu His Leu Tyr Thr Glu Lys Met Val Glu Asp Cys Glu His Arg
    530                 535                 540

Leu Leu Glu Leu Gln Tyr Phe Ile Ser Arg Asp Trp Lys Leu Asp Pro
545                 550                 555                 560

Val Leu Tyr Arg Lys Cys Gln Gly Asp Ala Ser Arg Leu Cys His Thr
                565                 570                 575

His Gly Trp Asn Glu Thr Ser Glu Phe Met Pro Gln Gly Ala Val Phe
            580                 585                 590

Ser Cys Leu Tyr Arg Glu Ala Tyr Arg Thr Glu Glu Gln Gly Arg Arg
        595                 600                 605

Leu Ser Arg Glu Cys Arg Ala Glu Val Gln Arg Ile Leu His Gln Arg
    610                 615                 620

Ala Met Asp Val Lys Leu Asp Pro Ala Leu Gln Asp Lys Cys Leu Ile
625                 630                 635                 640

Asp Leu Gly Lys Trp Cys Ser Glu Lys Thr Glu Thr Gly Gln Glu Leu
                645                 650                 655

Glu Cys Leu Gln Asp His Leu Asp Asp Leu Val Val Glu Cys Arg Asp
            660                 665                 670

Ile Val Gly Asn Leu Thr Glu Leu Glu Ser Glu Asp Ile Gln Ile Glu
        675                 680                 685

Ala Leu Leu Met Arg Ala Cys Glu Pro Ile Ile Gln Thr Phe Cys His
    690                 695                 700

Asp Ala Asp Asn Gln Ile Asp Ser Gly Asp Leu Met Glu Cys Leu Ile
705                 710                 715                 720

Gln Asn Lys His Gln Lys Asp Met Asn Glu Lys Cys Ala Ile Gly Val
                725                 730                 735

Thr His Phe Gln Leu Val Gln Met Lys Asp Phe Arg Phe Ser Tyr Lys
            740                 745                 750
```

```
Phe Lys Met Ala Cys Lys Glu Asp Val Leu Lys Leu Cys Pro Asn Ile
            755                 760                 765
Lys Lys Lys Val Asp Val Ile Cys Leu Ser Thr Thr Val Arg Asn
    770                 775                 780
Asp Thr Leu Gln Glu Ala Lys Glu His Arg Val Ser Leu Lys Cys Arg
785                 790                 795                 800
Arg Gln Leu Arg Val Glu Glu Leu Glu Met Thr Glu Asp Ile Arg Leu
                805                 810                 815
Glu Pro Asp Leu Tyr Glu Ala Cys Lys Ser Asp Ile Lys Asn Phe Cys
            820                 825                 830
Ser Ala Val Gln Tyr Gly Asn Ala Gln Ile Ile Glu Cys Leu Lys Glu
            835                 840                 845
Asn Lys Lys Gln Leu Ser Thr Arg Cys His Gln Lys Val Phe Lys Leu
850                 855                 860
Gln Glu Thr Glu Met Met Asp Pro Glu Leu Asp Tyr Thr Leu Met Arg
865                 870                 875                 880
Val Cys Lys Gln Met Ile Lys Arg Phe Cys Pro Glu Ala Asp Ser Lys
                885                 890                 895
Thr Met Leu Gln Cys Leu Lys Gln Asn Lys Asn Ser Glu Leu Met Asp
            900                 905                 910
Pro Lys Cys Lys Gln Met Ile Thr Lys Arg Gln Ile Thr Gln Asn Thr
            915                 920                 925
Asp Tyr Arg Leu Asn Pro Met Leu Arg Lys Ala Cys Lys Ala Asp Ile
930                 935                 940
Pro Lys Phe Cys His Gly Ile Leu Thr Lys Ala Lys Asp Asp Ser Glu
945                 950                 955                 960
Leu Glu Gly Gln Val Ile Ser Cys Leu Lys Leu Arg Tyr Ala Asp Gln
                965                 970                 975
Arg Leu Ser Ser Asp Cys Glu Asp Gln Ile Arg Ile Ile Gln Glu
            980                 985                 990
Ser Ala Leu Asp Tyr Arg Leu Asp Pro Gln Leu Gln Leu His Cys Ser
            995                 1000                1005
Asp Glu Ile Ser Ser Leu Cys Ala Glu Glu Ala Ala Gln Glu Gln
    1010                1015                1020
Thr Gly Gln Val Glu Glu Cys Leu Lys Val Asn Leu Leu Lys Ile Lys
1025                1030                1035                1040
Thr Glu Leu Cys Lys Lys Glu Val Leu Asn Met Leu Lys Glu Ser Lys
                1045                1050                1055
Ala Asp Ile Phe Val Asp Pro Val Leu His Thr Ala Cys Ala Leu Asp
            1060                1065                1070
Ile Lys His His Cys Ala Ala Leu Thr Pro Gly Arg Gly Arg Gln Met
    1075                1080                1085
Ser Cys Leu Met Glu Ala Leu Glu Asp Lys Arg Val Arg Leu Gln Pro
    1090                1095                1100
Glu Cys Lys Lys Arg Leu Asn Asp Arg Ile Glu Met Trp Ser Tyr Ala
1105                1110                1115                1120
Ala Lys Val Ala Pro Ala Asp Gly Phe Ser Asp Leu Ala Met Gln Val
                1125                1130                1135
Met Thr Ser Pro Ser Lys Asn Tyr Ile Leu Ser Val Ile Ser Gly Ser
            1140                1145                1150
Ile Cys Ile Leu Phe Leu Ile Gly Leu Met Cys Gly Arg Ile Thr Lys
    1155                1160                1165
```

```
Arg Val Thr Arg Glu Leu Lys Asp Arg
    1170                1175
```

<210> SEQ ID NO 8
<211> LENGTH: 1179
<212> TYPE: PRT
<213> ORGANISM: Homo sapiens

<400> SEQUENCE: 8

```
Met Ala Ala Cys Gly Arg Val Arg Arg Met Phe Arg Leu Ser Ala Ala
 1               5                  10                  15

Leu His Leu Leu Leu Phe Ala Ala Gly Ala Glu Lys Leu Pro Gly
             20                  25                  30

His Gly Val His Ser Gln Gly Gln Gly Pro Gly Ala Asn Phe Val Ser
             35                  40                  45

Phe Val Gly Gln Ala Gly Gly Gly Pro Ala Gly Gln Gln Leu Pro
    50                  55                  60

Gln Leu Leu Gln Ser Ser Gln Leu Gln Gln Gln Gln Gln Gln Gln
65                   70                  75                  80

Gln Gln Gln Gln Leu Gln Pro Pro Gln Pro Pro Phe Pro Ala Gly Gly
                 85                  90                  95

Pro Pro Ala Arg Arg Gly Gly Ala Gly Ala Gly Gly Gly Trp Lys Leu
            100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
            130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Glu Ile Lys Glu Cys Ala Asp
                180                 185                 190

Glu Pro Val Gly Lys Gly Tyr Met Val Ser Cys Leu Val Asp His Arg
            195                 200                 205

Gly Asn Ile Thr Glu Tyr Gln Cys His Gln Tyr Ile Thr Lys Met Thr
            210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Arg Glu Pro Lys Ile Gln Val Ser
            275                 280                 285

Glu Leu Cys Lys Lys Ala Ile Leu Arg Val Ala Glu Leu Ser Ser Asp
    290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Arg Glu Gly Arg Val Tyr Lys
                325                 330                 335

Cys Leu Phe Asn His Lys Phe Glu Glu Ser Met Ser Glu Lys Cys Arg
                340                 345                 350

Glu Ala Leu Thr Thr Arg Gln Lys Leu Ile Ala Gln Asp Tyr Lys Val
            355                 360                 365
```

-continued

```
Ser Tyr Ser Leu Ala Lys Ser Cys Lys Ser Asp Leu Lys Lys Tyr Arg
    370                 375                 380
Cys Asn Val Glu Asn Leu Pro Arg Ser Arg Glu Ala Arg Leu Ser Tyr
385                 390                 395                 400
Leu Leu Met Cys Leu Glu Ser Ala Val His Arg Gly Arg Gln Val Ser
                405                 410                 415
Ser Glu Cys Gln Gly Glu Met Leu Asp Tyr Arg Arg Met Leu Met Glu
            420                 425                 430
Asp Phe Ser Leu Ser Pro Glu Ile Ile Leu Ser Cys Arg Gly Glu Ile
        435                 440                 445
Glu His His Cys Ser Gly Leu His Arg Lys Gly Arg Thr Leu His Cys
    450                 455                 460
Leu Met Lys Val Val Arg Gly Glu Lys Gly Asn Leu Gly Met Asn Cys
465                 470                 475                 480
Gln Gln Ala Leu Gln Thr Leu Ile Gln Glu Thr Asp Pro Gly Ala Asp
                485                 490                 495
Tyr Arg Ile Asp Arg Ala Leu Asn Glu Ala Cys Glu Ser Val Ile Gln
            500                 505                 510
Thr Ala Cys Lys His Ile Arg Ser Gly Asp Pro Met Ile Leu Ser Cys
        515                 520                 525
Leu Met Glu His Leu Tyr Thr Glu Lys Met Val Glu Asp Cys Glu His
    530                 535                 540
Arg Leu Leu Glu Leu Gln Tyr Phe Ile Ser Arg Asp Trp Lys Leu Asp
545                 550                 555                 560
Pro Val Leu Tyr Arg Lys Cys Gln Gly Asp Ala Ser Arg Leu Cys His
                565                 570                 575
Thr His Gly Trp Asn Glu Thr Ser Glu Phe Met Pro Gln Gly Ala Val
            580                 585                 590
Phe Ser Cys Leu Tyr Arg His Ala Tyr Arg Thr Glu Glu Gln Gly Arg
        595                 600                 605
Arg Leu Leu Asp Pro Ala Leu Gln Asp Lys Cys Leu Ile Asp Leu Gly
    610                 615                 620
Lys Trp Cys Ser Glu Lys Thr Glu Thr Gly Gln Glu Leu Glu Cys Leu
625                 630                 635                 640
Ser Arg Glu Cys Arg Ala Glu Val Gln Arg Ile Leu His Gln Arg Ala
                645                 650                 655
Met Asp Val Lys Gln Asp His Leu Asp Asp Leu Val Val Glu Cys Arg
            660                 665                 670
Asp Ile Val Gly Asn Leu Thr Glu Leu Glu Ser Glu Asp Ile Gln Ile
        675                 680                 685
Glu Ala Leu Leu Met Arg Ala Cys Glu Pro Ile Ile Gln Asn Phe Cys
    690                 695                 700
His Asp Val Ala Asp Asn Gln Ile Asp Ser Gly Asp Leu Met Glu Cys
705                 710                 715                 720
Leu Ile Gln Asn Lys His Gln Lys Asp Met Asn Glu Lys Cys Ala Ile
                725                 730                 735
Gly Val Thr His Phe Gln Leu Val Gln Met Lys Asp Phe Arg Phe Ser
            740                 745                 750
Tyr Lys Phe Lys Met Ala Cys Lys Glu Asp Val Leu Lys Leu Cys Pro
        755                 760                 765
Asn Ile Lys Lys Lys Val Asp Val Val Ile Cys Leu Ser Thr Thr Val
    770                 775                 780
```

-continued

```
Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
            805                 810                 815

Arg Leu Glu Pro Asp Leu Tyr Glu Ala Cys Lys Ser Asp Ile Lys Asn
        820                 825                 830

Phe Cys Ser Ala Val Gln Tyr Gly Asn Ala Gln Ile Ile Glu Cys Leu
    835                 840                 845

Lys Glu Asn Lys Lys Gln Leu Ser Thr Arg Cys His Gln Lys Val Phe
850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
            885                 890                 895

Ser Lys Thr Met Leu Gln Cys Leu Lys Gln Asn Lys Asn Ser Glu Leu
        900                 905                 910

Met Asp Pro Lys Cys Lys Gln Met Ile Thr Lys Arg Gln Ile Thr Gln
    915                 920                 925

Asn Thr Asp Tyr Arg Leu Asn Pro Met Leu Arg Lys Ala Cys Lys Ala
930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
            965                 970                 975

Asp Gln Arg Leu Ser Ser Asp Cys Glu Asp Gln Ile Arg Ile Ile Ile
        980                 985                 990

Gln Glu Ser Ala Leu Asp Tyr Arg Leu Asp Pro Gln Leu Gln Leu His
    995                 1000                1005

Cys Ser Asp Glu Ile Ser Ser Leu Cys Ala Glu Glu Ala Ala Gln
    1010                1015                1020

Glu Gln Thr Gly Gln Val Glu Glu Cys Leu Lys Val Asn Leu Leu Lys
1025                1030                1035                1040

Ile Lys Thr Glu Leu Cys Lys Lys Glu Val Leu Asn Met Leu Lys Glu
            1045                1050                1055

Ser Lys Ala Asp Ile Phe Val Asp Pro Val Leu His Thr Ala Cys Ala
        1060                1065                1070

Leu Asp Ile Lys His His Cys Ala Ala Ile Thr Pro Gly Arg Gly Arg
    1075                1080                1085

Gln Met Ser Cys Leu Met Glu Ala Leu Glu Asp Lys Arg Val Arg Leu
    1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
            1125                1130                1135

Gln Val Met Thr Ser Pro Ser Lys Asn Tyr Ile Leu Ser Val Ile Ser
        1140                1145                1150

Gly Ser Ile Cys Ile Leu Phe Leu Ile Gly Leu Met Cys Gly Arg Ile
    1155                1160                1165

Thr Lys Arg Val Thr Arg Glu Leu Lys Asp Arg
    1170                1175

<210> SEQ ID NO 9
<211> LENGTH: 22
<212> TYPE: DNA
```

```
<213> ORGANISM: Artificial Sequence
<220> FEATURE:
<223> OTHER INFORMATION: Primer

<400> SEQUENCE: 9
gcttggagaa aggcctggtg aa                                              22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
tggcacttgc ggtacaggac ag                                              22

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gcagcttcag cagcaacagc a                                               21

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
cagctcagcc acccggagaa tg                                              22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
gcttggagaa aggcctggtg aa                                              22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
tggcacttgc ggtacaggac ag                                              22

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
gaacaccgtc tcttagagct gc                                              22
```

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gcttcctgca gagtgtcatt gc                                              22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
ggaggacgtg ttgaagcttt gc                                              22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ccagggcaca agcagtatga ag                                              22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
caacagcaga caggtcaggt gg                                              22

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ccggaagttc tgttggtatg ag                                              22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
atttaaccct cactaaaggg                                                 20

<210> SEQ ID NO 22
<211> LENGTH: 22
<212> TYPE: DNA
<213> ORGANISM: Artificial Sequence
<220> FEATURE:

-continued

<223> OTHER INFORMATION: Primer

<400> SEQUENCE: 22
gtaatacgac tcactatagg gc                                            22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ccggaagttc tgttggtatg ag                                            22

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gtggaaggac tcatgaccac agtc                                          24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
catgtgggcc atgaggtcca ccac                                          24

<210> SEQ ID NO 26
<211> LENGTH: 312
<212> TYPE: DNA
<213> ORGANISM: Homo sapiens
<220> FEATURE:
<221> NAME/KEY: CDS
<222> LOCATION: (1)...(312)
<223> OTHER INFORMATION:

<400> SEQUENCE: 26

```
agg tcc ctg aga ctc tcc tgt gca gcc tct gga ttc acc ttc agt agc      48
Arg Ser Leu Arg Leu Ser Cys Ala Ala Ser Gly Phe Thr Phe Ser Ser
 1               5                  10                  15 tat ggc atg cac tgg gtc cgc cag gct cca ggc aag ggg ctg gag tgg      96
Tyr Gly Met His Trp Val Arg Gln Ala Pro Gly Lys Gly Leu Glu Trp
             20                  25                  30 gtg gca gtt ata tca tat gat gga agt aat aaa tac tat gca gac tcc     144
Val Ala Val Ile Ser Tyr Asp Gly Ser Asn Lys Tyr Tyr Ala Asp Ser
         35                  40                  45 gtg aag ggc cga ttc acc atc tcc aga gac aat tcc aag aac acg ctg     192
Val Lys Gly Arg Phe Thr Ile Ser Arg Asp Asn Ser Lys Asn Thr Leu
     50                  55                  60 tat ctg caa atg aac agc ctg aga gct gag gac acg gct gtg tat tac     240
Tyr Leu Gln Met Asn Ser Leu Arg Ala Glu Asp Thr Ala Val Tyr Tyr
 65                  70                  75                  80 tgt gcg agg tcg act acg agg tct tat cct cta tac ggt atg gac gtt     288
Cys Ala Arg Ser Thr Thr Arg Ser Tyr Pro Leu Tyr Gly Met Asp Val
                 85                  90                  95 tgg ggc caa ggg aac cct gtc acc                                     312
Trp Gly Gln Gly Asn Pro Val Thr
```

<210> SEQ ID NO 27
<211> LENGTH: 399
<212> TYPE: DNA
<213> ORGANISM: Homo sapiens
<220> FEATURE:
<221> NAME/KEY: CDS
<222> LOCATION: (1)...(399)
<223> OTHER INFORMATION:

<400> SEQUENCE: 27

| | | | | | | | | | | | | | | | | |
|---|---|---|---|---|---|---|---|---|---|---|---|---|---|---|---|---|
| gtg | acc | tcc | tat | gtg | ctg | act | cag | cca | ccc | tcg | gtg | tca | gtg | gcc | cca | 48 |
| Val | Thr | Ser | Tyr | Val | Leu | Thr | Gln | Pro | Pro | Ser | Val | Ser | Val | Ala | Pro | |
| 1 | | | | 5 | | | | | 10 | | | | | 15 | | |
| gga | cag | acg | gcc | agt | att | acc | tgt | ggg | gga | aat | aac | att | gga | agt | aaa | 96 |
| Gly | Gln | Thr | Ala | Ser | Ile | Thr | Cys | Gly | Gly | Asn | Asn | Ile | Gly | Ser | Lys | |
| | | | 20 | | | | | 25 | | | | | 30 | | | |
| agt | gtg | cac | tgg | tac | cat | cag | aag | cca | ggc | cag | gcc | cct | gtg | ctg | gtc | 144 |
| Ser | Val | His | Trp | Tyr | His | Gln | Lys | Pro | Gly | Gln | Ala | Pro | Val | Leu | Val | |
| | | | 35 | | | | | 40 | | | | | 45 | | | |
| gtc | tat | gat | gat | agc | gac | cgg | ccc | tca | ggg | atc | cct | gag | cga | ttc | tct | 192 |
| Val | Tyr | Asp | Asp | Ser | Asp | Arg | Pro | Ser | Gly | Ile | Pro | Glu | Arg | Phe | Ser | |
| | 50 | | | | | 55 | | | | | 60 | | | | | |
| ggc | tcc | aac | tct | ggg | aac | acg | gcc | acc | ctg | acc | atc | acc | agg | gtc | gaa | 240 |
| Gly | Ser | Asn | Ser | Gly | Asn | Thr | Ala | Thr | Leu | Thr | Ile | Thr | Arg | Val | Glu | |
| 65 | | | | | 70 | | | | | 75 | | | | | 80 | |
| gcc | ggg | gat | gag | gcc | gac | tat | tac | tgt | cag | gtg | tgg | gat | agt | agt | agt | 288 |
| Ala | Gly | Asp | Glu | Ala | Asp | Tyr | Tyr | Cys | Gln | Val | Trp | Asp | Ser | Ser | Ser | |
| | | | | 85 | | | | | 90 | | | | | 95 | | |
| gat | ctc | aat | tgg | gtg | ttc | ggc | gga | agg | acc | caa | gct | gac | cgt | cct | acg | 336 |
| Asp | Leu | Asn | Trp | Val | Phe | Gly | Gly | Arg | Thr | Gln | Ala | Asp | Arg | Pro | Thr | |
| | | | | 100 | | | | | 105 | | | | | 110 | | |
| tca | gcc | caa | ggc | tgc | ccc | tcc | ggt | cac | tct | gtt | ccc | cgc | ccc | cct | ctg | 384 |
| Ser | Ala | Gln | Gly | Cys | Pro | Ser | Gly | His | Ser | Val | Pro | Arg | Pro | Pro | Leu | |
| | | | 115 | | | | | 120 | | | | | 125 | | | |
| aag | agc | ttc | aag | ctt | | | | | | | | | | | | 399 |
| Lys | Ser | Phe | Lys | Leu | | | | | | | | | | | | |
| | | | 130 | | | | | | | | | | | | | |

<210> SEQ ID NO 28
<211> LENGTH: 104
<212> TYPE: PRT
<213> ORGANISM: Homo sapiens

<400> SEQUENCE: 28

Arg Ser Leu Arg Leu Ser Cys Ala Ala Ser Gly Phe Thr Phe Ser Ser
1               5                   10                  15

Tyr Gly Met His Trp Val Arg Gln Ala Pro Gly Lys Gly Leu Glu Trp
            20                  25                  30

Val Ala Val Ile Ser Tyr Asp Gly Ser Asn Lys Tyr Tyr Ala Asp Ser
        35                  40                  45

Val Lys Gly Arg Phe Thr Ile Ser Arg Asp Asn Ser Lys Asn Thr Leu
    50                  55                  60

Tyr Leu Gln Met Asn Ser Leu Arg Ala Glu Asp Thr Ala Val Tyr Tyr
65                  70                  75                  80

Cys Ala Arg Ser Thr Thr Arg Ser Tyr Pro Leu Tyr Gly Met Asp Val
                85                  90                  95

Trp Gly Gln Gly Asn Pro Val Thr
            100

```
<210> SEQ ID NO 29
<211> LENGTH: 133
<212> TYPE: PRT
<213> ORGANISM: Homo sapiens

<400> SEQUENCE: 29

Val Thr Ser Tyr Val Leu Thr Gln Pro Pro Ser Val Ser Val Ala Pro
 1               5                  10                  15

Gly Gln Thr Ala Ser Ile Thr Cys Gly Gly Asn Asn Ile Gly Ser Lys
            20                  25                  30

Ser Val His Trp Tyr His Gln Lys Pro Gly Gln Ala Pro Val Leu Val
        35                  40                  45

Val Tyr Asp Asp Ser Asp Arg Pro Ser Gly Ile Pro Glu Arg Phe Ser
    50                  55                  60

Gly Ser Asn Ser Gly Asn Thr Ala Thr Leu Thr Ile Thr Arg Val Glu
65                  70                  75                  80

Ala Gly Asp Glu Ala Asp Tyr Tyr Cys Gln Val Trp Asp Ser Ser Ser
                85                  90                  95

Asp Leu Asn Trp Val Phe Gly Gly Arg Thr Gln Ala Asp Arg Pro Thr
            100                 105                 110

Ser Ala Gln Gly Cys Pro Ser Gly His Ser Val Pro Arg Pro Pro Leu
        115                 120                 125

Lys Ser Phe Lys Leu
        130

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
caagagcaga caggtcaggt gg                                           22
```

NEOPLASM-SPECIFIC POLYPEPTIDES AND THEIR USES

CROSS REFERENCE TO RELATED APPLICATIONS

This application is a continuation-in-part of international application number PCT/DE02/02699, filed Jul. 23, 2002, which, in turn, claims the benefit of German application numbers DE 101 36 009.6, filed Jul. 24, 2001, and DE 102 10 425.5, filed Mar. 9, 2002, the disclosures of which are hereby incorporated by reference.

BACKGROUND OF THE INVENTION

The present invention is related to the field of cancer diagnosis and treatment and, more specifically, to polypeptides and methods of using these polypeptides in the diagnosis, detection, monitoring, and treatment of neoplasms in a mammal, e.g., a human.

In the United States well over one million individuals are diagnosed with cancer each year. Although recent advances in the medical field have significantly improved the rate of survival among cancer patients, a large number of cancer-related deaths still could be prevented by the early diagnosis of the tumor. Accordingly, at the time of initial diagnosis, an alarming number of patients have already reached late stages of the disease. Clearly, there is a need for the early and improved detection and treatment of neoplasms (e.g., stomach adenocarcinoma, colorectal adenocarcinoma, lung adenocarcinoma, adenocarcinoma of the pancreas), as this would increase the chance of treating the neoplasm and, thereby, lead to an improved prognosis for long-term survival.

Human monoclonal antibodies produced from B-cell hybridomas may be used in the treatment of tumors, viral and microbial infections, B-cell immunodeficiencies with reduced antibody production, and other impairments of the immune system. Gastric carcinoma is one of the most frequently occurring types of cancer worldwide and is histologically divided into diffuse adenocarcinoma and intestinal adenocarcinoma. Intestinal gastric carcinomas are often accompanied by chronic type B gastritis and particularly by intestinal metaplasias, which are considered to be precursors of dysplastic changes and of gastric carcinomas. Differences between these two types of gastric carcinomas are also evident in that patients having carcinomas of the diffuse type often belong to blood group A, from which the influence of genetic factors on the cancer risk may be concluded, while environmental factors, e.g., a *Helicobacter pylori* infection, is possibly significant for the occurrence of carcinomas of the intestinal type.

The development of stomach cancer is a multi-step and multi-factor process (Correa, Cancer Res. 52:6735-6740 (1992)). Although little is known about molecular mechanisms, factors such as high salt intake, alcohol, nitrosamines, and infection with the bacterium *Helicobacter pylori* (*H. pylori*) are clearly proven to be involved in the initiation of stomach carcinogenesis. Due to a strong correlation between *H. pylori* infection and the occurrence of gastritis, dysplasia, and development of gastric cancer, the bacterium has been classified as a class I carcinogen by the WHO. *H. pylori* directly induces serious precancerous cellular changes in the mucosal environment and is also responsible for the increase of autoantibodies, which are frequently observed in gastritis and stomach cancer patients (Negrini et al., Gastroenterol. 111:655-665 (1996)). These antibodies are able to induce gastric lesions and apoptosis in the gastric epithelium (Steiniger et al., Virchows Arch. 433:13-18 (1998)). For example, antibodies against the gastric H+/K(+)-ATPase (Claeys et al., Gastroenterology 115:340-347 (1998)), Interleukin-8 (Crabtree et al., Scand. J. Immunol. 37:65-70 (1993); Ma et al., Scand. J. Gastroenterol. 29:961-965 (1994)) and Lewis blood group antigens (Appelmelk et al., Trends. Microbiol. 5:70-73 (1997)) are frequently found in stomach mucosa or stomach cancer.

Therapeutic methods for treating stomach cancer are currently restricted to gastrectomy and lymphadenectomy. Due to the poor prognosis associated with these methods, there is a need for alternative or additional therapeutic and diagnostic methods.

SUMMARY OF THE INVENTION

The present invention features a novel isoform of CFR-1 that is expressed on neoplastic cells as well as on cells of pre-cancerous lesions, but not on normal cells. The novel isoform of CFR-1, and nucleic acids encoding this novel isoform, may be used in methods of inducing an immune response against a neoplastic cell and in screening methods to identify additional therapeutic compounds. In addition, the invention includes polypeptides that bind this novel isoform of CFR-1. These polypeptides may be used in the therapy and diagnosis not only of tumors, but also of pre-cancerous structures both in vitro and in vivo.

Accordingly, the first aspect of the invention features an isolated polypeptide that specifically binds to a neoplastic cell or a cell of a pre-cancerous lesion, but does not specifically bind to a normal cell, where the normal cell is not a cell of the glomerular, fascicular zone of the adrenal gland or an epithelial cell of the collection tubes of the kidney. This isolated polypeptide may include amino acids 11-15, 30-46, and 79-88 of SEQ ID NO:2 and/or amino acids 17-32, 48-54, and 87-95 of SEQ ID NO:4. In desirable embodiments, the polypeptide includes the sequence of SEQ ID NO:2, SEQ ID NO:4, or both of these sequences. In other desirable embodiments, the polypeptide includes amino acids 11-18, 36-43, and/or 82-104 of SEQ ID NO:26 or amino acids 28-32, 51-53, and/or 90-100 of SEQ ID NO:27, but does not include the full-length amino acid sequence of SEQ ID NO:26 or SEQ ID NO:27.

In further desirable embodiments of the first aspect of the invention, the polypeptide is capable of inducing apoptosis of the neoplastic cell or the cell of the pre-cancerous lesion, but does not induce apoptosis of the normal cell. In addition, the neoplastic may be a Barrett's tumor cell or a cell of a tumor of the esophagus, stomach, intestine, rectum, liver, gallbladder, pancreas, lungs, bronchi, breast, cervix, prostate, heart, ovary, or uterus. Furthermore, the pre-cancerous lesion may be a dysplasia of the gastric mucosa, interstitial metaplasia of the stomach, inflammation of the gastric mucosa which is associated with the bacteria *Helicobacter pylori*, tubular and tubulovillous adenomas of the stomach, tubular adenoma of the colon, villous adenoma of the colon, dysplasia in ulcerative colitis, Barrett's dysplasia, Barrett's metaplasia of the esophagus, cervical intraepithelial neoplasia I, cervical intraepithelial neoplasia II, cervical intraepithelial neoplasia III, squamous epithelial metaplasia, squamous epithelial dysplasia of the bronchus, low grade and high grade prostate intraepithelial neoplasia (PIN), breast ductal carcinoma in situ (D-CIS) or breast lobular carcinoma in situ (L-CIS).

In another desirable embodiment of the first aspect, the polypeptide is a functional fragment of an antibody, e.g., a V$_L$, V$_H$, F$_V$, F$_C$, Fab, Fab', or F(ab')$_2$ antibody fragment. In addition, the polypeptide may specifically bind to a polypeptide comprising SEQ ID NO:6 or a fragment thereof.

In the second aspect, the invention features an isolated nucleic acid molecule containing nucleic acids 31-45, 88-138, and/or 235-264 of SEQ ID NO:1. Desirably, this nucleic acid molecule includes the full-length sequence of SEQ ID NO:1. In the third aspect, the invention features an isolated nucleic acid molecule containing nucleic acids 49-96, 142-162, and/or 259-285 of SEQ ID NO:3. In a desirable embodiment of the third aspect of the invention, the nucleic acid molecule includes the full-length sequence of SEQ ID NO:3.

In the fourth aspect, the invention features an isolated nucleic acid molecule including the sequence of SEQ ID NO:5 and in the fifth aspect, the invention features a vector containing the nucleic acid sequence of SEQ ID NO:1, SEQ ID NO:3, or SEQ ID NO:5.

In the sixth aspect, the invention features an isolated cell, e.g., a mammalian cell, containing a vector that includes the nucleic acid sequence of SEQ ID NO:1, SEQ ID NO:3, or SEQ ID NO:5.

In the seventh aspect, the invention features an isolated cell, e.g., a mammalian cell, that expresses the polypeptide of the first aspect of the invention. Desirably, the cell of the seventh aspect of the invention is a human cell.

In the eighth aspect, the invention features a method of producing the purified polypeptide of the first aspect of the invention. This method involves contacting a cell with a vector that includes SEQ ID NO:1 and/or SEQ ID NO:3 and isolating the polypeptide expressed by the vector.

The ninth aspect of the invention features a method of diagnosing a neoplasm or a pre-cancerous lesion in a mammal, e.g., a human. This method involves the steps of (a) contacting a cell or tissue sample derived from the mammal with the purified polypeptide of the first aspect of the invention, and (b) detecting whether the purified polypeptide specifically binds to the cell or tissue sample, where specific binding of the purified polypeptide to the cell or tissue sample is indicative of the mammal having a neoplasm or pre-cancerous lesion. In desirable embodiments of this aspect of the invention, the cell or tissue sample may be Barrett's tumors, tumors of the esophagus, stomach, intestine, rectum, liver, gallbladder, pancreas, lungs, bronchi, breast, cervix, prostate, heart, ovary, and uterus, dysplasia of the gastric mucosa, interstitial metaplasia of the stomach, inflammation of the gastric mucosa which is associated with the bacteria *Helicobacter pylori*, tubular and tubulovillous adenomas of the stomach, tubular adenoma of the colon, villous adenoma of the colon, dysplasia in ulcerative colitis, Barrett's dysplasia, Barrett's metaplasia of the esophagus, cervical intraepithelial neoplasia I, cervical intraepithelial neoplasia II, cervical intraepithelial neoplasia III, squamous epithelial metaplasia, squamous epithelial dysplasia of the bronchus, low grade and high grade prostate intraepithelial neoplasia (PIN), breast ductal carcinoma in situ (D-CIS) or breast lobular carcinoma in situ (L-CIS). In other desirable embodiments of the ninth aspect of the invention, the polypeptide is an antibody, such as murine antibody 58/47-69.

In further desirable embodiments of the ninth aspect, the polypeptide is conjugated to a detectable agent. This detectable agent may be a radionuclide, a fluorescent marker, an enzyme, a cytotoxin, a cytokine, or a growth inhibitor and the detectable agent may also be capable of inducing apoptosis of the cell. In addition, the polypeptide of the ninth aspect may be conjugated to a protein purification tag, e.g., a cleavable protein purification tag.

The tenth aspect of the invention features a method of treating a proliferative disorder in a mammal, for example, a human. This method involves the step of contacting a cell with the purified polypeptide of the first aspect, where binding of the purified polypeptide to the cell results in the induction of apoptosis of the cell. In desirable embodiments of this aspect, the polypeptide is an antibody, e.g., a humanized antibody, a chimeric antibody (i.e., one that comprises amino acid sequence derived from more than one species) or murine antibody 58/47-69. In addition, the polypeptide of the tenth aspect of the invention may be conjugated to a detectable agent. This detectable agent may be a radionuclide, a fluorescent marker, an enzyme, a cytotoxin, a cytokine, or a growth inhibitor. The polypeptide may also be conjugated to a protein purification tag, such as a cleavable protein purification tag.

In the eleventh aspect, the invention features a pharmaceutical composition that contains the isolated polypeptide of the first aspect in a pharmaceutically acceptable carrier and in the twelfth aspect, the invention features a diagnostic agent containing the isolated polypeptide of the first aspect of the invention.

In the thirteenth aspect, the invention features an isolated polypeptide, for example, one that is 90%, 95%, or 99% pure, that includes amino acids 469-518 of SEQ ID NO:6 and/or amino acids 739-748 of SEQ ID NO:6. In a desirable embodiment of the thirteenth aspect, the polypeptide does not include the full-length sequence of SEQ ID NO:6. In another desirable embodiment, the polypeptide of the thirteenth aspect is encoded by the nucleic acid sequence of SEQ ID NO:5.

In further desirable embodiments of the thirteenth aspect, the polypeptide is specifically bound by murine antibody 58/47-69 and/or includes a tumor-specific glycostructure. In addition, the polypeptide may have an apparent molecular weight of approximately 130 kD on a polyacrylamide gel and may be a polypeptide expressed by adenocarcinoma cell line 23132.

In other desirable embodiments of the thirteenth aspect of the invention, the polypeptide is expressed by a pre-cancerous lesion and not by normal cells of the same tissue type. This pre-cancerous lesion may be dysplasia of the gastric mucosa, interstitial metaplasia of the stomach, inflammation of the gastric mucosa which is associated with the bacteria *Helicobacter pylori*, tubular and tubulovillous adenomas of the stomach, tubular adenoma of the colon, villous adenoma of the colon, dysplasia in ulcerative colitis, Barrett's dysplasia, Barrett's metaplasia of the esophagus, cervical intraepithelial neoplasia I, cervical intraepithelial neoplasia II, cervical intraepithelial neoplasia III, squamous epithelial metaplasia, squamous epithelial dysplasia of the bronchus, low grade and high grade prostate intraepithelial neoplasia (PIN), breast ductal carcinoma in situ (D-CIS) or breast lobular carcinoma in situ (L-CIS). Further, the polypeptide of the thirteenth aspect of the invention may be expressed by a tumor such as Barrett's tumor, or tumors of the esophagus, stomach, intestine, rectum, liver, gallbladder, pancreas, lungs, bronchi, breast, cervix, prostate, heart, ovary, or uterus, and not by a normal cell of the same tissue type.

The fourteenth aspect of the invention features a pharmaceutical composition that contains the polypeptide of the thirteenth aspect in a pharmaceutically acceptable carrier and the fifteenth aspect features a diagnostic agent including the isolated polypeptide of the thirteenth aspect.

The sixteenth aspect of the invention features a method of inducing a tumor-specific immune response in a mammal. This method includes the step of contacting the mammal, e.g., a human, with an isolated polypeptide containing the sequence of SEQ ID NO:6 or an isolated polypeptide that comprises amino acids 469-518 of SEQ ID NO:6 or amino acids 739-748 of SEQ ID NO:6 and does not comprise the full-length sequence of SEQ ID NO:6, where the contacting induces a tumor-specific immune response in the mammal. Desirably, the tumor-specific immune response involves the production of an antibody that induces apoptosis of a cell which is specifically bound by the antibody.

In further desirable embodiments of this aspect, the invention features a DNA vaccine comprising a plasmid vector or a viral vector which includes a nucleotide sequence encoding SEQ ID NO:6, or a fragment thereof, where, upon administration into a patient, a tumor-specific immune response is induced in the patient. This immune response, for example, results in the formation of antibodies that specifically bind to a neoplasm or a pre-cancerous lesion.

In the seventeenth aspect, the invention features a method of producing an isolated polypeptide containing the sequence of SEQ ID NO:6 or a fragment thereof that comprises amino acids 469-518 of SEQ ID NO:6 or amino acids 739-748 of SEQ ID NO:6 and does not comprise the full-length sequence of SEQ ID NO:6. This method involves the steps of (a) contacting a cell with a vector containing a nucleic acid sequence that is substantially identical or identical to SEQ ID NO:5 and (b) isolating the polypeptide expressed by the cell. In a desirable embodiment, the fragment comprises amino acids 469-518 of SEQ ID NO:6 and amino acids 739-748 of SEQ ID NO:6 and does not comprise the full-length sequence of SEQ ID NO:6.

The eighteenth aspect of the invention features a method of identifying a candidate therapeutic compound. This method involves the steps of (a) contacting a cell expressing a polypeptide containing the amino acid sequence of SEQ ID NO:6, e.g., adenocarcinoma cell line 23132 (DSMZ Accession No. DSM ACC 201), with a test compound and (b) determining whether the test compound induces apoptosis of the cell and not of a control cell contacted with the test compound, where a test compound that induces apoptosis of the cell and not of the control cell is a candidate therapeutic compound. In desirable embodiments of this method, fragments of SEQ ID NO:6, for example, ones that comprise amino acids 469-518 of SEQ ID NO:6 or amino acids 739-748 of SEQ ID NO:6 and do not comprise the full-length sequence of SEQ ID NO:6, may be used.

Definitions

By "novel CFR-1 isoform" and "the isoform of CFR-1 that is recognized by a PAM-1 antibody" is meant an isoform of CFR-1 that includes amino acids 469-518 of SEQ ID NO:6 and/or amino acids 739-748 of SEQ ID NO:6 and that is expressed by neoplastic cells and cells of a pre-cancerous lesion and not by a normal cell, where cells of the glomerular, fascicular zone of the adrenal gland or an epithelial cell of the collection tubes of the kidney are excluded from the group of normal cells. Desirably, the novel CFR-1 isoform does not comprise the full-length amino acid sequence of SEQ ID NO:6. In further desirable embodiments, the novel CFR-1 isoform is specifically-bound by human monoclonal antibody 103/51 and/or murine antibody 58/47-69 and has a molecular mass of approximately 130 kD. The use of the term "approximately" reflects that one skilled in the art would recognize that these types of size determinations are affected by changes or variations of the methods of the molecular size determination, e.g., gel electrophoresis conditions. In addition, the novel CFR-1 isoform is a polypeptide present on adenocarcinoma cell line 23132 (DSMZ Accession No. DSM ACC 201).

In other desirable embodiments, the novel CFR-1 isoform is expressed by the cells of the following types of pre-cancerous lesion, but not normal cells: *H. pylori* induced gastritis, intestinal metaplasia and dysplasia of the stomach, ulcerative colitis-related dysplasia and adenomas of the colon, Barrett metaplasia and dysplasia of the esophagus, squamous cell metaplasia and dysplasia of the lung, cervical intraepithelial neoplasia, low grade and high grade prostate intraepithelial neoplasia (PIN), breast ductal carcinoma in situ (D-CIS) and breast lobular carcinoma in situ (L-CIS).

In further desirable embodiments, the novel CFR-1 isoform is expressed by carcinomas of the following tissues, but not normal cells of the same tissues: esophagus, stomach, colon, liver, pancreas, lung, breast, ovary, uterus, cervix, and prostate.

By a "PAM-1 antibody" is meant a polypeptide that specifically binds to the isoform of CFR-1 that comprises the amino acid sequence of SEQ ID NO:6 and that is expressed by 23132 cells. In a desirable embodiment, a PAM-1 antibody binds a tumor-specific glycostructure of the CFR-1 isoform having the amino acid sequence of SEQ ID NO:6. For example, a PAM-1 antibody may be human monoclonal antibody 103/51, murine antibody 58-49/69, or a humanized or chimeric antibody containing all or part of the sequence of SEQ ID NO:2 and/or 4. In further desirable embodiments, a PAM-1 antibody can induce apoptosis or alter proliferation, or both, in a neoplastic cell or a cell of a pre-cancerous lesion, but not a normal cell. In additional desirable embodiments, a PAM-1 antibody comprises the amino acid sequence of SEQ ID NO:2 and/or SEQ ID NO:4 or is encoded, in part, by the nucleic acid sequence of SEQ ID NO:1 and/or SEQ ID NO:3. In further desirable embodiments, a PAM-1 antibody may comprise amino acids 11-18, 36-43, and/or 82-104 of SEQ ID NO:26 and/or amino acids 28-32, 51-53, and/or 90-100 of SEQ ID NO:27.

By a "functional fragment" or a "fragment of a PAM-1 antibody" as used herein in reference to polypeptide, is meant a fragment that retains at least one biological activity of the full-length polypeptide. Examples of such a biological activity are the ability to specifically bind an antigen, induce apoptosis, and/or inhibit cell proliferation. The biological activities of a functional fragment may be determined, for example, using any one of the assays described herein. Examples of functional fragments of an antibody are $V_L$, $V_H$, $F_V$, $F_C$, Fab, Fab', or F(ab')$_2$ fragments which are known to one skilled in the art (see, e.g., Huston et al., Cell Biophys. 22:189-224, 1993; and Harlow and Lane, Using Antibodies: A Laboratory Manual, Cold Spring Harbor Laboratory Press, N.Y., 1999). Desirably, a "functional fragment" has an amino acid sequence that is substantially identical to a fragment, e.g., 3, 4, 5, 10, 15, 20, 15, 30, 50, 75, or 100 contiguous amino acids, of the amino acid sequence of SEQ ID NO:2 or 4. In more desirable embodiments, a "functional fragment" is identical to a fragment of the sequence of SEQ ID NO:2 or 4. Such a "functional fragment" may contain 3, 4, 5, 6, 7, 8, 9, 10, 15, 20, 15, 30, 50, 75, or 100 contiguous amino acids of SEQ ID NO:2 or 4, or may be the entire amino acid sequence of SEQ ID NO:2 or 4. In desirable embodiments, such a fragment includes one or more of the Complement Determining Regions (CDR) of the $V_H$ or the $V_L$ regions of the murine PAM-1 antibody 58-49/69. For example, a functional fragment may include amino acids 11-15, 30-46, and/or 79-88 of SEQ ID NO:2; and/or amino acids 17-32, 48-54, and/or 87-95 of SEQ ID NO:4.

By "detectable agent" is meant a compound that is linked to a diagnostic agent to facilitate detection. Such a "detectable agent" may be covalently or non-covalently linked to a diagnostic agent. In addition, the linkage may be direct or indirect. Examples of "detectable agents" include, protein purification tags, cytotoxins, enzymes, paramagnetic labels, enzyme substrates, co-factors, enzymatic inhibitors, dyes, radionuclides, chemiluminescent labels, fluorescent markers, growth inhibitors, cytokines, antibodies, and biotin.

By a "diagnostic agent" is meant a compound that may be used to detect a neoplastic cell by employing any one of the assays described herein as well as any other method that is standard in the art. A diagnostic agent may include, for example, an antibody which specifically binds to cell line 23132 (DSMZ Accession No. ACC 201), but not to normal cells. In addition, a diagnostic agent may specifically bind to cells of pre-cancerous lesions such as those exhibiting *H. pylori* induced gastritis, intestinal metaplasia and dysplasia of the stomach, ulcerative colitis-related dysplasia and adenomas of the colon, Barrett metaplasia and dysplasia of the esophagus, squamous cell metaplasia and dysplasia of the lung, cervical intraepithelial neoplasia, low grade and high grade prostate intraepithelial neoplasia (PIN), breast ductal carcinoma in situ (D-CIS) and breast lobular carcinoma in situ (L-CIS). A diagnostic agent may also specifically bind carcinomas of the esophagus, stomach, colon, liver, pancreas, lung, breast, ovary, uterus, cervix, and prostate, but not non-neoplastic cell of the same tissue type. Furthermore, a "diagnostic agent" may alter cell proliferation, induce apoptosis, or both only when it is bound to a neoplastic cell or a cell of a pre-cancerous lesion, but not a normal cell. Moreover, a "diagnostic agent" may include, for example, peptides, polypeptides, synthetic organic molecules, naturally-occurring organic molecules, nucleic acid molecules, and components thereof, as well as one or more detectable agent covalently or non-covalently linked to the diagnostic agent.

By "high stringency hybridization conditions" is meant, for example, hybridization at approximately 42° C. in about 50% formamide, 0.1 mg/ml sheared salmon sperm DNA, 1% SDS (Sodium Dodecyl Sulfate), 2×SSC (Sodium Citrate Buffer), 10% Dextran Sulfate, a first wash at approximately 65° C. in about 2×SSC, 1% SDS, followed by a second wash at approximately 65° C. in about 0.1×SSC. Alternatively, "high stringency hybridization conditions" may include hybridization at approximately 42° C. in about 50% formamide, 0.1 mg/ml sheared salmon sperm DNA, 0.5% SDS, 5×SSPE, 1× Denhardt's, followed by two washes at room temperature in 2×SSC, 0.1% SDS, and two washes at between 55-60° C. in 0.2×SSC, 0.1% SDS.

"Altering cell proliferation," as used herein, refers to a reduction or an increase in the rate of cell division of a cell in comparison with the normal rate of cell division of that type of cell under the same conditions. Cell proliferation may be assayed using a number of methods standard in the art, for example, the MTT cell proliferation assay described herein, BrdU incorporation, and $^3$H thymidine uptake. Such assays are described, for example, in Ausubel et al., *Current Protocols in Molecular Biology*, Wiley Interscience, New York, 2001; and Sambrook et al., *Molecular Cloning: A Laboratory Manual*, $3^{rd}$ edition, Cold Spring Harbor Laboratory Press, N.Y., 2001. Desirably, the increase or decrease of cell proliferation is 20%, 40%, 50%, or 75%. In desirable embodiments, the increase or decrease of cell proliferation is 80%, 90%, 95%. In another desirable embodiment cell proliferation is completely inhibited.

"Inducing apoptosis," as used herein, refers to the appearance of characteristics in a cell that are well defined in the art (see, e.g., Wyllie et al., Br. J. Cancer 80 Suppl. 1:34-37, 1999; Kerr et al., Br. J. Cancer 26:239-257, 1972). These characteristics include morphological characteristics, such as membrane blebbing, DNA condensation, as well as changes in F-actin content, mitochondrial mass, and membrane potential. The induction of apoptosis may be assayed using a number of methods standard in the art, for example, a cell death ELISA, TUNEL staining, DNA stains, e.g., Hoechst 33258, and staining with various vital dyes such as acridine orange, Mito Tracker Red® staining (Molecular Probes, Eugene, Oreg.), and Annexin V® staining (Becton Dickinson, New Jersey). As used herein "inducing apoptosis" refers to an increase in the number of cells undergoing apoptosis when compared with a control cell population under the same conditions. For instance, the increase of apoptosis may be 10%, 20%, 40%, 50%, or 75%. In desirable embodiments, the induction of apoptosis results in an increase of apoptosis that is 2-fold, 3-fold, 10-fold, or even 100-fold over that seen in a control cell population.

A "humanized antibody" as used herein, is a genetically engineered antibody in which a minimum of a non-human, e.g., a murine, antibody sequence is combined with human antibody sequence and still maintains the binding specificity of the original non-human antibody. In desirable embodiments, a humanized antibody contains 15%, 20%, 25%, 30%, or 40% non-human sequence. In more desirable embodiments, a humanized antibody contains 5% or 10% non-human sequence. In addition, a humanized antibody desirably induces no or only a minimal human immune response.

A "neoplastic cell," as used herein, refers to a cell which is undergoing cell division, not undergoing apoptosis, or both, under inappropriate conditions. For example, a "neoplastic cell" may undergo cell division when a corresponding normal cell does not undergo cell division, or, alternatively, a "neoplastic cell" may not respond to normal cell-cycle checkpoint controls.

By a "cell of a pre-cancerous lesion" is meant cells that are undergoing cell division, not undergoing apoptosis, or both, under inappropriate conditions, but that have not developed into a cancerous tumor. For example, cells in a pre-cancerous lesion may undergo cell division when a corresponding normal cell does not undergo cell division, or, alternatively, cells of a pre-cancerous lesion may not respond to normal cell-cycle checkpoint controls. Examples of pre-cancerous lesions include *H. pylori* induced gastritis, intestinal metaplasia and dysplasia of the stomach, ulcerative colitis-related dysplasia and adenomas of the colon, Barrett metaplasia and dysplasia of the esophagus, squamous cell metaplasia and dysplasia of the lung, cervical intraepithelial neoplasia, low grade and high grade prostate intraepithelial neoplasia (PIN), breast ductal carcinoma in situ (D-CIS) and breast lobular carcinoma in situ (L-CIS).

By a "normal cell" as used herein is meant a cell that is neither a neoplastic cell nor a cell of a pre-cancerous lesion.

A "proliferative disease," as used herein, refers to any disorder that results in the abnormal proliferation of a cell. Specific examples of proliferative diseases are various types of neoplasms, such as stomach adenocarcinoma, colorectal adenocarcinoma, lung adenocarcinoma, and adenocarcinoma of the pancreas. However, proliferative diseases may also be the result of the cell becoming infected with a transforming virus.

A "protein purification tag," as used herein, is a peptide, e.g., an epitope tag, that is covalently or non-covalently added to a protein to aid in the purification of the protein. Desirably such peptides bind with high affinity to an antibody or to another peptide such as biotin or avidin. Commercially available examples of epitope tags include His-tags, HA-tags, FLAG®-tags, and c-Myc-tags. However, any epitope that is recognized by an antibody also may be used as a protein purification tag. See, for example, Ausubel et al., *Current Protocols in Molecular Biology*, Wiley Interscience, New York, 2001; and Sambrook et al., *Molecular Cloning: A Laboratory Manual*, 3$^{rd}$ edition, Cold Spring Harbor Laboratory Press, N.Y., 2001. Protein purification tags may be cleaved from a protein, for example, by using an enzyme, e.g., thrombin, or a chemical, e.g., cyanogen bromide.

By "specifically binds" and "specifically recognizes" as used herein in reference to a polypeptide, e.g., an antibody, is meant an increased affinity of a polypeptide for a particular protein, e.g., an antigen, relative to an equal amount of any other protein. For example, an antibody, e.g., the human or murine PAM-1 antibody, that specifically binds to 23132 cells desirably has an affinity for its antigen that is least 2-fold, 5-fold, 10-fold, 30-fold, or 100-fold greater than for an equal amount of any other antigen, including related antigens. Binding of a polypeptide to another polypeptide may be determined as described herein, and by any number of standard methods in the art, e.g., Western analysis, ELISA, or co-immunoprecipitation.

By "substantially identical" is meant a polypeptide or nucleic acid exhibiting at least 80%, 85%, 90%, or 95% identity to a reference amino acid (e.g., the sequence of SEQ ID NO:2, 4, or 6) or nucleic acid sequence (e.g., the sequence of SEQ ID NO:1, 3, or 5), or a fragment thereof. In desirable embodiments, the polypeptide or nucleic acid sequence is at least 98%, 99%, 99.4%, 99.5%, 99.6%, 99.7%, 99.8%, 99.9%, or even 100% identical to a reference amino acid or nucleic acid sequence. For polypeptides, the length of comparison sequences will generally be at least 3, 4, 5, 6, 8, 10, or 15 amino acids and desirably at least 20 or 25 contiguous amino acids. In more desirable embodiments, the length of comparison sequences is at least 30, 50, 75, 90, or 95 contiguous amino acids, or even the full-length amino acid sequence. For nucleic acids, the length of comparison sequences will generally be at least 9, 10, 12, 15, 18, 20, 24, or 25 contiguous nucleotides, and desirably at least 30 contiguous nucleotides. In more desirable embodiments, the length of comparison sequences is at least 50, 75, 150, 225, 270, 280, 285, or 290 contiguous nucleotides, or even the full-length nucleotide sequence.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

By "purified" or "isolated" is meant separated from other components that naturally accompany it. Typically, a factor is "purified" or "isolated" when it is at least 50%, by weight, free from proteins, antibodies, and naturally-occurring organic molecules with which it is naturally associated, or in reference to a nucleic acid molecule, is free from the nucleic acid sequences that naturally flank the sequence of the nucleic acid molecule in the genome of an organism. Desirably, the factor is at least 75%, more desirably, at least 90% or 95% and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques, such as those described by Ausubel et al. (*Current Protocols in Molecular Biology*, Wiley Interscience, New York, 2001). The factor is desirably at least 2, 5, or 10 times as pure as the starting material, as measured using polyacrylamide gel electrophoresis, column chromatography, optical density, HPLC analysis, or Western analysis (Ausubel et al., *Current Protocols in Molecular Biology*, Wiley Interscience, New York, 2001). Desirable methods of purification include immunoprecipitation, column chromatography such as immunoaffinity chromatography and nickel affinity columns, magnetic bead immunoaffinity purification, and panning with a plate-bound antibody.

By a "tumor-specific glycostructure" is meant a glycostructure on a polypeptide which is present on a neoplastic cell or a pre-cancerous cell, but not on a normal cell of the same type.

By "vector" or "expression vector" is meant an expression system, a viral vector, a nucleic acid-based shuttle vehicle, a nucleic acid molecule adapted for nucleic acid delivery, or an autonomous self-replicating circular DNA (e.g., a plasmid). When a vector is maintained in a host cell, the vector can either be stably replicated by the cell during mitosis as an autonomous structure, incorporated into the genome of the host cell, or maintained in the host cell's nucleus or cytoplasm.

Advantages

The CFR-1 isoform described herein, as well as antibodies that bind this isoform, unlike previously described proliferation markers, e.g., Ki67, may be used to differentiate between normal and neoplastic cells. In addition, the polypeptides of the invention can be used to identify cells that are likely to give rise to a tumor, such as cells of a pre-cancerous lesion.

Other features and advantages of the invention will be apparent from the following Detailed Description, the drawings, and the claims.

BRIEF DESCRIPTION OF THE DRAWINGS

FIG. 1A is an image of a protein gel and shows the antigen recognized by antibody 103/51. Membrane fractions from stomach carcinoma cell line 23132 were purified using chromatographic procedures and whole membrane fraction (lane 2), or purified proteins (lane 3) were stained with Coomassie (lane 1: 10 kDa ladder). Western blot analysis with antibody 103/51 on membrane fractions of cell line 23132 showed one reaction with a protein with a molecular mass of approximately 130 kD (lane 4). Specificity of processed membrane extracts was controlled by Western blotting with 103/51 (lane 5). The protein band indicated by the arrow was excised from a preparative gel and used for MALDI mass mapping and immunization of mice.

FIG. 1B is a spectrograph of the identification of the 130 kDa gel-separated protein by high resolution MALDI peptide mass mapping. Peaks labeled with '*' match the calculated masses of tryptic peptides of U28811 human cysteine-rich fibroblast growth factor receptor (CFR-1) with a mass accuracy better than 50 ppm. Peaks labeled with 'T' correspond to trypsin autolysis products. The inset shows the mass resolution (m/Δm=9000) of the peak at m/z 1707.818.

FIG. 2A shows cell line 23132 transiently transfected with a control vector and, after acetone fixation, shows intensive staining with antibody 103/51. FIG. 2B shows reduced staining in cells transiently transfected with an CFR-1 antisense vector. To reduce background staining in immunohistochemical staining, live cell staining was performed with cell line 23132. A clear membrane staining is visible (FIG. 2C). FIG. 2D shows control live cell staining, using only secondary antibody, on cell line 23132. FIG. 2E shows a lack of live cell staining on cell line Colo-699 with antibody 103/51, which indicates that this cell line is negative for expression of CFR-1. FIG. 2F shows control live cell staining, using only secondary antibody, on cell line Colo-699.

FIG. 21 is a graph of cells transfected with CFR-1 antisense vector, which shows a clear decrease in binding of antibody 103/51.

FIG. 3A shows 23132 cells incubated with deglycosylation buffer and acetone-fixed show intense staining with antibody 103/51 and FIG. 3B shows 23132 cells treated with N-glycosidase followed by acetone fixation. A clear reduction in staining is evident as a result of the N-glycosidase treatment.

FIGS. 5A-5D are a series of images showing immuno-histochemical staining of antibody 103/51 on different gastric tissues. Cryo-sections of gastric tissues were stained with haematoxilin-eosin ("HE"), antibody Ki67 (to indicate proliferating cells) and antibody 103/51. The magnification is 100×. FIG. 5A shows gastric tissue with inflammation. FIG. 5B shows *H. pylori* induced gastritis (inserts show a higher magnification of marked glands). FIG. 5C shows dysplasia and FIG. 5D shows gastric adenocarcinoma cells.

FIG. 7A is graph of a titration with purified antibody 103/51 which shows an increase in stimulation up to 4 μg/ml. Higher concentrations do not lead to higher stimulation (c=Control, no antibody added). FIG. 7B is a graph of the results of an MTT-assay with equal concentrations (4 μg/ml) of purified antibodies 103/51 and 58/47-69 and shows comparable stimulation of tumor cell 23132 after one or two days of incubation (Control 1=chromopure human IgM, Control 2, uncorrelated mouse IgM). FIG. 7C is a graph of the results of an experiment in which cell line 23132 was transiently transfected with control vector pHOOK-2 or CFR-1 antisense vector, incubated for 24 hours, and tested in the MTT assay for stimulation with 4 μg/ml purified antibody 103/51 after 24 hours. Untransfected cells were also incubated as control (Control, uncorrelated human IgM). FIG. 7D is a graph of the results of an MTT-assay with equal concentrations (4 μg/ml) of antibody 103/51 on different epithelial tumor cell lines. This graph shows stimulation only on the cell line 23132 24 hours after addition of antibody. Cell lines that do not express the antigen recognized by the PAM-1 antibody (Colo-699 and EPLC-272H) do not show any stimulation by antibody 103/51.

FIGS. 8A and 8B are the nucleic acid sequence (SEQ ID NO:1) and the amino acid sequence (SEQ ID NO:2) of the variable region of the heavy chain of murine antibody NM58-49/69. The J-gene and D-gene, as well as Complement Determining Regions (CDR)1 to 3 are indicated in FIG. 8B.

FIGS. 9A and 91B are the nucleic acid sequence (SEQ ID NO:3) and the amino acid sequence (SEQ ID NO:4) of the variable region of the light chain of murine antibody NM58-49/69. Complement Determining Regions (CDR)1 to 3 are indicated in FIG. 9B.

FIGS. 10-1 to 10-5 are the nucleic acid (SEQ ID NO:5) and amino acid sequence (SEQ ID NO:6) of the novel isoform of CFR-1 expressed by cell line 23132.

FIG. 11A shows a Coomassie blue stained SDS gel of intact PAM-1 antibody (lane 1) and the fragmented antibody after 10 min (lane 2)

and 15 min (lane 3) of pepsin treatment. FIG. 11B shows the specific protein bands of intact (lane 1) and fragmented (lane 2 and 3) PAM-1 antibody.

FIGS. 12A and 12B are a series of images showing immunohistochemical staining of intact and fragmented PAM-1 antibody on pre-malignant and malignant tissue. Paraffin sections were stained with positive control (anti-cytokeratin 8), unrelated fragmented IgM as a negative control, intact PAM-1 antibody or fragmented PAM-1 antibody. FIG. 12A shows vilous adenoma of the colon (precursor lesion of coloncarcinoma)

FIG. 13A shows concentration dependent inhibition of cell proliferation with fragmented PAM-1 antibody. FIG. 13B shows antibody induced apoptosis with the fragmented form of PAM-1 after 24 hours of treatment (control 1: no antibody was added; control 2: unrelated fragmented IgM was added at a similar concentration).

FIG. 14A shows tumor size development of mice treated with fragmented form of PAM-1 antibody or unrelated fragmented IgM (control group) over a period of 23 days. FIGS. 14B and 14C show that antibody-reduced tumor mass is measurable in mice treated with fragmented PAM-1 antibody after 23 days. A group of mice treated with unrelated fragmented IgM served as a control in all experiments.

FIGS. 15A and 15D show HE staining; FIGS. 15B and 15E show immunoperoxidase staining with apoptosis positive control, all cell nuclei are stained; and FIGS. 15C and 15F show immunoperoxidase staining with DNA fragmentation Kit, only the nuclei of apoptotic cells are stained (original magnification, ×100/×200).

FIG. 16 is a comparison of the amino acid sequence of the CFR-1 obtained from cell line 23132 (SEQ ID NO:6) to the published sequences of CFR-1 and MG160 (SEQ ID NOS:7 and 8). These experimental comparisons primarily show that the CFR-1 protein obtained from cell line 23132 is not identical to the CFR-1 sequences previously known, but represents a novel isoform thereof. The differences between the sequences are underlined.

FIG. 17 is the nucleic acid sequence (SEQ ID NO:26) and the amino acid sequence (SEQ ID NO:28) of the variable region of the heavy chain of the human PAM-1 antibody (clone 103/51). The Complement Determining Regions (CDR)1 to 3 are indicated.

FIG. 18 is the nucleic acid sequence (SEQ ID NO:27) and the amino acid sequence (SEQ ID NO:29) of the variable region of the light chain of the human PAM-1 antibody (clone 103/51). The Complement Determining Regions (CDR)1 to 3 are indicated.

DETAILED DESCRIPTION

Figure 1:
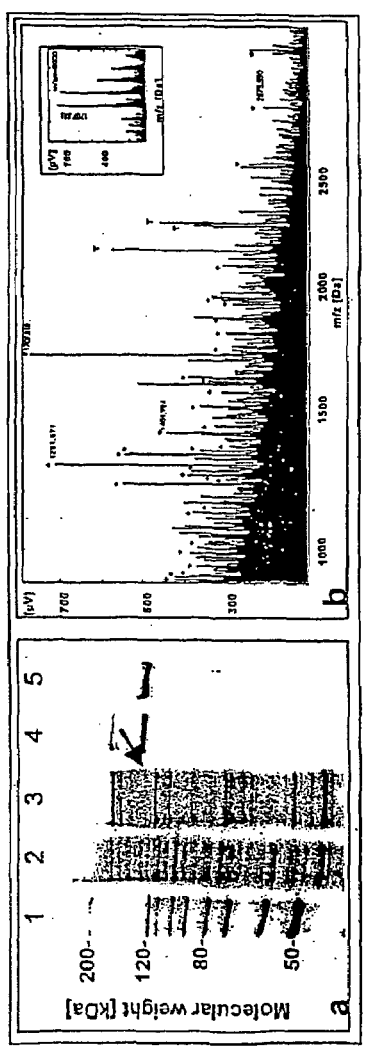

The present invention features novel polypeptides and methods of using these polypeptides in the diagnosis, detection, monitoring, and treatment of neoplasms in a mammal, e.g., a human. In particular, the isoform of CFR-1 described herein and polypeptides that bind this antigen, such as human monoclonal antibody 103/51 and murine antibody 58-49/69, enable the therapy and diagnosis not only of tumors, but also of pre-cancerous structures both in vitro and in vivo. Moreover, the novel isoform of CFR-1 may be used in screening methods to identify additional therapeutic compounds.

Immunological studies have shown that in cases in which the immune system cannot effectively combat malignant cells, cellular and humoral activity is measurable, but is not sufficient to destroy the tumor cells. Currently, an effective approach to increase the efficacy of the immune response is to isolate the antibodies arising from the immune response of the patient, reproduce them in a suitable way, and use them therapeutically. Thus, for example, antibodies originating from patients having lung, esophageal, and colon cancers may be isolated and human monoclonal antibodies may be derived therefrom, which, for example, directly influence differentiation and growth of the tumor cells.

We have described that the human antibody 103/51 (human PAM-1), which was isolated from a stomach cancer patients with diffuse-type adenocarcinoma and cross-reacts with cells present in *H. pylori*-induced gastritis and stomach cancer cells. Sequencing of the antibody variable gene regions identified the human PAM-1 antibody (103/51) as an autoreactive antibody. In low doses, PAM-1 antibodies (both human and murine) have a mitotic effect on stomach cancer cells in vitro, in which they bind on a 130 kD membrane receptor.

The cellular receptor of monoclonal antibody 103/51 was previously unknown. In the course of the experiments leading to the present invention, we were able to identify this cellular receptor. The monoclonal antibody 103/51 reacts with its receptor during Western blot analysis only under very specific stringency conditions and non-specific reactions are found with an array of further proteins, caused by denaturing artifacts.

Sequencing analyses have shown that the antigen recognized by PAM-1 is homologous to the CFR-1 protein, but is not identical to this protein. This isoform of CFR-1 is specifically bound by human PAM-1 antibody (103/51) and/or murine PAM-1 antibody (58/47-69). The isoform of CFR-1 described herein is specific for tumor cells, particularly for gastric carcinoma cells and is not expressed by normal stomach tissue.

We further characterized this isoform of CFR-1 and determined that it contains a special glycostructure that is linked to the protein backbone via an N-linkage. In addition, the specificity for the antigen of human PAM-1 antibody 103/51 was confirmed by producing murine antibodies from purified molecules having identical reactions and functions, through immunohistochemical staining, and an MTT assay of two cell lines that do not express the CFR-1 isoform recognized by the PAM-1 antibody. The isoform of the CFR-1 molecule, which was detected by both the human and the murine antibodies, is localized in the cell membranes of the epithelial cells, and has an expression pattern which differs from that previously described for wild-type CFR-1 (Burrus et al., 1992, Mol. Cell. Biol. 12:5600-5609).

CFR-1

Wild-type CFR-1, which was isolated as a high-affinity FGF-binding protein from chicken fibroblasts (Burrus et al., 1992, Mol. Cell. Biol. 12:5600-5609), binds to a number of FGFs and may have a role in the regulation of cellular proliferation. In Chinese hamster ovary cells (CHO), CFR-1 was found to be expressed only in the Golgi apparatus (Burrus et al., 1992, Mol. Cell. Biol. 12:5600-5609), but it can also be secreted in a mutant form (Zuber et al., 1997, J. Cell Physiol. 170:217-227). Depending on the organism, two detected variants of CFR-1, ESL-1, and MG-160 share sequence homologies between 80% and 95% (Burrus et al., 1992, Mol. Cell. Biol. 12:5600-5609; Stieber et al., 1995, Exp. Cell Res. 219:562-570; Steegmaier et al., 1995, Nature 373:615-620; Mourelatos et al., 1996, DNA Cell Biol. 15:1121-1128) and do not appear to share any sequence homologies to other known proteins. The function and cellular distribution of CFR-1 and the ESL-1 and MG-160 is relatively undefined and contradictory. It has been shown that MG-160, which is a medial Golgi sialoglycoprotein and was purified from rat brains, plays a role in intracellular FGF trafficking (Zuber et al., 1997, J. Cell Physiol. 170:217-227).

Recent findings have shown that the localization of this protein is not restricted to the Golgi apparatus. However, if truncated at the c-terminus, the protein can be localized to the plasma membrane and filopodia (Gonatas et al., 1998, J. Cell Sci. 111:249-260). This is consistent with the finding that the third homologue, ESL-1, which was isolated from mouse neutrophilic progenitor cells (32Dcl3), is located in the Golgi apparatus as well on the cell surface of the microvilli (Steegmaier et al., 1997, J. Cell Sci. 110:687-694, Gonatas et al., 1998, J.Cell Sci. 111:249-260). ESL-1 was identified as ligand for E-selectin in neutrophils with an approximate molecular mass of 150 kD. Immunoprecipitation with anti ESL-1 antibodies showed that a non-defined isoform of this protein could be precipitated from various cells, including some cancerous cell lines (Steegmaier et al., 1995, Nature 373:615-620).

The tissue distribution shows that the tumor and pre-cancerous lesion-specific isoform of CFR-1 described herein is correlated with cellular activation and proliferation demonstrated by staining with antibody Ki67 (Ramires et al., 1997, J. Pathol. 182:62-67). Variable cellular distribution of a protein is a known phenomenon (Smalheiser, 1996, Mol. Biol. Cell 7:1003-1014). An altered distribution might be caused by a different glycosylation pattern in malignant cells, which may lead to a transport to the plasma membrane. Normal stomach mucosa does not express this receptor in a measurable amount, but *H. pylori* infiltrated epithelia and dysplastic epithelia express this antigen. Both tissues proliferate and may be precursors for gastric carcinoma.

In contrast to the previously described structure of CFR-1, which is found in normal cells, the isoform of CFR-1 described herein is not found on normal cells, but exclusively on proliferating cells associated with malignancies, such as the tumor cells found in the growth and corresponding precursor stages. Thus, the CFR-1 isoform described herein may be used not only in the diagnosis and treatment of gastric carcinomas, but rather also for all epithelial tumors. Besides gastric tumors, the existence of these receptors was proven in cancerous tissue of the following tumors: esophagus, stomach, intestines, rectum, liver, gallbladder, pancreas, lungs, bronchi, breast, cervix, prostate, cardiac, Barrett's, ovary, and/or uterus. An antibody, e.g., a PAM-1 antibody, which binds to the isoform of CFR-1 described herein therefore has a targeted activity on the cancerous or pre-cancerous (and not normal) cells.

Antibodies and Polypeptides

Antibodies play an essential role in maintaining the health of an individual. In particular, antibodies are present in serum and bind to and help eliminate diverse pathogens such as bacteria, viruses, and toxins. Antibodies consist of Y-shaped protein structures built from two heavy chains and two light chains. Each chain has a modular construction: each light chain consists of two domains, and each heavy chain has at least four domains. The antigen binding site is fashioned by one domain from the heavy chain ($V_H$ domain) and one domain from the light chain ($V_L$ domain). Indeed, small antigen binding fragments can be prepared by linking these two domains, either associated non-covalently, or covalently via disulphide bonds or a peptide linker. The antigen binding domains are more variable in amino acid sequence than the other domains of the antibody, and are therefore termed variable (V) domains, in contrast to the constant (C) domains. The constant domains of the antibody are responsible for triggering antibody effector mechanisms, such as complement lysis and cell-mediated killing.

Antibodies are made by B-lymphocytes in a process involving gene rearrangement. During the development of these cells, the genes encoding the variable domains are assembled from genetic elements. In the case of the $V_H$ domains there are three elements, the un-rearranged $V_H$ gene, D segment, and $J_H$ segment. In the case of the $V_L$ domains, there are two elements, the un-rearranged $V_L$ (V Lambda or V Kappa) gene and the $J_L$ (J Lambda or J Kappa) segment. Random combination of these gene segments and random combination of the rearranged $V_H$ and $V_L$ domains generate a large repertoire of antibodies, capable of binding to a large diversity of equally diverse antigens. Further, the $V_H$ and $V_L$ regions each have three Complement Determining Regions (CDR) and four framework regions (FR). The FRs are the backbone of the antibody and the CDRs are the parts of the antibody that bind the antigen. One skilled in the art can determine the FR and CDR regions of an antibody by comparing the amino acid sequence of a number of antibodies raised in the same species (see, e.g., Altschul et al., Nucleic Acids Res. 25:3389-3402, 1997; and Kabat et al., Sequences of Proteins of Immunological Interest, $5^{th}$ edition, NIH Publication No. 91-3242, U.S. Department of Health and Human Services, 1991).

Production of Neoplasm-Specific Polypeptides

A PAM-1 antibody or a fragment thereof may be produced by expression in a hybridoma or in a host cell such as *E. coli* or yeast, e.g., *S. cerevisiae*, or a mammalian cell line. Functional fragments of polypeptides may also be generated, for example, by direct synthesis using recombinant methods. These methods are standard in the art. For example, a nucleic acid sequence may be amplified using the polymerase chain reaction (PCR). The PCR technique is known in the art and is described, for example in U.S. Pat. No. 4,683,195. Using standard methods, and as described herein, the sequence of a monoclonal antibody expressed by a hybridoma or trioma may be obtained and functional fragments of the antibody may be amplified. For example, whole RNA may be isolated from a hybridoma expressing a tumor-specific monoclonal antibody. cDNA may then be generated from the RNA using reverse transcriptase and the cDNAs which contain the functional fragments of the variable regions of the heavy and light chains may be amplified using PCR. The PCR products may then be purified and cloned into expression vectors, e.g., plasmid or viral vectors. Many standard vectors are available and the selection of the appropriate vector will depend on, for example, the size of the DNA inserted into the vector and the host cell to be transfected with the vector.

The nucleic acid molecules identified using the methods of the invention may be expressed in a variety of standard vectors and host cells. Any promoter that is active in the host cell may be used to express a nucleic acid molecule. Nonetheless, for expression of an antibody or a fragment of an antibody in a mammalian cell, use of an immunoglobulin gene promoter is desirable. Methods of introducing a vector into a host cell are standard in the art and include, electroporation, use of synthetic lipid polymers, e.g., Lipofectin™, use of calcium chloride, and use of DEAE Dextran. Such methods are also described in, for example, Ausubel et al., *Current Protocols in Molecular Biology*, Wiley Interscience, New York, 2001; and Sambrook et al., *Molecular Cloning: A Laboratory Manual*, $3^{rd}$ edition, Cold Spring Harbor Laboratory Press, N.Y., 2001.

Isolation of Amino Acid Variants of a PAM-1 Antibody

Amino acid sequence variants of a PAM-1 antibody can be prepared by introducing appropriate nucleotide changes into the DNA encoding the antibody, or by in vitro synthesis of the desired polypeptide. Such variants include, for example, deletion, insertion, or substitution of, residues within the amino acid sequence of a PAM-1 antibody. Any combination of deletion, insertion, and substitution can be made to arrive at the final construct, provided that the final construct possesses the desired characteristics, e.g., the ability to induce apoptosis of a neoplastic cell, but not a non-neoplastic cell, or the ability to inhibit the proliferation of a cell. The amino acid changes also may alter post-translational processes of an antibody, such as changing the number or position of glycosylation sites, altering the membrane anchoring characteristics, or modifying its susceptibility to proteolytic cleavage.

In designing amino acid sequence variants of a polypeptide, such as an antibody, the location of the mutation site and the nature of the mutation will depend on characteristic(s) to be modified. The sites for mutation can be modified individually or in series, e.g., by substituting first with conservative amino acid choices and then with more radical selections depending upon the results achieved, or deleting the target residue.

A useful method for identification of specific residues or regions for mutagenesis in a polypeptide is called "alanine scanning mutagenesis" and is described, for example, by Cunningham and Wells (Science 244:1081-1085, 1989). Here, a residue or group of target residues are identified (e.g., charged residues such as arg, asp, his, lys, and glu) and replaced by a neutral or negatively charged amino acid (most desirably alanine or polyalanine) to affect the interaction of the amino acids with the surrounding aqueous environment in or outside the cell. The domains demonstrating functional sensitivity to the substitutions then are refined by introducing further or other variants at or for the sites of substitution. Thus, while the site for introducing an amino acid sequence variation is predetermined, the nature of the mutation need not be predetermined. For instance, to optimize the performance of a mutation at a given site, alanine scanning or random mutagenesis may be conducted at the target codon or region and the expressed variants are screened for, e.g., the ability to induce apoptosis of a neoplastic cell and not a non-neoplastic cell, or to inhibit the proliferation of a neoplastic cell and not a non-neoplastic cell.

The sites of greatest interest for substitutional mutagenesis include sites identified as affecting the biological activity of a polypeptide. These sites, especially those falling within a sequence of at least three other identically conserved sites, may be substituted in a relatively conservative manner. For instance, ala may be substituted with val, leu, or ile; arg may be substituted with lys, gin, or asn; asn may be substituted with gin, his, lys, or arg; asp may be substituted with glu; cys may be substituted with ser; gin may be substituted with asn; glu may be substituted with asp; gly may be substituted with pro; his may be substituted with asn, gin, lys, or arg; ile may be substituted with leu, val, met, ala, or phe; leu may be substituted with ile, val, met, ala, or phe; lys may be substituted with arg, gin, or asn; met may be substituted with leu, phe, or ile; phe may be substituted with leu, val, ile, or ala; pro may be substituted with gly; ser may be substituted with thr; thr may be substituted with ser; trp may be substituted with tyr; tyr may be substituted with trp, phe, thr, or ser; and val may be substituted with ile, leu, met, or phe.

Conjugation of a Polypeptide with a Detectable Agent

If desired, a PAM-1 antibody, a fragment thereof, or the novel CFR-1 isoform described herein may be linked to a detectable agent to facilitate the purification of the polypeptide as well as the diagnosis, monitoring, or treatment of a neoplasm or a pre-cancerous lesion in a mammal in need thereof. The selection of suitable detectable agent will depend on the intended use of the polypeptide and will be apparent to those of ordinary skill in the art. Detectable agents according to the invention include, for example, protein purification tags, cytotoxins, enzymes, paramagnetic labels, enzyme substrates, co-factors, enzyme inhibitors, dyes, radionuclides, chemiluminescent labels, fluorescent markers, growth inhibitors, and biotin.

A protein purification tag may be conjugated to a PAM-1 antibody, fragment thereof, or the novel CFR-1 isoform described herein to facilitate isolation of the polypeptide. Examples of tags that can be used include His-tags, HA-tags, FLAG®-tags, and c-Myc tags. An enzymatic or a chemical cleavage site may be engineered between the polypeptide and the tag moiety so that the tag can be removed following purification. Suitable toxins include diphtheria toxin, *Pseudomonas* exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Examples of suitable radioisotopic labels include $^3$H, $^{125}$I, $^{131}$I, $^{32}$P, $^{35}$S, and $^{14}$C. Desirably, the radioisotope will emit in the 10-5,000 kev range, more desirably 100-500 kev. Paramagnetic isotopes may also be conjugated to the polypeptide and used in vivo for the diagnosis and treatment of cancer. The use of such conjugated polypeptides may be for in vivo nuclear magnetic resonance imaging. Such methods are known in the art (see, for example, Schaefer et al., JACC 14:472-480, 1989; Shreve et al., Magn. Reson. Med. 3:336-340, 1986; Wolf, Physiol. Chem. Phys. Med. NMR 16:93-95, 1984; Wesbey et al., Physiol. Chem. Phys. Med. NMR 16:145-155, 1984; and Runge et al., Invest. Radiol. 19:408-415, 1984). Alternatively, a radiolabeled polypeptide may also be used in radioimmunoguided surgery (RIGS), which involves the surgical removal of any tissue the labeled antibody binds to. Thus, the labeled polypeptide guides the surgeon towards neoplastic tissue by distinguishing it from non-neoplastic tissue. Radiolabels useful for tumor imaging are preferably short-lived radioisotopes. Various radioactive metals with half-lives ranging from 1 hour to 11.4 days are available for conjugation to antibodies, such as scandium-47 (3.4 days), gallium-67 (2.8 days), gallium-68 (68 minutes), technetium-99m (6 hours), indium-111 (3.2 days), and radium-223 (11.4 days), of which gallium-67, technetium-99m, and indium-111 are preferable for gamma camera imaging, gallium-68 is preferable for positron emission tomography, and scandium-47 and radium-223 (and other alpha-emitting radionuclides) are preferable for tumor therapy.

Examples of suitable fluorescent markers include fluorescein, isothiocyalate, rhodamine, phycoerythrin, phycocyanin, allophycocyanin, ophthaldehyde, and fluorescamine. Examples of chemiluminescent markers include a luminal label, isoluminal label, aromatic acridinium ester label, imidazole label, acridinium salt label, oxalate ester label, luciferin label, luciferase label, and aequorin label. Those of ordinary skill in the art would know of other suitable labels, which may be employed in accordance with the present invention. Conjugation of these detectable agents to a polypeptide described herein, such as PAM-1 antibodies, fragments thereof, and the novel isoform of CFR-1, can be accomplished using standard techniques known in the art. Typical antibody conjugation techniques are described by Kennedy et al. (Clin. Chim. Acta 70, 1-31, 1976) and Schurs et al. (Clin. Chim. Acta 81, 1-40, 1977) and include, for example, the glutaraldehyde method, the periodate method, the dimaleimide method, the m-maleimidobenzyl-N-hydroxy-succinimide ester method. Antibodies may be radiolabeled by any of several techniques known to the art, described, for example, in U.S. Pat. No. 4,444,744. All of these methods are incorporated by reference herein.

In all methods of treatment of the present invention, it is understood that mixtures of different or the same labeled antibodies specific to different antigens or different epitopes of the same antigen associated with the same or different tumor or tumor cell types may be used. Such a combination may enhance detection, localization, and/or therapy in certain cases, and can also increase the range of a broad screen for more than one neoplasm or type of neoplasm.

Polypeptides Conjugated to Anti-Tumor Agents

Although a PAM-1 antibody or fragment thereof can induce apoptosis of neoplastic cells, inhibit cellular proliferation of neoplastic cells, or both, the polypeptide may in addition be conjugated to an agent that kills neoplastic cells or that inhibits their proliferation. The targeting ability of the PAM-1 antibody or fragment thereof, results in the delivery of the cytotoxic or anti-proliferative agent to the tumor to enhance the destruction of the tumor. The polypeptide therefore may be used for the treatment and prevention of a neoplasm or pre-cancerous lesion in a mammal, such as a human patient. The cytotoxic agent linked to the polypeptide may be any agent that destroys or damages a tumor cell or tumor to which the polypeptide has bound. Examples of such agents include chemotherapeutic agents or radioisotopes, enzymes which activate a pro-drug, or a cytokine.

Suitable chemotherapeutic agents are known to those skilled in the art and include, for example, taxol, mithramycin, deoxyco-formycin, mitomycin-C, L-asparaginase, interferons (especially IFN-alpha), etoposide, teniposide, anthracyclines (e.g., daunomycin and doxorubicin), methotrexate, vindesine, neocarzinostatin, cis-platinum, chlorambucil, cytosine arabinoside, 5-fluorouridine, melphalan, ricin, and calicheamicin. The chemotherapeutic agents may be conjugated to the antibody using conventional methods known in the art.

Suitable radioisotopes for use as cytotoxic agents are also known to those skilled in the art and include, for example, $^{131}$I, or an astatine such as $^{211}$At. These isotopes may be attached to the polypeptide, either covalently or non-covalently, using conventional techniques known in the art.

Alternatively, the cytotoxic agent may also be an enzyme, which activates a pro-drug. This allows the conversion of an inactive pro-drug to its active, cytotoxic form at the tumor site and is called "antibody-directed enzyme pro-drug therapy" (ADEPT). Thus, the polypeptide-enzyme conjugate may be administered to the patient and allowed to localize in the region of the tumor to be treated. The pro-drug is then administered to the patient such that conversion to the cytotoxic drug is localized in the region of the tumor to be treated under the influence of the localized enzyme. An exemplary enzyme is bacterial carboxypeptidase G2 (CPG2) the use of which is described in, for example, WO 88/07378. The polypeptide-enzyme conjugate may, if desired, be modified in accordance with the teaching of WO 89/00427, such as to accelerate its clearance from areas of the body that are not in the vicinity of a neoplasm. The polypeptide-enzyme conjugate may also be used in accordance with WO 89/00427, for example, by providing an additional component, which inactivates the enzyme in areas of the body that are not in the vicinity of the tumor.

As another alternative, the cytotoxic agent conjugated to a PAM-1 antibody or fragment thereof may also be a cytokine such as interleukin-2 (IL-2), interleukin-4 (IL-4), or tumor necrosis factor alpha (TNF-alpha). The polypeptide targets the cytokine to the tumor so that the cytokine mediates damage to or destruction of the tumor without affecting other tissues. The cytokine may be fused to the polypeptide at the DNA level using conventional recombinant DNA techniques.

In addition, any inhibitor of cell proliferation. e.g., genistein, tamoxifen, or cyclophosphamide, may be conjugated with a polypeptide described herein.

Dosage

With respect to the therapeutic methods of the invention, it is not intended that the administration of a polypeptide of the invention to a patient be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to decrease the number of neoplastic cells by inducing apoptosis of neoplastic cells, by inhibiting proliferation of tumor cells, or both. The compound(s) may be administered to the patient in a single dose or in multiple doses. When multiple doses are administered, the doses may be separated from one another by, for example, one day, two days, one week, two weeks, or one month. For example, the polypeptide (e.g., a PAM-1 antibody, fragment thereof, the novel CFR-1 isoform described herein) a vector including a nucleic acid molecule that encodes this novel isoform of CFR-1, maybe administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. The precise dose will vary dependent on the polypeptide or vector used, the density, on the tumor surface, of the ligand to which the polypeptide binds, and the rate of clearance of the polypeptide. For example, the dosage of a PAM-1 antibody or novel isoform of CFR-1 described herein can be increased if the lower dose does not provide sufficient anti-neoplastic activity. Conversely, the dosage a PAM-1 antibody or novel isoform of CFR-1 described herein can be decreased if the neoplasm is cleared from the patient.

While the attending physician ultimately will decide the appropriate amount and dosage regimen, a therapeutically effective amount of a polypeptide, such as a monoclonal antibody or a fragment thereof, may be, for example, in the range of about 0.1 mg to 50 mg/kg body weight/day or 0.70 mg to 350 mg/kg body weight/week. Desirably a therapeutically effective amount is in the range of about 0.50 mg to 20.0 mg/kg, and more desirably in the range of about 0.50 mg to 15.0 mg/kg, for example, about 0.2, 0.3, 0.5, 1.0, 1.5, 2.0, 2.5, 3.0, 3.5, 4.0, 4.5, 5.0, 5.5, 6.0, 7.0, 8.0, 8.5, 9.0, 10.0, 11.0, 12.0, 13.0, 14.0, or 15.0 mg/kg body weight administered daily, every other day, or twice a week.

For instance, a suitable dose is an amount of the polypeptide that, when administered as described above, is capable of inducing apoptosis, and is at least 20% above the basal (i.e., untreated) level. In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. According to this invention, the administration of the polypeptide can induce neoplastic cell apoptosis by at least 20%, 40%, 50%, or 75% above that of an untreated control as measured by any standard assay known in the art. More desirably, apoptosis is induced by 80%, 90%, 95%, or even 100% above that of an untreated control. Alternatively, the administration of the polypeptide can inhibit neoplastic cell proliferation by at least 20%, 40%, 50%, or 75% below that of an untreated control as measured by any standard assay known in the art. More desirably, proliferation is inhibited by 80%, 90%, 95%, or even 100% below that of an untreated control. Most desirably, the polypeptide can simultaneously inhibit proliferation and induce apoptosis of neoplastic cells relative to untreated control cells. Such responses can be monitored by any standard technique known in the art, including those described herein. In general, for pharmaceutical compositions, the amount of antibody present in a dose ranges from about 25 μg to 5 mg per kg of host. Suitable dose sizes will vary with the size of the patient, but will typically range from about 0.1 mL to about 5 mL.

In addition, a DNA vaccine including a plasmid vector or a viral vector which includes a nucleotide sequence encoding SEQ ID NO:6, or a fragment thereof, may be used to induce a tumor-specific immune response in a patient. This immune response, for example, results in the formation of antibodies that specifically bind to a neoplasm or a pre-cancerous lesion. In general, an effective dose range of about 1 ng to 5 mg, 100 ng to 2.5 mg, 1 μg to 750 μg, and preferably about 10 μg to 300 μg of DNA is administered directly into muscle tissue. Subcutaneous injection, intradermal introduction, impression through the skin, and other modes of administration such as intraperitoneal, intravenous, or inhalation delivery are also suitable. In addition, booster vaccinations may be provided.

Formulation of Pharmaceutical Compositions

A PAM-1 antibody, fragment thereof, or the novel CFR-1 isoform described therein may be administered by any suitable means that results in a concentration having anti-neoplastic properties upon reaching the target region. The polypeptide may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott, Williams & Wilkins, 2000 and Encyclopedia of Pharmaceutical Technology, eds. J. Swarbrick and J. C. Boylan, 1988-1999, Marcel Dekker, New York).

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. If the neoplastic cells are in direct contact with the blood (e.g., leukemias), or if the tumor is only accessible by the bloodstream then the intravenous (I.V.) route may be used. In cases in which tumors grow in confined spaces such as the pleural cavity or the peritoneal cavity, the polypeptide may be directly administered into the cavity rather than into the blood stream. The formulation and preparation of such compositions are well known to those skilled in the art of pharmaceutical formulation. Formulations can be found, for example, in Remington (The Science and Practice of Pharmacy (20th ed.), ed. A. R. Gennaro, Lippincott, Williams & Wilkins, 2000 and Encyclopedia of Pharmaceutical Technology, eds. J. Swarbrick and J. C. Boylan, 1988-1999, Marcel Dekker, New York).

Diagnosis and Monitoring Cancer Progression

As discussed above, aspects of the present invention are directed to methods of detecting or diagnosing a neoplasm in a mammal, preferably a human patient. Typically, any neoplasm which is specifically bound by a PAM-1 antibody, or a fragment thereof, may be detected either in vitro or in vivo according to the methods of the present invention. Such a neoplasm may be one that expressed the isoform of CFR-1 that is bound by a PAM-1 antibody. Furthermore, a cell which expressed the isoform of CFR-1 described herein is likely to be a neoplastic cell or a cell in a pre-cancerous lesion. Thus, the isoform of CFR-1 recognized by a PAM-1 antibody may be used as a marker to detect whether a patient has neoplasm or is likely to develop a neoplasm.

PAM-1 antibodies and fragments thereof are particularly useful because they specifically bind neoplastic, cells in pre-cancerous lesions, as well as proliferating malignant cells, and not normal cells and normal proliferating cells or tissue. Accordingly, such polypeptides can bind to neoplastic cells within the tumor, but not the normal surrounding tissue, thus allowing the detection, the treatment, or both, of a neoplasm in a mammal. For instance, PAM-1 antibodies and fragments thereof may be used to determine if a biopsy removed the entire tumor by verifying that no cells bound by the polypeptide remain in the patient or, by verifying that tumor removed from the patient is entirely surrounded by cells that are not bound by the polypeptide.

It is understood that to improve the sensitivity of detection, multiple neoplastic markers may be assayed within a given sample or individual. Thus, polypeptides such as antibodies or functional fragments specific for different antigens may be combined within a single assay, or in multiple assays. Further, multiple primers or probes specific to neoplasms may be used concurrently. The selection of markers may be based on routine experiments to determine combinations that results in optimal sensitivity.

In Vitro Detection of a Neoplasm

In general, the diagnosis of a neoplasm in a mammal involves obtaining a biological sample from the mammal (e.g., human patient), contacting such sample with a PAM-1 antibody or fragment thereof, detecting, in the test sample, the level of reactivity or binding of the polypeptide to neoplastic cells relative to a control sample, which corresponds to non-neoplastic cells derived from healthy tissue from the mammal in which the cancer is being diagnosed or from another patient known not to have a neoplasm. Thus, the novel isoform of CFR-1 described herein, as well as the PAM-1 antibodies of the invention are particularly useful for the detection of early stage tumors or metastases, which are otherwise undetectable. Accordingly, in addition to diagnosing a neoplasm in a patient, the methods of this invention may also be used to monitor progression of a neoplasm in a mammal. The polypeptides described herein therefore may be used as markers for the progression of a neoplasm. For this purpose, the assays described below, which are used for the diagnosis of a neoplasm, may be performed over time, and the change in the level of reactive polypeptide(s) evaluated. For example, the assays may be performed every 24-72 hours for a period of 6 months to 1 year, and thereafter performed as needed. In general, a neoplasm is progressing in those patients in whom the level of bound PAM-1 antibody detected increases over time or where the expression of the isoform of CFR-1 described herein increases over time. In contrast, the neoplasm is not progressing when the level of bound PAM-1 antibody either remains constant or decreases with time or where the expression of the isoform of CFR-1 described herein descreases over time. Alternatively, as is noted above, the CFR-1 isoform described herein and the PAM-1 antibodies may be used to determine the presence of tumor cells in the mammal following tumor resection by surgical intervention to determine whether the tumor has been completely removed from the mammal.

Desirably, the polypeptide is linked to a detectable agent, which facilitates detection, or measurement of polypeptide reactivity. The biological sample is any biological material which may contain neoplastic or proliferating cells and includes, for example, blood, saliva, tissue, serum, mucus, sputum, urine, or tears. The biological sample may also be a tissue section, which may be fixed tissue, fresh tissue, or frozen tissue. A neoplasm is detected or diagnosed in the mammal from which the sample was obtained if there is an increase in the level of reactivity of a PAM-1 antibody or fragment thereof with the biological sample, or increased expression of the isoform of CFR-1 described herein over the control sample. Such increase is at least 10%, 20%, 30%, 40%, 50%, or more than 50% over control levels. The level of binding or reactivity can be determined by any method known in the art and is described in further detail below.

In Vitro Diagnostic Assays

The diagnosis of neoplasms or a pre-cancerous lesion using a polypeptide of the invention may be performed by any method known to those of ordinary skill in the art for using a binding agent to detect polypeptide markers, e.g., the isoform of CFR-1 recognized by a PAM-1 antibody, in a sample. See, e.g., Harlow and Lane, Using Antibodies: A Laboratory Manual, Cold Spring Harbor Laboratory Press, N.Y., 1999. For example, the polypeptide may be used for enzyme-linked immunosorbent assay (ELISA), Western blotting, or in situ detection of tumor cells in a tissue sample. For instance, the ELISA assay typically involves the use of a polypeptide, such as an antibody, immobilized on a solid support to bind to the tumor cells in the biological sample. The bound tumor cell may then be detected using a detection reagent that contains a reporter group and that specifically binds to the antibody/tumor cell complex. Such detection reagents include, for example, any binding agent that specifically binds to a PAM-1 antibody or fragment thereof, such as an anti-immunoglobulin, protein G, protein A, or a lectin. Alternatively, a competitive assay may be utilized, in which the polypeptide is a PAM-1 antibody and in which the antigens, to which the antibody is specific to is labeled with a reporter group and allowed to bind to the immobilized antibody after incubation of the antibody with the biological sample. The extent to which components of the sample inhibit the binding of the labeled antigens to the antibody is indicative of the reactivity of the sample with the immobilized antibody. Diagnosis of a neoplasm in a patient, or the identification of a pre-cancerous lesion in a patient, may also be determined by a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group. For example, to determine the presence or absence of a neoplasm, such as a stomach adenocarcinoma, the signal detected from the reporter group that remains bound to the solid support is generally compared to a signal that corresponds to a predetermined cut-off value. The cut-off value for the detection of a neoplasm is the average mean signal obtained when the antibody is incubated with samples from patients without a neoplasm.

The method employed for detecting the reporter group depends upon the nature of the reporter group. For radioactive groups, scintillation counting or autoradiographic methods may be used. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a defined period of time), followed by spectroscopic or other analysis of the reaction products.

PAM-1 antibodies and fragments thereof may also be employed histologically for in situ detection or quantitative determination of tumor cells, for example, by immunofluorescence or immunoelectron microscopy. In situ detection or determination may be accomplished by removing a tissue specimen from a patient and allowing a labeled antibody to bind to any tumor cell in the specimen. Using such a procedure not only allows the detection of neoplastic or a pre-cancerous lesion in a sample, but also allows for the determination of their spatial distribution. As another example, the biological sample can be a smear of biological material containing neoplastic cells on a slide, and the detection of neoplastic cells in the biological material is achieved by examining the smear with a microscope or by fluocytometry.

In Vivo detection of a Neoplasm

Alternatively, A PAM-1 antibody may also be used in vivo for detecting and localizing a neoplasm or pre-cancerous lesion. Such a method may involve injecting a mammal, desirably a human subject, parenterally with a PAM-1 antibody or fragment thereof, which has been labeled with a detectable agent, and is described, for instance, in U.S. Pat. No. 4,444,744. For example, the antibody or antibody fragment can be radiolabeled with a pharmacologically inert radioisotope and administered to the patient. The activity of the radioisotope can be detected in the mammal using a photoscanning device, and an increase in activity relative to a control reflects the detection and localization of a neoplasm.

Treatment

In addition to the diagnosis and monitoring of neoplasms in mammals, the present invention also features methods for treating neoplasms in a mammal, desirably a human patient. The method generally involves the administration of a biologically effective amount of a polypeptide, e.g., the isoform of CFR-1 described herein, or a PAM-1 antibody or fragment thereof. The polypeptide is typically administered to the mammal by means of injection using any routes of administration such as by intrathecal, subcutaneous, submucosal, or intracavitary injection as well as for intravenous or intraarterial injection. Thus, the polypeptide may be injected systemically, for example, by the intravenous injection of the polypeptide into the patient's bloodstream or alternatively, the polypeptide can be directly injected at the site of the neoplasm or at a location in proximity to the neoplastic cells.

For example, purified polypeptides corresponding to all or a part of the CFR-1 isoform described herein may be used to reinforce and amplify antibody formation and, therefore, may be used to induce elevated apoptosis of the tumor cells or for a complement-mediated lysis. Further, given CFR-1's likely function in nutrient uptake, the cells expressing this tumor-specific isoform of CFR-1 would "starve," since blocking of the receptor leads to growth arrest.

In view of its tissue distribution, the isoform of CRF-1 described herein is particularly suitable for treating the following tumors and pre-cancerous lesions: dysplasia of the gastric mucosa, interstitial metaplasia of the stomach, inflammation of the gastric mucosa which is associated with the bacteria *Helicobacter pylori*, tubular and tubulovillous adenomas of the stomach, tubular adenoma of the colon, villous adenoma of the colon, dysplasia in ulcerative colitis, Barrett's dysplasia, Barrett's metaplasia of the esophagus, cervical intraepithelial neoplasia I, cervical intraepithelial neoplasia II, cervical intraepithelial neoplasia III, squamous epithelial metaplasia, squamous epithelial dysplasia of the bronchus, low grade and high grade prostate intraepithelial neoplasia (PIN), breast ductal carcinoma in situ (D-CIS), breast lobular carcinoma in situ (L-CIS), Barrett's tumors, and tumors of the esophagus, stomach, intestine, rectum, liver, gallbladder, pancreas, lungs, bronchi, breast, cervix, prostate, heart, ovary, and uterus.

Furthermore, PAM-1 antibodies and fragments thereof may also be used in methods to treat neoplasms or kill cells of a pre-cancerous lesion. As discussed above, binding of a PAM-1 antibody or fragment thereof to a neoplastic or a cell of a pre-cancerous lesion results in an induction in apoptosis, a reduction in cellular proliferation, or both relative to the control sample. Alternatively, the antibodies may also activate the complement pathway, which ultimately causes holes to be punctured into the cellular membrane, resulting in cell death.

If desired, the PAM-1 antibody or fragment thereof may also be conjugated to drugs or toxins as described above. Once attached to the cell surface, the conjugate may be engulfed into the cell cytoplasm where cell enzymes cleave, and, thus, activate or free the drugs or toxins from the conjugate. Once released, the drugs or toxins damage the cell and irreversibly induce cell death. With respect to radiolabeled antibodies, binding to neoplastic cells or cells of a pre-cancerous lesion and the resulting emission of radiation, at a short distance from the cell DNA, produces damage to the latter thus inducing cell death in the next replication round. For example, after a neoplasm has been detected and localized in a subject, a higher dose of labeled antibody, generally from 25 to 250 mCi for $^{131}$I, and preferably from 50 nCi to 150 mCi per dose, based on a 70 kg patient weight, is injected. Injection may be intravenous, intraarterial, intralymphatic, intrathecal, or intracavitary, and may be repeated more than once. It may be advantageous for some therapies to administer multiple, divided doses of radiolabeled polypeptides or polypeptide mixtures, e.g., in the range of 20-120 mCi (70 kg patient), thus providing higher cell-killing doses to the neoplasm usually without effecting a proportional increase in radiation of normal tissues Therapy using labeled polypeptides is advantageously used as a primary therapeutic treatment, but may also be used in combination with other anti-neoplastic therapies, e.g., 25 radiation and chemotherapy, and as an adjunct to surgery. The administration of such conjugated polypeptides is particularly useful in the case where small metastases cannot be surgically removed.

Combination of a Polypeptide with other Anti-Neoplastic Therapies

Chemotherapeutic agents and/or radiation and/or surgical removal of the neoplasm can optionally be combined with any of the methods of the present invention. Classes of compounds that can be used as the chemotherapeutic agent include: alkylating agents, antimetabolites, natural products and their derivatives, hormones and steroids (including synthetic analogs), and synthetics. Examples of alkylating agents (e.g., nitrogen mustards, ethylenimine derivatives, alkyl sulfonates, nitrosoureas and triazenes) include Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide. Antimetabolites (including folic acid antagonists, pyrimidine analogs, purine analogs and adenosine deaminase inhibitors) may include, for example, Methotrexate, 5-Fluorouracil, Floxuridine, Cytarabine, 6-Mercaptopurine, 6-Thioguanine, Fludarabine phosphate, Pentostatine, and Gemcitabine. Natural products and their derivatives (including vinca alkaloids, antitumor antibiotics, enzymes, lymphokines and epipodophyllotoxins) may also be used and include, for example, Vinblastine, Vincristine, Vindesine, Bleomycin, Dactinomycin, Daunorubicin, Doxorubicin, Epirubicin, Idarubicin, paclitaxel (paclitaxel is commercially available as Taxol®), Mithramycin, Deoxycoformycin, Mitomycin-C, L-Asparaginase, Interferons (especially IFN-alpha), Etoposide, and Teniposide. Hormones and steroids (including synthetic analogs) include, for example, 17-alpha-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, or Zoladex. Exemplary synthetics (including inorganic complexes such as platinum coordination complexes) include Cisplatin, Carboplatin, Hydroxyurea, Amsacrine, Procarbazine, Mitotane, Mitoxantrone, Levamisole, and Hexamethylmelamine.

Methods and dosages for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the disclosure of which is incorporated herein by reference.

Identification of Therapeutic Compounds

The novel isoform of CFR-1 described herein may be used to produce an anti-neoplastic or anti-proliferative agent, in which compounds that are potentially effective against tumors are assayed for their ability to specifically bind to the novel CFR-1 isoform described herein. Upon a positive result, i.e., upon the occurrence of binding, this compound may be assayed for its ability to induce apoptosis in neoplastic cells or cells of a pre-cancerous lesion or its ability to alter the rate of proliferation of such cells using the methods described herein. Once such a compound has been characterized, it may be included in a pharmaceutical composition for the treatment of a neoplastic disease.

Test Extracts and Compounds

In general, compounds that alter a biological activity of the novel isoform of CFR-1 described herein are identified from large libraries of both natural products, synthetic (or semi-synthetic) extracts or chemical libraries, according to methods known in the art. For example, such compounds may be human antibodies, murine antibodies, humanized antibodies of any arbitrary species, as well as antibody fragments such as Fab and F(ab)$_2$ and/or Fab' fragments obtained by proteolytic cleavage of antibodies. These also include single strand antibodies and/or tetrameric and/or dimeric antibody forms and/or bispecific antibodies.

Those skilled in the art will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from, for example, Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, including, but not limited to, Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art (e.g., by combinatorial chemistry methods or standard extraction and fractionation methods). Furthermore, if desired, any library or compound may be readily modified using standard chemical, physical, or biochemical methods.

In addition, those skilled in the art readily understand that methods for dereplication (e.g., taxonomic dereplication, biological dereplication, and chemical dereplication, or any combination thereof) or the elimination of replicates or repeats of materials already known for their effects on CFR-1 should be employed whenever possible.

When a crude extract is found to alter a biological activity of the novel CFR-1 isoform described herein, further fractionation of the positive lead extract is necessary to isolate chemical constituents responsible for the observed effect. Thus, the goal of the extraction, fractionation, and purification process is the careful characterization and identification of a chemical entity within the crude extract having activities that alter a biological activity of the novel CFR-1 isoform described herein. The same in vivo and in vitro assays described herein for the detection of activities in mixtures of compounds can be used to purify the active component and to test derivatives thereof Methods of fractionation and purification of such heterogenous extracts are known in the art.

The following examples are provided for the purpose of illustrating the invention and should not be construed as limiting.

EXAMPLE 1

Materials and Methods

Cell Culture and Antibody Purification

In all assays, the known gastric adenocarcinoma cell line 23132 was used, which is deposited under No. ACC201 at the DSMZ-German Collection of Microorganisms and Cell Cultures GmbH, Mascheronder Weg 1b, 38124 Braunschweig, Germany. Cells were grown to 80% confluency in RPMI-1640 (PAA, Vienna, Austria) supplemented with 10% FCS and penicillin/streptomycin (1% for both). For the assays described, cells were detached with trypsin/EDTA and washed twice with phosphate buffered saline (PBS) before use. The PAM-1 antibody producing human hybridoma cell line 103/51 was grown in cell culture flasks (175 $cm^2$) in serum free AIM®V medium (Life Technologies, Karlsruhe, Germany). Cell culture supernatant was collected and the IgM antibody PAM-1 was purified on a HiTrap™ IgM affinity column (Amersham Pharmacia Biotech, Freiburg, Germany) using an FPLC system. The antibody was eluted with 20 mM sodium phosphate, pH 7.5 in 30% isopropanol. Buffer exchange with PBS was performed using NAP®-10 columns (Amersham Pharmacia Biotech). Purity was determined by SDS gel electrophoresis and Western blotting.

Preparation of Membrane Extracts

Isolation of membrane proteins from tumor cells was performed as described by Hensel et al. (Int. J. Cancer 81:229-235 (1999)), using cell line 23132. In short, confluent tumor cells were washed twice with phosphate buffered saline ("PBS"), harvested with a cellscraper and centrifuged, and resuspended in hypotonic buffer (20 mM HEPES, 3 mM KCl, 3 mM $MgCl_2$). After 15 minutes incubation on ice, followed by sonification for 5 minutes, the nuclei were pelleted by centrifugation at 10,000 g for 10 minutes. The supernatant was centrifuged for 30 min at 100,000 g in a swing-out rotor to pellet membranes. After washing the pellet with hypotonic buffer, it was resuspended in membrane lysis buffer (50 mM HEPES pH 7.4, 0.1 mM EDTA, 10% glycerol, and 1% TRITON X-100). A protease inhibitor (Boehringer, Mannheim, Germany) was added to all solutions.

Western Blotting

10% reducing SDS-PAGE (sodium dodecyl sulfate-polyacrylamide gel electrophoresis) gels and Western blotting of proteins were performed using standard protocols as described, for example, in Hensel et al. (Int. J. Cancer 81:229-235 (1999)). In short, blotted nitrocellulose membranes were blocked with PBS containing 2% low fat milk powder, followed by a one-hour incubation with 10 µg/ml purified primary antibody, e.g., 103/51 or control antibody (intact or fragmented). The secondary antibody (peroxidase-coupled rabbit anti-human IgM antibody (Dianova, Hamburg, Germany)) was detected with the SUPERSIGNAL chemiluminescence kit from Pierce (KMF, St. Augustin, Germany). After three washes with PBS+0.05% Tween-20, the blots were incubated with the secondary antibody (peroxidase-coupled rabbit antihuman IgM antibody (Dianova, Hamburg, Germany)). The reaction was detected with the aid of the SUPERSIGNAL chemiluminescence kit from Pierce (KMF, St. Augustin, Germany).

Purification of the Atigen 103/51

Purification of the antigens was performed by column chromatography using a Pharmacia (Freiburg, Germany) FPLC unit. For size exclusion chromatography, a Pharmacia SUPERDEX 200 column (XK16/60) was loaded with 5 mg membrane preparation and run with buffer A (100 mM Tris/Cl, pH 7.5, 2 mM EDTA, 40 mM NaCl, 1% Triton X-100). Then, the eluate was fractionated and examined in Western blot analysis for reaction with antibody 103/51. Positive fractions were loaded on a MONOQ (5/5) column using buffer A. The bound proteins were eluted with a linear gradient using buffer B (100 mM Tris/Cl, pH 7.5, 1 M NaCl, 2 mM EDTA, 1 M NaCl, 1% Triton X-100), fractionated and examined in Coomassie-stained SDS-PAGE and Western blot analysis. Positive bands were cut out from gel and sequenced or used for immunization of mice.

MALDI Peptide Mapping

The band of interest was excised from the SDS-PAGE gel and cut into small pieces of about 1 mm×1 mm. Gel pieces were washed, reduced with DTT (dithiothreitol), S-alkylated with iodoacetamide, and in-gel digested with trypsin (unmodified, sequencing grade, Boehringer) as described, e.g., in Shevchenko et al. (Anal.Chem. 68:850-858 1996)). After 3 hours of digestion at 37° C., 0.3 µl of the digest solution was removed and subjected to MALDI peptide mass mapping on a Bruker Reflex MALDI-TOF equipped with delayed extraction (Bruker-Franzen, Bremen, Germany). The thin film technique was adopted for sample preparation (Jensen et al., Rapid. Commun. Mass. Spectrom. 10:1371-1378 (1996)). The tryptic peptide masses were used to search a non-redundant protein sequence database by the PeptideSearch software program developed in-house.

Cloning of CFR-1 Anti-Sense Vector and Transfection

RNA isolation, cDNA synthesis, and PCR were performed using standard methods, as described, e.g., in Hensel et al. (Int.J.Cancer 81:229-235 (1999)). In short, for PCR for amplification of a 897 bp fragment ranging from basepairs 802 to 1699, the following primers were used: CFR-For 5' GCTTGGAGAAAGGCCTGGTGAA 3' (SEQ ID NO:9), CFR-Rev 5' TGGCACTTGCGGTACAGGACAG 3' (SEQ ID NO:10). Amplification was performed using the following cycle profile: 95° C., 2 minutes, followed by 35 cycles of 94° C., 30 seconds; 60° C., 30 seconds; 72° C., 60 seconds, and a final extension of 72° C. for 4 minutes. Cloning into the pCR-Script Amp SK (+) vector and DNA sequencing were performed as described, e.g., in Hensel et al. (Int. J. Cancer 81:229-235 (1999)). The insert was subcloned into the pHook-2 vector (Invitrogen, Leek, Netherlands), and the accuracy of the cloning was verified by sequencing.

Transfection of cell line 23132 with pHOOK2-antiCFR-1 was accomplished with PRIMEFECTOR reagent (PQLab, Erlangen, Germany) according to supplier's manual. In short, plasmid DNA was diluted to 10 µg/ml and the PRIMEFECTOR reagent was added in a 1:10 ratio to a serum-free growth medium. Diluted plasmid DNA (450 µl), diluted PRIMEFECTOR reagent (90 µl), and serumfree medium (460 µl) were mixed and incubated at room temprature ("RT"). 60-milliliter cell culture plates (70% confluent) were washed two times with serumfree medium, and then the PRIMEFECTOR/DNA mixture was added dropwise. Cells were incubated 18 hours at 37° C. and 7% $CO_2$, then serumfree growth medium was replaced with growth medium containing 10% FCS, and cells were incubated another 24 hours before studying CFR-1 expression.

Flow Cytometry

The cell line 23132 was detached from culture plates by trypsin/EDTA 48 hours after transfection, washed and subsequently incubated on ice with antibody 103/51 and a human isotype-matched control antibody (Chromopure human IgM) for 15 minutes, followed by incubation with a FITC-labeled rabbit anti-human IgM antibody (Dianova) for 15 minutes on ice. Antibodies were optimally diluted in PBS containing 0.01% sodium azide. Cells were analyzed by flow cytometry (FACScan; Becton Dickinson, USA).

Glycosidase Assays

Detached and washed cells were resuspended in RPMI-1640 containing 10% FCS and incubated for 1 hour on ice, then counted, and cytospins were prepared. After air-drying, cytospin preparations were acetone-fixed (10 min), washed, and incubated with 20 µU/ml O-glycosidase or 5 mU/ml N-glycosidase (Boehringer) for 4 hours at 37° C. Slides then were washed and immunohistochemically stained.

For deglycosylation of membranous proteins, membrane extracts were incubated for 16 hours at 37° C. with 1 mU/ml N-glycosidase diluted in deglycosylation buffer (50 mM $PO_4$-Buffer, pH 7.4). As a control, extracts were incubated with deglycosylation buffer alone. Extracts then were separated by SDS-PAGE and Western blots were performed as described above.

Production of Murine Monoclonal Antibodies

BALB/c mice were immunized two times within 17 days with 5 µg purified antigen of antibody 103/51, and killed 4 days after the second immunization. Spleens were disrupted mechanically and fused with $1 \times 10^7$ NSO cells as described, e.g., in Vollmers et al. (Cell 40:547-557 (1985)). Antibody-producing hybridomas were tested through immunohistochemical staining and reaction in Western blot analysis. Clone 58/47-69 with positive reactivity was used for further experiments.

Immunohistochemical Staining Of Paraffin Sections

Paraffin-embedded human gastric mucosa and tumor were sectioned (5 μm), deparaffinized, and blocked with BSA (bovine serum albumin) (15 mg/ml) diluted in PBS for 30 minutes. The sections were incubated with supernatant of hybridoma 103/51, or 58/47-69, Ki67 (Loxo, Dossenhein, Germany) or mouse anti-cytokeratin 8 antibody diluted 1:15 with BSA/PBS (Dako, Hamburg, Germany) for 2 to 2.5 hours in a humidified incubator. The sections then were washed three times with Tris/NaCl, followed by incubation with peroxidase-labeled rabbit anti-human or rabbit anti-mouse conjugate (Dako) diluted 1:50 in PBS containing rabbit serum (for antibody 103/51) or in PBS containing human AB plasma (for antibody 58/47-69 and anti-cytokeratin). After washing three times with Tris/NaCl and incubation in PBS for 10 min staining was performed with diaminobenzidine (0.05%)-hydrogen peroxide (0.02%) for 10 min at RT. The reaction was stopped under running tap water, and sections were counterstained with hematoxylin.

Immunohistochemical Staining of Living and Acetone-Fixed Cells

For living cell staining, cells were detached, washed and diluted to $1\times10^6$ cells/ml. 1 ml of cell suspension was centrifuged at 1,500 g for 5 minutes. Antibody diluted to 40 μg/ml with complete RPMI was added to a final volume of 1 ml and incubated for 90 minutes on ice. Cells then were pelleted at 1,500 g for 5 minutes and resuspended with 500 μl RPMI. With 200 μl of the cell suspension, cytospin preparations were prepared and air-dried for 30 minutes. Cells were fixed in acetone for 30 minutes and washed with Tris/NaCl three times. HRP-coupled rabbit anti human IgM (DAKO) was diluted 1:50 in PBS/BSA (0.1%) and incubated for 30 minutes at RT. After three washings, staining was performed as mentioned above.

For staining of acetone-fixed cells, cytospins were prepared, air-dried at RT and fixed in acetone as described above. Cytospins then were blocked for 15 minutes with PBS/BSA (0.1%) and incubated for 30 minutes with 10 μg/ml primary antibodies followed by three washings. Incubation with secondary antibody and staining was performed as described above.

MTT-Proliferation Assay

The MTT-assay with the established cell line 23132 was performed as described, e.g., in Vollmers et al. (Cancer 74:1525-1532 (1994)). In short, trypsinized cells were diluted to $1\times10^6$ cells/ml in complete growth medium, and 50 μl of cell suspension was added to each well of a 96-well plate. 50 μl of the antibody, diluted to the indicated concentrations with complete growth medium, were added to the wells, and plates were incubated for one or two days at 37° C. in a humidified incubator. For analysis, 50 μl of MTT (3(4,5 dimethylthiazol)-2,5 diphenyltetrazolium bromide) solution (5 mg/ml) were added to each well, and plates were incubated for 30 minutes. After incubation, plates were centrifuged at 800 g for 5 minutes, MTT solution was removed, the stained cell pellet was dissolved in 150 μl dimethylsulphoxide, and absorption was measured at wavelengths of 540 nm and 690 nm.

Cell-Death ELISA

The extent of antibody-induced apoptosis on tumor cell line 23132/87 was analyzed by the Cell Death Detection ELISA$^{PLUS}$ Kit (Roche, Mannheim, Germany). For this assay $1\times10^4$ tumor cells were plated on 96-well plates and incubated in presence of fragmented PAM-1 antibody for 24 hours at 37° C. and 7% $CO_2$ in a humidified $CO_2$ incubator.

To demonstrate normal growth, the cells were supplemented with complete growth medium (control 1). Unrelated fragmented IgM served as a negative control (control 2). After incubation the cells were centrifuged for 10 minutes at 200 g, the supernatants were removed followed by an incubation with lysis-buffer for 30 minutes at RT. After centrifugation, the supernatants were transferred into a streptavidin-coated microtitre plate (MTP), immunoreagent added (mixture of 10% Anti-Histone-Biotin, 10% Anti-DNA-peroxidase (Anti-DNA POD) and 80% incubation buffer) and incubated for 2 hours at RT on a MTP shaker at 250 rpm. Following incubation, unbound components were removed by washing with incubation buffer. Peroxidase is determined photometrically with an ABTS™ as a substrate (1 ABTS™ (2,2'-Azino-di[3-ethyl-benz-thiazolin-sufonat) tablet in 5 ml substrate buffer). The antibody induced apoptosis was measured at 405 mn against ABTS solution as a blank (reference wavelength approx. 490 nm).

In Vivo Experiments

To determine the effects of fragmented PAM-1 on tumor cell growth in vivo, the nude mouse-human stomach carcinoma cell system was used (see, e.g., Vollmers et al., Oncology Reports 5:35-40 (1998)). Briefly, $2\times10^6$ stomach carcinoma cells (23132/87) were injected i.p. into 8 week old NMRI nu/nu mice (Harlan Winkelmann GmbH, Borchen, Germany) followed by injections of fragmented PAM-1 antibody (200 μg) at day 4 post carcinoma cell injection. Control mice were injected with unrelated fragmented human IgM in the same concentration. Visible tumor growth was measured macroscopically during the experiment. The experiments were terminated when tumors had reached maximal tolerable size, whereupon the mice were sacrificed, tumor size, respectively tumor weight, was determined, and organs and tissues inspected for the spread of tumors and other alterations.

FragEl-Klenow Apoptosis Assay

To investigate whether or not the tumors induced in mice were undergoing apoptosis, DNA-fragmentation was measured using immunohistochemistry. The Klenow-assay, which is specific for apoptosis, which is standard in the art and was performed as described in Vollmers et al. (Oncology Reports 5:549-552 (1998)). Briefly, mouse tumors grown in PAM-1 treated mice and in the control group were fixed in 3% formaldehyde and embedded in paraffin. Sections were then processed using the apoptosis-specific FragEL-Klenow DNA Fragmentation Kit (Calbiochem-Novabiochem, Bad Soden, Germany) according to the manufacturer's instructions.

Methods of Determining the Sequence of Novel Isoform of CFR-1

RNA was prepared for the cDNA synthesis with the aid of the RNEASY kit from Quiagen. For this RNA preparation, $1\times10^6$ cells were washed twice using ice cold PBS and pelletized at 1000×g for 5 minutes and the RNA was prepared in accordance with the manufacturer description. 5 μg RNA (1-5 μl solution) was mixed with 1 μl oligo-dT$_{15}$ (1 μg/μl) and 2 μl random primer (40 μM) and brought up to a total volume of 8 μl using $H_2O$. The RNA was denatured for 10 minutes at 65° C. and the sample was subsequently cooled on ice. 17 μl Mastermix, consisting of 5.2 μl DEPC-treated $H_2O$, 5 μl 5× reverse transcriptase buffer, 2.5 μl dNTPs (per 10 mM), 2.5 μl DTT (250 mM), 0.8 μl RNasin (400 U), and 1 μl M-MLV reverse transcriptase (200 U), was then added to the RNA. The synthesis of the cDNA was performed for 70 minutes at 37° C. and was subsequently terminated by heating to 95° C. for 5 minutes. 1-5 µl of the cDNA was mixed with the PCR Mastermix and brought up to 25 µl total volume using H₂O. The PCR Mastermix consisted of 2.5 µl 10× Taq-polymerase buffer, 0.5 µl 10 mM NTPs, 1.5-2 µl 25 mM MgCl₂, 0.5 µl each 20 pM 3' and 5' primer, and 0.2 µl Taq polymerase (1 U). The amplification conditions for the various PCR products are shown in the following overview of the PCR program used for amplifying the various cDNAs.

| Product | Annealing in [° C.] | MgCl₂ [mM] | Extension time [seconds] | Cycles | Product size [bp] |
|---|---|---|---|---|---|
| Fragment 1 | 55 | 1.75 | 45 | 40 | 691 |
| Fragment 2 | 60 | 1.5 | 45 | 40 | 898 |
| CFR Fragment 3 | 55 | 2.0 | 45 | 40 | 739 |
| Fragment 4 | 55 | 2.0 | 45 | 40 | 941 |
| Fragment 5 | 55 | 2.0 | 45 | 40 | 750 |

Primer Sequences

Sequences for the oligonucleotides used for the PCR are shown below

CFR

```
                                           (SEQ ID NO:11)
CFR-For 1
5' OGC AGC TTC AGC AGC AAC AGC A 3'

(SEQ ID NO:12)
CFR-Rev 1
5' CAG CTC AGC CAC CCG GAG AAT G 3'

(SEQ ID NO:13)
CFR-For 2
5' GCT TGG AGA AAG GCC TGG TGA A 3'

(SEQ ID NO:14)
CFR-Rev 2
5' TGG CAC TTG CGG TAC AGG ACA G 3'

(SEQ ID NO:15)
CFR-For 3
5' GAA CAC CGT CTC TTA GAG CTG C 3'

(SEQ ID NO:16)
CFR-Rev 3
5' GCT TCC TGC AGA GTG TCA TTG C 3'

(SEQ ID NO:17)
CFR-For 4
5' GGA GGA CGT GTT GAA GCT TTG C 3'

(SEQ ID NO:18)
CFR-Rev 4
5' CCA GGG CAC AAG CAG TAT GAA G 3'

(SEQ ID NO:19)
CFR-For 5
5' CAA CAG CAG ACA GGT CAG GTG G 3'

(SEQ ID NO:20)
CFR-Rev 5
5' CCG GAA GTT CTG TTG GTA TGA G 3'
```

Sequencing was performed using a sequencer from the firm Applied Biosystems. The following oligos were used for the sequencing of cloned PCR products:

```
T₃
5' ATT TAA CCC TCA CTA AAG GG 3'       (SEQ ID NO:21)

T₇
5' GTA ATA CGA CTC ACT ATA GGG C 3'     (SEQ ID NO:22)
```

3 µl plasmid DNA was mixed with 1 µl primer (3.2 pM), 11 µl H₂O, and 5 µl reaction mixture of the ABIPRISM Sequencing Kit and incubated in the thermocycler for 25 cycles using the following parameters:

| Denaturing | Annealing | Extension |
|---|---|---|
| 95° C., 30 seconds | 52° C., 15 seconds | 60° C., 4 minutes |

To remove oligonucleotides and dNTPs, the reaction mixture was purified via a Sephadex G-50 filled purification column. For this purpose, a 100 µl pipette tip was loaded up to the upper edge with column material and centrifuged for 3 minutes at 2000×g. Subsequently the sample was applied and the small column was centrifuged again. The DNA was then precipitated by 2 µl Na acetate (pH 5.2) and 50 µl 100% ethanol and pelletized by centrifuging at 13,000×g for 15 minutes. After drying, the DNA was received in 3 µl formamide/25 mM EDTA (5:1) and analyzed in the sequencer.

Sequence Analysis

At least five clones were sequenced from each cloning reaction. To identify potential errors which arose during the amplification using the Taq-polymerase and/or the sequencing, the sequences of the cloned PCR fragments were compared with one another with the aid of the DNAsis for Windows software and a consensus sequence of all clones was established from both read directions. By rewriting the DNA sequences into amino acid sequences, the number of silent mutations and amino acid substitution mutations were determined. The sequences for MG160 and CFR-1 were drawn from the NCBI databank and compared to sequence of the PCR products using the DNAsis for Windows program. An alignment of these sequences is shown in FIG. 16.

RNA-Isolation

RNA from normal and cancerous gastric tissue of the stomach was isolated using the phenol-guanidine-isothiocyanate method with TRIZOL® Reagent (Invitrogen). In brief, frozen normal and tumor tissues were cut in serial 5 µm sections on a freezing microtome. 1 ml TRIZOL® Reagent was added to the tissue samples and the solutions were homogenized subsequently. Following homogenization the insoluble material was removed from the homogenate by centrifugation at 12,000×g for 10 minutes at 4° C. 200 µchloroform was added to the RNA containing supernatant, and, after mixing the solution was incubated for 3 minutes at RT. After centrifugation for 15 minutes at 12,000×g and 4° C., the aqueous phase was precipitated in 500 µl isopropanol by mixing for 30 secods, incubation for 10 minutes at RT and centrifugation for 10 minutes at 12,000×g and 4° C. The resulting RNA pellet was washed with 1 ml of 75% ethanol and centrifuged for 5 minutes at 7,500×g at 4° C. The RNA pellet was air-dried and re-suspended in 80 µl DEPC-treated water. The integrity and quality of purified total RNA were controlled by 1% agarose gel electrophoresis and the concentrations were evaluated by spectrophotometry.

Semi-Quantitative Reverse Transcription-PCR mRNA levels were examined using semi-quantitative Reverse Transcription-PCR (RT-PCR) method. Synthesis of first-strand cDNA from normal and cancerous gastric tissue was performed with 5 µg of total RNA using Moloney murine leukemia virus reverse transcriptase (M-MLV RT, Invitrogen GmbH, Karlsruhe, Germany) and oligo-dT primer according to the supplier's manual. The PCR method was used to detect CFR-1 mRNA. PCR reactions were carried out in a 25 µl volume with 2 nM $MgCl_2$, 0,4 pM primer, 200 µm each dNTP and 1 unit of Taq polymerase (MBI). The expression of CFR-1 mRNA was normalized to GAPDH mRNA levels. The primers specific for CFR-1 and GAPDH were designed on their reported sequences and commercially synthesized by MWG-BIOTECH AG (Ebersberg, Germany). The sequences of these oligonucleotides are 5' CAAGAGCAGACAG-GTCAGGTGG 3' (SEQ ID NO:30) and 5' CCGGAAGTTCTGTTG-GTATGAG 3' (SEQ ID NO:23) for CFR-1 and 5' GTGGAAGGACTCAT-GACCACAGTC 3' (SEQ ID NO:24) and 5' CATGTGGGC-CATGAGGTCCACCAC 3' (SEQ ID NO:25) for GAPDH. Sizes of expected amplification products are 750 bp for CFR-1 and 482 bp for GAPDH. CFR-1 was amplified at 94° C. for 4 minutes and for 40 cycles at 94° C. (30 s), 55° C. (30 s) and 72° C. (30 s) with a final extension step at 72° C. (4 mm). As a negative control each PCR run included a sample containing PCR buffer but no cDNA. The PCR products were identified by agarose-gel-electrophoresis (2%) in Tris-acetate-EDTA buffer and ethidium bromide staining.

Pepsin Cleavage

For pepsin digestion of the PAM-1 antibody a buffer exchange with 100 mM sodium citrate (pH 3.5) using NAP™-10 columns (Amersham Pharmacia Biotech) was used. Additionally pepsin digestion was done with an unrelated human IgM antibody (Chrompure IgM, Dianova, Hamburg, Germany) to obtain a suitable negative control. For each milligram of antibody, 5 µg pepsin (Sigma Aldrich, Taufkirchen, Germany) was added, followed by incubation for 10-15 minutes in a 37° C. water bath. The reaction was stopped by adding 1/10 volume of 3.0 M Tris (pH 8.8) followed by centrifuging at 10,000 g for 30 minutes. Prior to use in experiments the fragmented PAM-1 antibody and the fragmented human control IgM were dialyzed against PBS. The success of pepsin cleavage was examined by SDS gel electrophoresis and Western blotting.

The following experiments were carried out using the above materials and methods.

EXAMPLE 2

Identification and Characterization of the Antigen Recognized by the PAM-1 Antibody Purification and Identification of Antigen 103/51

Figure 5:
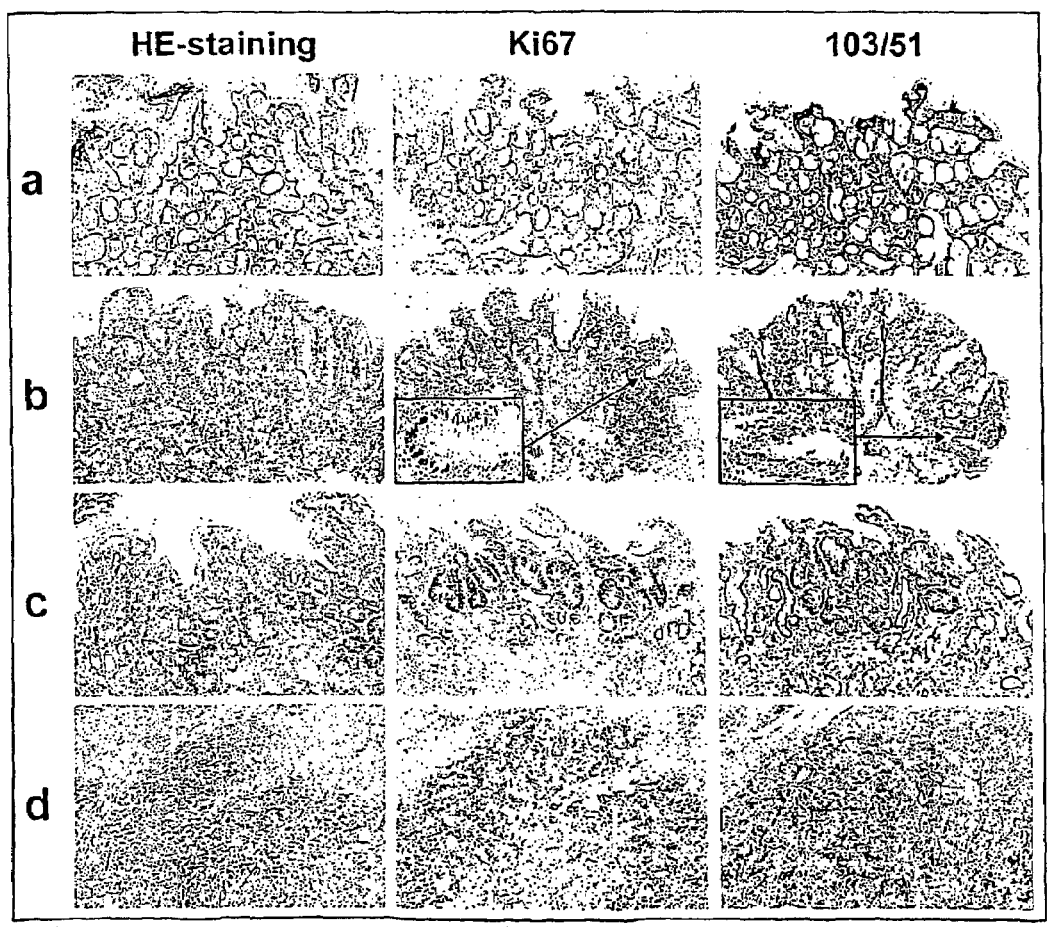
Figure 6:
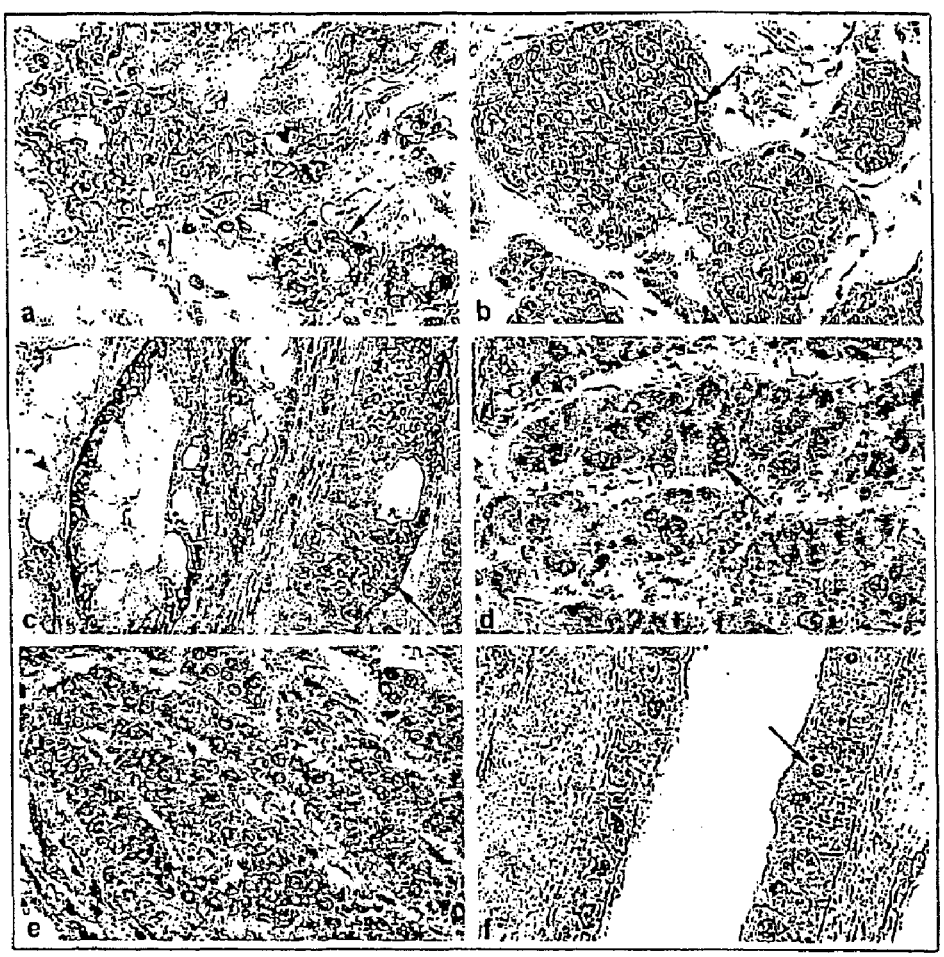
FIGS. 6A-6F are a series of images of immunohistochemical staining with antibody 103/51 on different cancerous and normal tissues. The staining of antibody 103/51 on the following tissues is shown: Carcinoma of the ampulla of Vater (FIG. 6A), mamma carcinoma 30 invasive lobular (FIG. 6B), adenocarcinoma of the colon and no staining of normal goblet-cell epithelium of the colon (FIG. 6C), hepatocellular carcinoma (FIG. 6D), glomerular and fascicular zones of the adrenal gland (FIG. 6E), collection tubes of the kidney-specific staining of the Golgi apparatus (arrow) (FIG. 6F). Arrows in FIGS. 6A-6D indicate tumor cells, the arrow in FIG. 6C points to goblet cells, the arrow in (FIG. 6F) indicates Golgi apparatus (Magnification 400× (FIGS. 6A-6E) and 200× (FIG. 6F)).

Western Blot analysis was used to show that the antibody 103/51 binds to an approximately 130 kD membrane protein on stomach cancer cells. We pre-purified this protein by sequential size exclusion and anion exchange chromatography (FIG. 1A). The protein was excised from a Coomassie-stained preparative SDS-PAGE, one part was used for production of mouse monoclonal antibodies (see below), and one part was used to identify the protein using the methods standard in the art, as outlined by Shevchenko et al. (Proc. Natl. Acad. Sci. U.S.A. 93:14440-14445 (1996)). After 3 hours of in-gel digestion with trypsin, about 1% of the total digested volume was removed and subjected to high mass accuracy MALDI peptide mass mapping (saving the rest of the digest for nanoelectrospray analysis, in case MALDI MS did not lead to definitive identification). Despite the femtomole amount of the protein digest consumed for MALDI analysis, a database search matched 35 peptides to the CFR-1 sequence with a mass accuracy within 50 ppm. These peptides cover 29% of the CFR-1 sequence, thus definitively identifying the protein as a CFR-1 homologue. CFR-1 has a calculated molecular weight of approximately 134 kD (Burrus et al., 1992, Mol. Cell Biol. 12:5600-5609) (FIG. 1B). The nucleic acid (SEQ ID NO:5) and amino acid (SEQ ID NO:6) sequence of this novel CFR-1 homologue are shown in FIGS. 10-1 to 10-5.

Effect of Transient Transfection of Cell Line 23132 with CFR-1 Antisense Vector on Binding of Antibody 103/51 and Live Cell Staining We investigated the effect of an antisense transfection of the stomach carcinoma cell line 23132 using immunohistochemistry and flow cytometry. For this, an 897 bp PCR-fragment of CFR-1, flanking the region between basepairs 802 and 1699, was cloned into the pHOOK-2 vector in an antisense direction in reference to the CMV promoter. The washed cells were transfected with the pHOOK-CFR antisense vector, pHOOK-lacZ, and pHOOK vector in an intermediate step. Transfection was controlled by a β-Galactosidase assay (data not shown). 48 hours after transfection, cytospin preparations were prepared and stained with antibodies 103/51 and anti-cytokeratin 18 as a control (data not shown).

Figure 2:
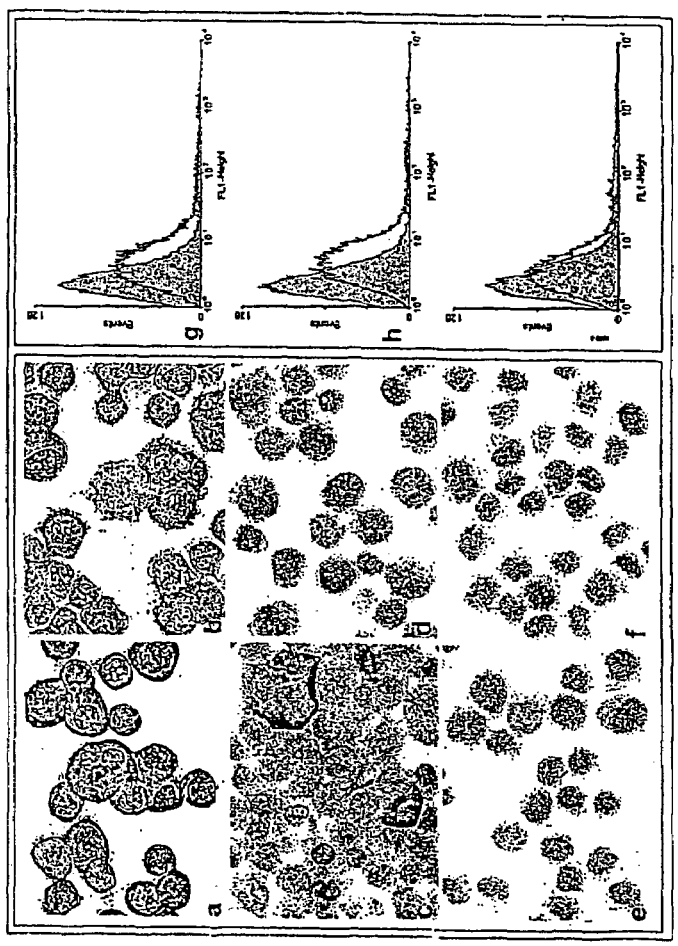
FIGS. 2A-2F are a series of images showing the effect of CFR-1 antisense transfection on antibody 103/51 staining and live cell staining (Magnification 200×).
FIG. 2G is a graph of flow cytometry results of cell line 23132 with antibodies Chromopure human IgM (grey) and 103/51.
FIG. 2H is a graph of the analysis of cells transfected with control vector pHOOK-2 with flow cytometry 48 hours after transfection.

The immunohistochemistry showed a clear reduction of staining in cells transfected with the pHOOK-CFR antisense vector when compared to mock-transfected cells (FIGS. 2A and 2B). This confirmed the binding of antibody 103/51 to CFR-1. The slight cytoplasmic staining visible in both stainings might be due to non-specific binding often observed in staining with human IgM antibodies on acetone-fixed cells. Membrane expression and the effect of transfection were also tested by flow cytometry (FIGS. 2G-2I). The data indicate a reduction in binding of antibody 103/51 after transfection of cells with the CFR-1 antisense vector. However, untreated cells or cells transfected with the control vector pHOOK-2 shows a clear binding to cell line 23132, indicating expression of a CFR-1 isoform on the cell membrane.

To investigate the specific membrane distribution of the CFR-1 isoform, we performed live cell staining with cell line 23132 and some non-stomach cancer cell lines. On the cell line 23132 we found a clear staining (FIGS. 2C and 2D), while the human lung adenocarcinoma cell lines Colo-699 (FIGS. 2E and 2F) and human epidermoid lung carcinoma cell line EPLC-272H (data not shown) were clearly negative. These data show that the described CFR-1 isoform is not expressed in all cancerous cell lines, and the exclusive membrane staining of 23132 cells indicates that the CFR-1 isoform has a distribution that is different from the one described so far for CFR-1.

Glycosidase Assay

CFR-1 is a sialoglycoprotein with 5 possible N-glycosylation sites and it has been shown by treatment with glycosidase F that the molecule is glycosylated at these sites (Steegmaier et al., Nature 373:615-620 (1995)). Since tumor-reactive antibodies often react with carbohydrate residues, we investigated whether this is the case for the antibody 103/51. Cytospin preparations of cell line 23132 were incubated for 4 hours with O- and N-glycosidases, and then subjected to immunohistochemical staining with antibody 103/51. Treatment of cells with N-glycosidase led to a dramatic decrease in 103/51 staining (FIG. 3B), while incubation with dephosphorylation buffer (FIG. 3A) or digestion with O-glycosidase (data not shown) had no effect on binding of the antibody 103/51. This shows that the specificity of binding of the antibody 103/51 must be located in N-linked sugar residues and not in the primary protein sequence.

Figure 3:
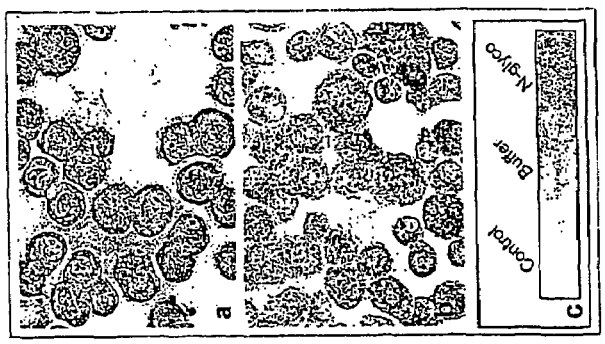
FIGS. 3A and 3B are images showing the effect of deglycosylation on staining with antibody 103/51.
FIG. 3C is a Western blot showing the effect of deglycosylation of membrane extracts of cell line 23132 on the reaction with antibody 103/51. Extracts which were incubated for 16 hours with deglycosylation buffer (Buffer) show no difference in staining in comparison with untreated extracts (Control). In contrast, incubation with N-glycosidase leads to a clear reduction in staining (N-glyco).
Figure 4:
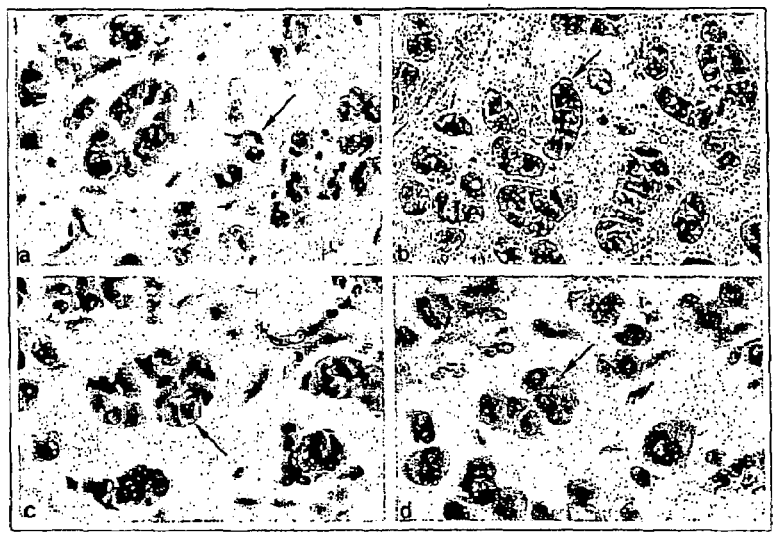
FIGS. 4A-4D are a series of images showing immuno-histochemical staining with murine antibody 58/47-69 and 103/51 on stomach adenocarcinoma cells. To show identical specificity of antibody 103/51 and murine antibody 58/47-69, diffuse-type stomach adenocarcinoma was stained with haematoxilin-eosin (FIG. 4A), antibodies 103/51 (FIG. 4B) and 58/47-69 (FIG. 4C), and anti-cytokeratin 18 as a positive control. Identical staining in FIG. 4C and FIG. 4D indicates identical specificity. (The arrows point to tumor cells.)

To further control for this effect, membrane extracts of cell line 23132 were deglycosylated for 16 hours and Western blots were prepared and stained with antibody 103/51. We found a reduction in the reaction on lysates incubated with N-glycosidase when compared to the control lysates (FIG. 3C).

Production of Murine Antibodies and Immunohistochemical Staining of Paraffin Section of Stomach Adenocarcinoma Commercial antibodies which specifically recognize CFR-1 are not available. Thus, we immunized mice with purified protein eluted from Coomassie-stained SDS-gel for production of monoclonal antibodies to strengthen the specificity, and to further characterize CFR-1 expression. Spleen cells were immortalized by fusion with the heteromyeloma NS0. 150 clones were tested for immunohistochemical staining. Positive clones were re-cloned, and the clone 58/47-49 (IgM) was used for further characterization. To investigate the binding properties of the human antibody 103/51 and the murine antibody 58/47-69, we stained paraffin sections of 15 different stomach adenocarcinoma and one adenoma. Identical staining of glandular cells of the normal epithelial tissue and intensive staining of carcinoma cells was found (FIGS. 4A-4D). In short, early carcinoma (n=2) were stained by both antibodies. On interstitial-type carcinoma both antibodies stained 4 out of 5 cases, on diffuse-type carcinoma all cases (n=4) were stained, and the intermediary-type were positive in 50% (n=4) with both antibodies. These results show a high expression of the CFR-1 isoform described herein in most cases of stomach carcinoma. The investigated adenoma showed a distinct staining pattern, with positive cells only in the transition from normal to transformed cells.

The nucleic acid sequence (SEQ ID NO:1) and the amino acid sequence (SEQ ID NO:2) of the variable region of the heavy chain of murine antibody 58-49/69 are shown in FIGS. 8A and 8B. As indicated in FIG. 8B, CDR1 of the 58-49/69 variable region heavy chain spans nucleotides 31-45 which encode amino acids 11-15, CDR2 spans nucleotides 88-138 which encode amino acids 30-46, and CDR3 spans nucleotides 235-264 which encode amino acids 79-88. In addition, the D-gene spans nucleotides 235-243 and the J-gene spans nucleotides 243-288.

The nucleic acid sequence (SEQ ID NO:3) and the amino acid sequence (SEQ ID NO:4) of the variable region of the light chain of murine antibody 58-49/69 are shown in FIGS. 9A and 9B. As indicated in FIG. 9B, CDR1 of the 58-49/69 variable region light chain spans nucleotides 49-96 which encode amino acids 17-32, CDR2 spans nucleotides 142-162 which encode amino acids 48-54, and CDR3 spans nucleotides 259-285 which encode amino acids 87-95.

The nucleic acid sequence (SEQ ID NO:28) and the amino acid sequence (SEQ ID NO:26) of the variable region of the heavy chain of human antibody 103/51 are shown in FIG. 17. CDR1 of the 103/51 variable region heavy chain spans nucleotides 31-54 which encode amino acids 11-18, CDR2 spans nucleotides 106-129 which encode amino acids 36-43, and CDR3 spans nucleotides 244-312 which encode amino acids 82-104.

The nucleic acid sequence (SEQ ID NO:29) and the amino acid sequence (SEQ ID NO:27) of the variable region of the light chain of human antibody 103/51 are shown in FIG. 18. CDR1 of the 103/51 variable region light chain spans nucleotides 82-96 which encode amino acids 28-32, CDR2 spans nucleotides 151-159 which encode amino acids 51-53, and CDR3 spans nucleotides 268-300 which encode amino acids 90-100.

Immunohistochemical Staining with Antibody 103/51 on Gastric Mucosa

To investigate the reaction pattern of antibody 103/51 on gastric mucosa in more detail, we performed immunohistochemical stainings on gastric tissue without inflammation, *H. pylori* associated chronic active gastritis, high-grade dysplasia, and gastric adenocarcinoma (FIGS. 5A-5D). On non-inflammed gastric tissue no reaction was seen. However, in the mucosa of a patient with *H. pylori* gastritis we found staining predominantly in the basal zone of foveolar cells. The staining pattern of antibody 103/51 shows a strong correlation with the activation pattern shown by Ki67 staining (Ramires et al., 1997, J. Pathol. 182:62-67). A more intensive staining of antibody 103/51 was seen in the proliferation zone of gastric dysplasia also correlating with Ki67 staining. The strongest staining was found in the proliferating zone of gastric adenocarcinoma.

Immunohistochemical Staining of Antibodies 103/51 and 58/47-69 on Different Tissues We investigated the expression of the CFR-1 isoform described herein in other cancerous and normal tissues by immunohistochemical staining of paraffin sections with antibodies 103/51 and 58/47-69. Out of 15 cancerous tissues (other than stomach carcinoma), antibody 103/51 showed staining in 13 cases (FIGS. 6A-6F, Table 1A). Negative staining was observed on anaplastic cells of the lung, confirming the results from the immunohistochemical staining and MTT-assay with the cell lines Colo-699 and EPLC-272H. These data indicate an over-expression of the CFR-1 isoform described herein and distribution to the cell membrane in malignant transformed cells.

TABLE 1A

Reaction pattern of antibody 103/51 with different tumor tissues.

| Tissue | Carcinoma-Type | Antibody-Staining |
| --- | --- | --- |
| Esophagus | Squamous | + |
| Stomach | Adeno (diffuse) | ++ |
| Stomach | Adeno (interstitial) | + |
| Colon | Adeno | + |
| Rectum | Adeno | + |
| Liver | Adeno (HCC) | ++ |
| Gallbladder | Adeno | + |
| Pancreas | Adeno (ductal) | + |
| Papilla of Vater | Adeno | + |
| Lung | Large cell anaplastic | − |
| Lung | Small cell | − |
| Lung | Adeno | ++ |
| Bronchus | Squamous epithelium | + |
| Mamma | Invasive (ductal) | + |
| Mamma | Invasive (lobular) | + |

TABLE 1B

Reaction pattern of antibody 103/51 with different normal tissues and pre-cancerous lesions.

| Tissue | Cell Type | Antibody-Staining |
|---|---|---|
| Salivary gland | Glandular | − |
| Stomach (not inflamed) | Glandular | − |
| Stomach (*H. pylori* infected) | Glandular | +[1] |
| Stomach (high grade dysplasia) | Glandular | ++[2] |
| Duodenum | Glandular | − |
| Colon | Epithelial | − |
| Rectum | Glandular | − |
| Pancreas | Glandular | − |
| Liver | Glandular | − |
| Gallbladder | Glandular | − |
| Oral mucosa | Squamous epithelium | − |
| Anal mucosa | Squamous epithelium | − |
| Skin | Keratinocyte, glandular | − |
| Mamma | Glandular | − |
| Larynx | Epithelial | − |
| Bronchus | Epithelial | − |
| Lung | Glandular, alveolar | − |
| Thyroid gland | Glandular | − |
| Adenohypophysis | Glandular | − |
| Adrenal gland | Glandular | ++[2] |
| Testis | Glandular | − |
| Ovary | Glandular | − |
| Prostate | Glandular | − |
| Urothelium | Epithelial | − |
| Kidney | Epithelial | ++[3] |
| Thymus | Lymphatic | − |
| Spleen | Lymphatic | − |
| Lymph node | Lymphatic | − |
| Cerebral cortex | Neural | − |
| Peripheric neural ganglia | Neural | − |

For Tables 1A and 1B, antibody staining was scored as follows: "−"=no staining; "+"=moderate staining; "++"=intense staining. HCC=hepatocellular carcinoma, [1] Proliferation zone, Glandular foveola, [2] Glomerular, fascicular zone (membranous staining), [3] Collection tubes of the endoplasmic reticulum.

On 28 normal and pre-cancerous tissues tested, we found a restricted expression only on three interstitial organs (Table 1B). Membrane staining was observed on the glandular foveola of the stomach and the glomerular and fascicular zones of the adrenal gland, while staining of the Golgi apparatus was found in the collection tubes of the kidney (FIG. 5). The Golgi specific staining further confirms the characterization of the antigen as homologous to CFR-1 that has been described earlier by Burrus et al. (Mol. Cell Biol. 12:5600-5609 (1992)).

Stimulation with Human and Murine Monoclonal Antibodies

Figure 7:
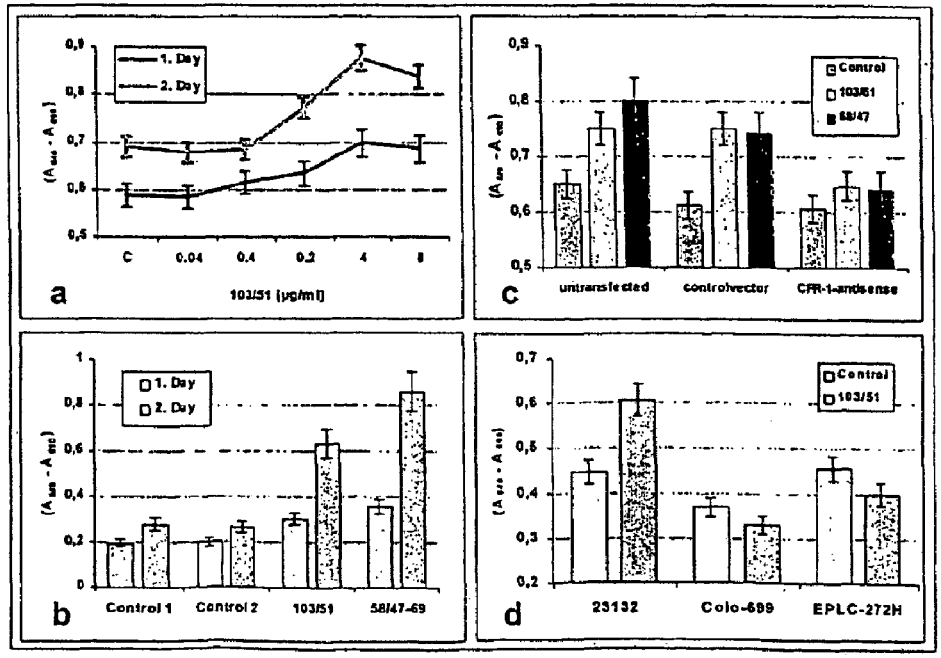
FIGS. 7A-7D are a series of graphs showing stimulation of cell lines with antibodies 103/51 and 58/47-69 as determined by colorimetric MTT-assays.

Antibody 103/51 leads to the stimulation of cell line 23132 in vitro. We measured this stimulation of antibody 103/51 using the mitochondrial hydroxylase assay (MTT), which is a standard assay for proliferation (Carmichael et al., Cancer Res. 47:936-942 (1987)). To further investigate the stimulating properties of antibody 103/51, we incubated the cell line 23132 with various concentrations of purified antibody. We found a concentration-dependent stimulation with the highest activity at 4 μg/ml (FIG. 7A). Higher concentrations showed a slight decrease in stimulation.

To test if the murine antibody 58/47-69 has the same effects on cell growth, we performed the MTT-stimulation assay with purified antibodies in comparable amounts. As it can be seen in FIG. 7B, both antibodies lead to the stimulation of cell line 23132 in vitro. This further confirms identical specificity of both antibodies.

To confirm that the stimulation of antibody 103/51 and the murine antibody 58/47-69 is mediated by binding to the CFR-1 isoform described herein, we transfected cells with control vector pHOOK-2 and CFR-1 antisense vector and tested transfected cells in the MTT-assay. As a positive control for transfection, cells were also transfected with pHOOK-2-lacZ vector followed by β-galactosidase staining (data not shown). Given that comparable stimulation was observed in non-transfected cells and cells transfected with control vector pHOOK-2, a reduction of the stimulating effect of both antibodies by the transfection procedure can be excluded. In contrast, cells transfected with CFR-1 antisense vector clearly show a reduced stimulation (FIG. 7C).

Finally, to demostrate that the stimulation by antibody 103/51 is not mediated by receptors other than the CFR-1 isoform described herein, we performed a MTT-stimulation assay with cell line the 23132 and compared it with lung carcinoma cell lines Colo-699 and EPLC-272H that do not express this isoform. While the cell line 23132 is stimulated as described above, the two lung carcinoma cell lines do not show any stimulation by antibody 103/51 (FIG. 7D), confirming the results observed in the immunohistochemistry.

EXAMPLE 3

The Antigen Recognized by the PAM-1 Antibody is Specifically Expressed on Cancerous and Pre-Cancerous Cells To further study and illustrate the highly specific expression of CFR-1 isoform recognized by the PAM-1 antibody on malignant tissue, 5 to 13 different cases of the most frequently occurring carcinomas were tested immunohistochemically. The reactivity of PAM-1 was compared with the expression of the Ki67 protein, which is localized in the nucleus of all proliferating cells. The function of this protein remains unknown (Endl and Gerdes, Exp. Cell Res. 257: 231-237 (2000)), but it is the most widely used standard marker for proliferation studies (Scholzen and Gerdes, J. Cell. Physiol. 182:311-322 (2000); and Brown and Gatter, Histopathology 40:2-11 (2002)). The staining results are summarized in Table 2.

TABLE 2

Expression of the isoform of CFR-1 recognized by PAM-1 on tumor tissues.

| Tissue | Carcinoma type | Sex m | Sex f | Age | Ki67 staining +/− | PAM-1 staining +/− |
|---|---|---|---|---|---|---|
| Esophagus | Squamous cell | 4 | 1 | 50-70 | 4/1 | 5/0 |
| | Adeno (Barrett) | 12 | 1 | 48-85 | 11/2 | 11/2 |
| Stomach | Adeno (diffuse) | 3 | 2 | 50-80 | 2/3 | 5/0 |
| | Adeno (intestinal) | 2 | 3 | 68-89 | 3/2 | 4/1 |
| | Adeno (Cardia) | 7 | 1 | 50-74 | 2/6 | 8/0 |
| Colon | Adeno | 8 | 5 | 38-88 | 10/3 | 13/0 |
| Liver | Adeno (HCC) | 8 | 1 | 43-76 | 0/9 | 9/0 |
| Pancreas | Adeno (ductal) | 5 | 3 | 41-75 | 2/6 | 8/0 |
| Lung | Adeno | 8 | 3 | 42-78 | 2/9 | 8/3 |
| | Squamous cell | 8 | 1 | 42-82 | 5/4 | 8/1 |
| Mamma | Invasive (ductal) | 0 | 5 | 37-88 | 4/1 | 5/0 |
| | Invasive (lobular) | 0 | 5 | 40-89 | 1/4 | 5/0 |
| Ovary | Adeno | 0 | 8 | 37-80 | 8/0 | 7/1 |
| Uterus | Adeno | 0 | 9 | 50-80 | 6/3 | 8/1 |

TABLE 2-continued

Expression of the isoform of CFR-1 recognized by PAM-1 on tumor tissues.

| Tissue | Carcinoma type | Sex m | f | Age | Ki67 staining +/− | PAM-1 staining +/− |
|---|---|---|---|---|---|---|
| Cervix | Squamous cell | 0 | 10 | 46-70 | 3/7 | 9/1 |
|  | Adeno | 0 | 9 | 33-65 | 8/1 | 9/0 |
| Prostate | Adeno | 9 | 0 | 49-70 | 1/8 | 9/0 |

Taken together, while PAM-1 shows a broad, intensive, and homogeneous staining on all carcinomas, Ki67 is not found in all carcinomas, it shows only a weak expression in most cases, and in contrast to PAM-1, it is non-homogeneously distributed (Table 2). Adenocarcinomas of the liver (HCC) are all negative and only several cases of adenocarcinomas of prostate, lung and invasive lobular carcinomas of the breast are positive for Ki67. These data also strongly confirm that the CFR-1 isoform recognized by PAM-1 is specifically expressed on most tested carcinomas.

Gene Expression of CFR-1 in Normal and Tumor Tissue

PAM-1 antibody reacts with a N-linked carbohydrate residue on the isoform of CFR-1 described herein which is specifically found on malignant cells. The lack of PAM-1 binding to non-malignant cells can therefore be either the result of a non-expression of the receptor on normal cells or of a post-transcriptional modification of CFR-1, which is different to that found on malignant cells. We investigated this on molecular level. CFR-1 MRNA of non-malignant and cancerous gastric tissue was examined using semi-quantitative RT-PCR. The RT-PCR method was standardized by using the constitutively expressed "housekeeping gene" GAPDH as an internal control. An increased expression level of CFR-1 could be detected in gastric tumor tissue compared with normal gastric tissue. This shows that CFR-1 detected by antibody PAM-1 on malignant cells is a specific over-expressed and most likely post-transcriptionally modified isoform of CFR-1.

Expression of the CFR-1 Isoform Recognized by the PAM-1 Antibody on Pre-Malignant Tissue The CFR-1 isoform recognized by the PAM-1 antibody is expressed in stomach cancer precursor lesions like *H. pylori*-induced gastritis and gastric dysplasia and the level of expression likely increases with the escalation of malignancy. To manifest and improve this observation and to obtain a comparison with the proliferation marker Ki67, additional immunohistochemical experiments were performed with a variety of other precursor lesions. The illustrations of precursor lesions from colon, esophagus, cervix, and bronchial carcinoma and corresponding proliferation zones described below demonstrate the specific expression of the PAM-1 antigen. The data are summarized in Table 3.

TABLE 3

Expression of the isoform of CFR-1 recognized by the PAM-1 antibody on pre-cancerous tissues (nd = not determined).

| Tissue | Precursor lesions | Sex m | f | Age | Ki67 staining +/− | PAM-1 staining +/− |
|---|---|---|---|---|---|---|
| Esophagus | Barrett metaplasia | 9 | 0 | 42-69 | 8/1 | 9/0 |
|  | Barrett dysplasia | 4 | 2 | 62-86 | 3/3 | 6/0 |

TABLE 3-continued

Expression of the isoform of CFR-1 recognized by the PAM-1 antibody on pre-cancerous tissues (nd = not determined).

| Tissue | Precursor lesions | Sex m | f | Age | Ki67 staining +/− | PAM-1 staining +/− |
|---|---|---|---|---|---|---|
| Stomach | *H. pylori* gastritis | 5 | 5 | 24-86 | 7/3 | 9/1 |
|  | Atrophic gastritis | 1 | 2 | 53-79 | 0/3 | 3/0 |
|  | Intestinal metaplasia | 5 | 2 | 49-86 | 7/0 | 7/0 |
|  | Tubular adenoma | 5 | 4 | 42-87 | 6/3 | 8/1 |
|  | Tubulovillous adenoma | 2 | 2 | 54-84 | 3/1 | 3/1 |
|  | High grade dysplasia | 3 | 0 | 65-74 | 3/0 | 3/0 |
| Colon | Dysplasia (ulcerative colitis) | 4 | 1 | 42-57 | 4/1 | 5/0 |
|  | Tubular adenoma | 5 | 2 | 54-85 | 5/2 | 6/1 |
|  | Villous adenoma | 8 | 2 | 45-85 | 9/1 | 8/2 |
| Cervix | CIN I | 0 | 8 | 22-52 | 7/1 | 8/0 |
|  | CIN II | 0 | 5 | 30-62 | 4/1 | 5/0 |
|  | CIN III | 0 | 5 | 29-41 | 5/0 | 5/0 |
| Bronchus | Squamous metaplasia | 5 | 0 | 61-72 | 3/2 | 5/0 |
|  | Epithelial dysplasia | 3 | 0 | 64-75 | 3/0 | 3/0 |
| Breast | D-CIS | 1 | 7 | 48-78 | nd | 8/0 |
|  | L-CIS | 0 | 3 | 49-50 | nd | 3/0 |
| Prostate | PIN | 15 | 0 | 55-76 | nd | 14/1 |

Adenoma-Carcinoma Sequence

Malignant changes and the resulting carcinomas of the colon belong to the frequently occurring neoplasia and are often associated with high mortality. The formation of colon carcinomas is a multi-step process which could be retraced to the so-called adenoma-carcinoma sequence. All adenomatous lesions arise as a result of epithelial proliferative changes and there is strong evidence that adenomas are a precursor lesion for invasive colorectal adenocarcinoma (Cummings, Semin. Gastrointest. Dis. 11:229-237 (2000); Scheiden et al., Int. J. Colorectal Dis. 15:29-34 (2000); and Wehrmann and Fruhmorgen, MMW Fortschr. Med. 142:26-29 (2000)). As such, colorectal carcinogenesis provides the ideal opportunity to investigate the reactive pattern of the PAM-1 antibody in precancerous lesions in more detail. Additional immunohistochemical stainings were therefore performed on different types of mucosa and epithelia. As noted above, PAM-1 antibody reacts with *H. pylori*-associated chronic active gastritis, high-grade dysplasia and gastric adenocarcinoma. We also determined that the PAM-1 antibody stains atrophic gastritis and intestinal metaplasia, which are pre-cancerous stages in the gastric carcinogenesis. Non-inflamed colon mucosa showed no reaction. Increased expression of the isoform of CFR-1 recognized by the PAM-1 antibody was found in adenomas of the colon, which have a higher risk of degenerating into adenocarcinomas. Expression of the isoform of CFR-1 recognized by the PAM-1 antibody was seen both in tubular and in villous adenomas, particularly in the proliferation zone.

Ulcerative colitis-related dysplasia, which consists of atypical changes in epithelial cells, is also recognized to be involved in the development of colorectal adenocarcinoma (Wong et al., Histopathology 37:108-114 (2000)). On this high grade dysplasia, clear staining by the PAM-1 antibody, especially of these atypical epithelial cells, was observed.

The most intense staining was found in colorectal adenocarcinoma, following the obtained results in case of gastric mucosa. Here, the expression of the isoform of CFR-1 recognized by the PAM-1 antibody correlates with the pattern of Ki67.

Barrett Carcinogenesis

Barrett esophagus is a complication of long-standing gastroesophageal reflux. The distal squamous mucosa is replaced by metaplastic columnar epithelium, as a response to prolonged injury. The carcinogenesis of esophagial adenocarcinoma takes place from Barrett metaplasia to Barrett dysplasia (Spechler, Semin. Gastrointest. Dis. 7:51-60 (1996); Haggitt, Hum. Pathol. 25:982-933 (1994); Devesa et al., Cancer 83:2049-2053 (1998); and Spechler, Am. J. Med. 111 Suppl 8A:130-136 (2001)).

Due to the increasing incidence of Barrett carcinoma, the expression of CFR-1 on Barrett epithelium was investigated using immunohistochemical staining with the PAM-1 antibody. Staining with PAM-1 revealed an increased expression of the isoform of CFR-1 recognized by the PAM-1 antibody in the metaplastic columnar epithelium of Barrett metaplasia. In addition, an intense staining pattern was observed in Barrett dysplasia, especially those cells with architectural and cytological abnormalities. The latter are regarded as precursors of the invasive adenocarcinomas of the esophagus (Barrett carcinoma) (Spechler, Am. J. Med. 11 Suppl 8A: 130-136 (2001)), and correlated with expression of Ki67. The strongest staining was found in Barrett carcinoma. Although the PAM-1 antibody showed an intense staining pattern for carcinoma of the cardia (heart), Ki67 was not expressed in a comparable manner.

Cervical Neoplasia

Increased expression of the isoform of CFR-1 recognized by the PAM-1 antibody on cervical epithelium with architectural abnormalities was also observed. The precursors of the cervical squamous cell carcinoma are classified as cervical intraepithelial neoplasia grade I, II and III. Mild dysplasiae are termed CIN I up to carcinoma in situ lesions CIN III (Arends et al., J. Clin. Pathol. 51:96-103 (1998)). The precursor lesions (CIN I-III) and invasive malignancy of the cervix, the squamous cell carcinoma were included in this study.

Normal epithelium showed no reaction with the PAM-1 antibody, whereas increased staining with the PAM-1 antibody was noted for the different types of cervical neoplasia. The staining pattern followed the appearance of atypical cells in the different cell layers and the widening of the basal proliferation zone. The reaction of Ki67 generally correlated with the staining pattern of the PAM-1 antibody, but the staining was less intense.

Bronchial Carcinogenesis

Carcinomas of the lung are one of the most frequently occurring carcinomas world-wide. The most common type is the squamous cell carcinoma, which correlates closely with a history of smoking. In the airways of smokers, squamous metaplasia and dysplasia are usually present. In squamous metaplasia the normal bronchial ciliated epithelium is replaced by squamous epithelium. With occurrence of cytological disturbance and severe atypia, the lesion becomes known as squamous dysplasia (Colby et al., Adv. Anat. Pathol. 5:205-212 (1998); and Franklin, J. Thorac. Imaging 15:3-12 (2000)).

Normal ciliated epithelium shows no expression of the isoform of CFR-1 recognized by the PAM-1 antibody, while the PAM-1 antibody reacted with metaplasia and dysplasia of bronchus epithelium. Squamous cell metaplasia of the bronchus represents the initial stages of carcinogenesis and shows a lower intensity of staining compared to dysplasia. For dysplasia, the preliminary stage of cancer, a more intensive staining was observed. The most intense staining was again observed in the squamous cell carcinoma. In each of the three cases in this study, the staining of PAM-1 correlated with the reaction pattern of Ki67.

Proliferation Zones

To investigate whether expression of the isoform of CFR-1 recognized by the PAM-1 antibody is specific for malignant proliferation and not involved in normal proliferation processes (e.g., regeneration of tissue), we stained different proliferative regions of healthy and pre-malignant tissue with PAM-1 and Ki67 antibodies. We observed that the proliferation zone of normal colon mucosa is positive for Ki67, but negative for expression of the isoform of CFR-1 recognized by the PAM-1 antibody. The same result was seen with normal cervical tissue. Here again Ki67 shows a positive staining of the proliferation zone while the isoform of CFR-1 recognized by the PAM-1 antibody is not expressed. In contrast, non-dysplastic intestinal-type Barrett metaplasia, which defines Barrett's esophagus the pre-malignant lesion for adenocarcinoma of the esophagus, shows a positive expression of Ki67 and the isoform of CFR-1 recognized by the PAM-1 antibody. This clearly shows that the isoform of CFR-1 recognized by the PAM-1 antibody is not expressed in healthy proliferating cells.

Summary of the Expression of the Isoform of CFR-1 Recognized by the PAM-1 Antibody on Pre-Malignant Lesions The immunhistochemical data on precancerous lesions are summarized in Table 3 (above). 3 to 15 different cases of each available precursor lesion type were tested. In general, antibody PAM-1 shows a clear positive and homogeneous staining on nearly all different precursors and in addition an increasing level of expression with the grade of malignancy. In contrast, the proliferation marker Ki67 shows a similar non-homogeneous expression on carcinomas (see, for example, atrophic gastritis, tubular adenoma of stomach, and squamous metaplasia of bronchus) and is expressed on both healthy and malignant tissue. In addition, proliferation zones of healthy tissue are clearly positive for Ki67, but negative for the isoform of CFR-1 recognized by the PAM-1 antibody, supporting the association of this isoform of CFR-1 with malignancy.

EXAMPLE 4

Fragmented PAM-1 Antibody Induces Apoptosis

Apoptosis is the programmed cell death, suicide of cells, through fragmentation of the DNA, cell shrinkage, and dilatation of the endoplasmic reticulum, followed by cell fragmentation and the formation of membrane-bound vesicles, or apoptotic bodies. Apoptosis, the physiological form of cell death, guarantees rapid and clean removal of unnecessary cells, without triggering inflammation processes or tissue trauma, as in the case of necrosis. Under pathological conditions, it is also used for removing malignant cells, such as cancer precursor cells. It may be triggered through greatly varying stimuli, such as through cytotoxic T-lymphocytes or cytokines, such as tumor necrosis factor, glucocorticoids, and antibodies. It is the most frequent cause of death of eukaryotic cells and occurs in embryogenesis, metamorphosis, and tissue atrophy. Apoptotic receptors on the cell surface, such as those of the NGF/TNF family, are predominantly expressed on lymphocytes, but are also found on various other cell types, wherefore they are not suitable for cancer therapy. In particular, ligands and antibodies for these receptors have led to liver damage in in vivo tests. Therefore, tumor-specific receptors having apoptotic function are especially important.

PAM-1 Cleavage

Figure 11:
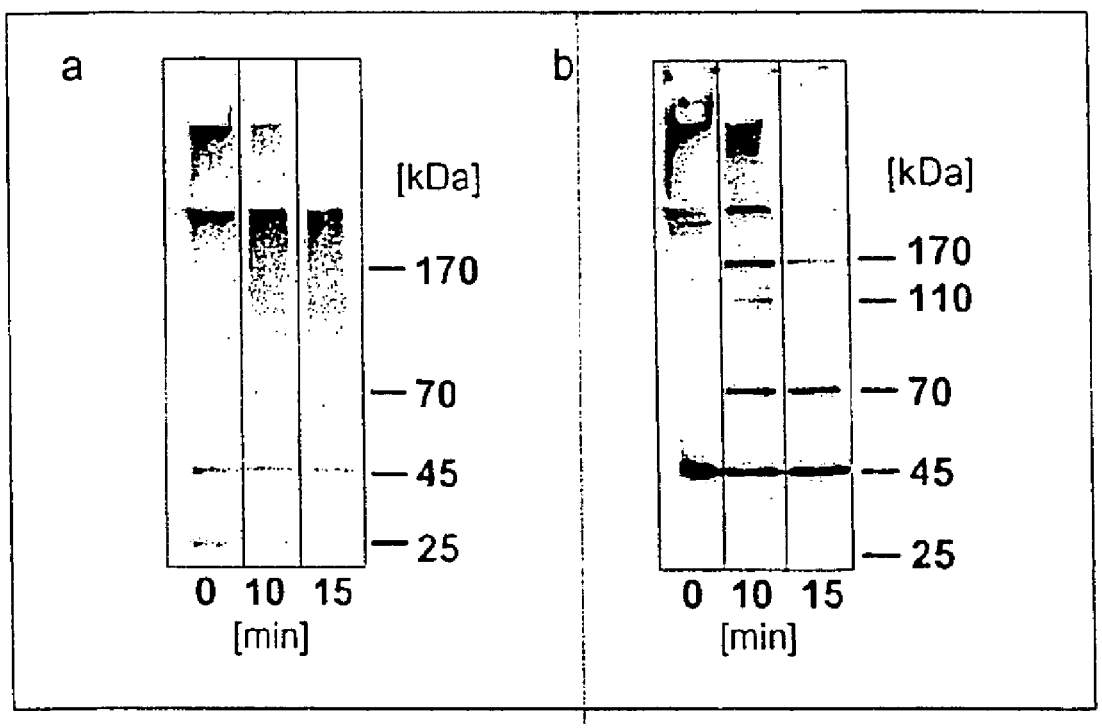
FIGS. 11A and 11B are a series of Coomassie blue stained SDS gels and Western blots showing fragments of antibody PAM-1. Intact PAM-1 antibody was digested with pepsin to yield antibody fragments. PAM-1 antibody was digested with Pepsin to yield antibody fragments.

Pepsin digestion was used to cleave the intact pentameric PAM-1 antibody into IgM antibody fragments. Following cleavage the resulting fragments were analyzed by SDS-PAGE and Western blotting under non-reducing conditions. After blotting, the intact antibody showed the characteristic bands corresponding to intact antibody, monomeric forms and light chains. By SDS-PAGE, the intact pentameric IgM of about 900 kDa was unable to migrate into the stacking gel. Following 10-15 minutes of treatment with pepsin the pentameric form was completely digested into monomeric, $F(ab)_2$, Fab, and light chain fragments which could be clearly identified by molecular weight (FIGS. 11A and 11B). No pentameric form of PAM-1 was left after digestion. The same experiment was done with an unrelated human IgM antibody leading to similar results (data not shown). The unrelated fragmented human IgM was used as a negative control in all following experiments.

Figure 12:
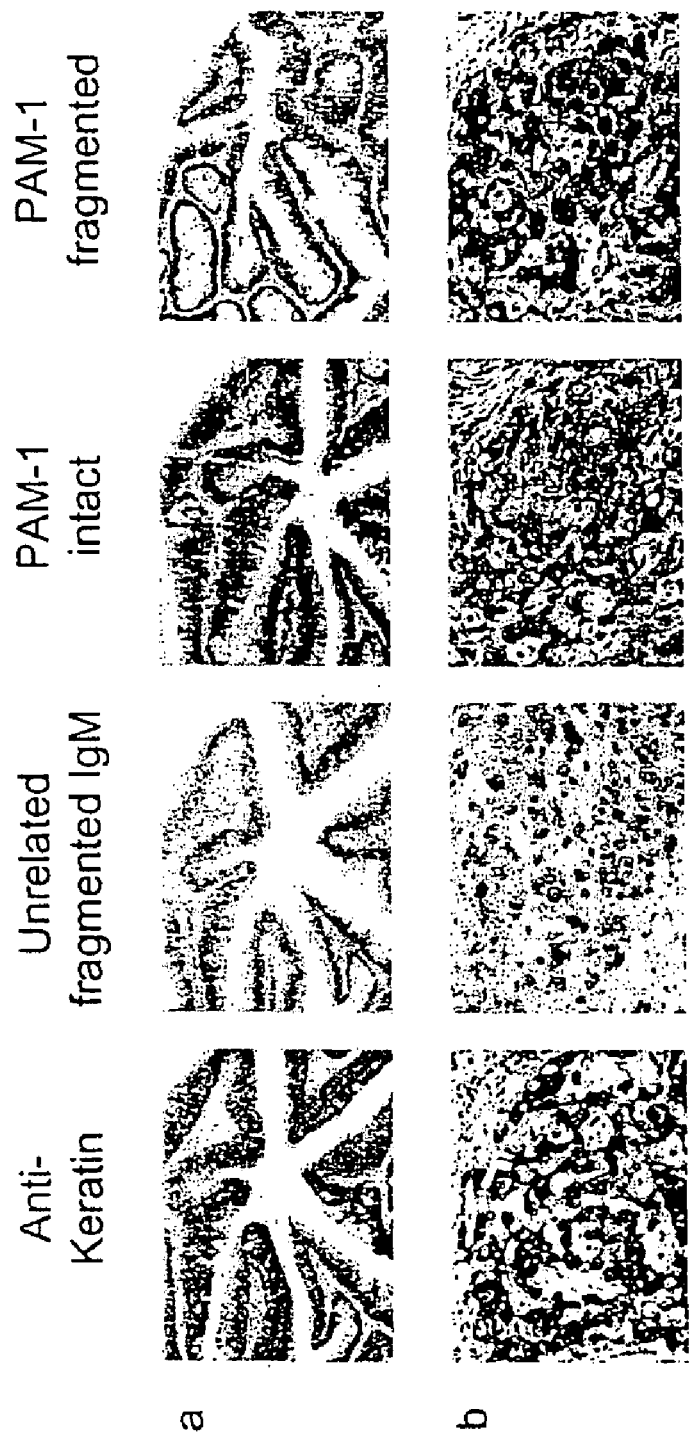
FIG. 12 B shows gastric adenocarcinoma. The original magnification was 100×.

The fragmented PAM-1 antibody was tested for tumor-binding on paraffin sections of human stomach carcinomas and precursors and compared to the intact PAM-1. Both antibody forms possess similar binding patterns on tumor and precursor cells as illustrated in FIGS. 12A and 12B.

PAM-1 In Vitro Activity

Figure 13:
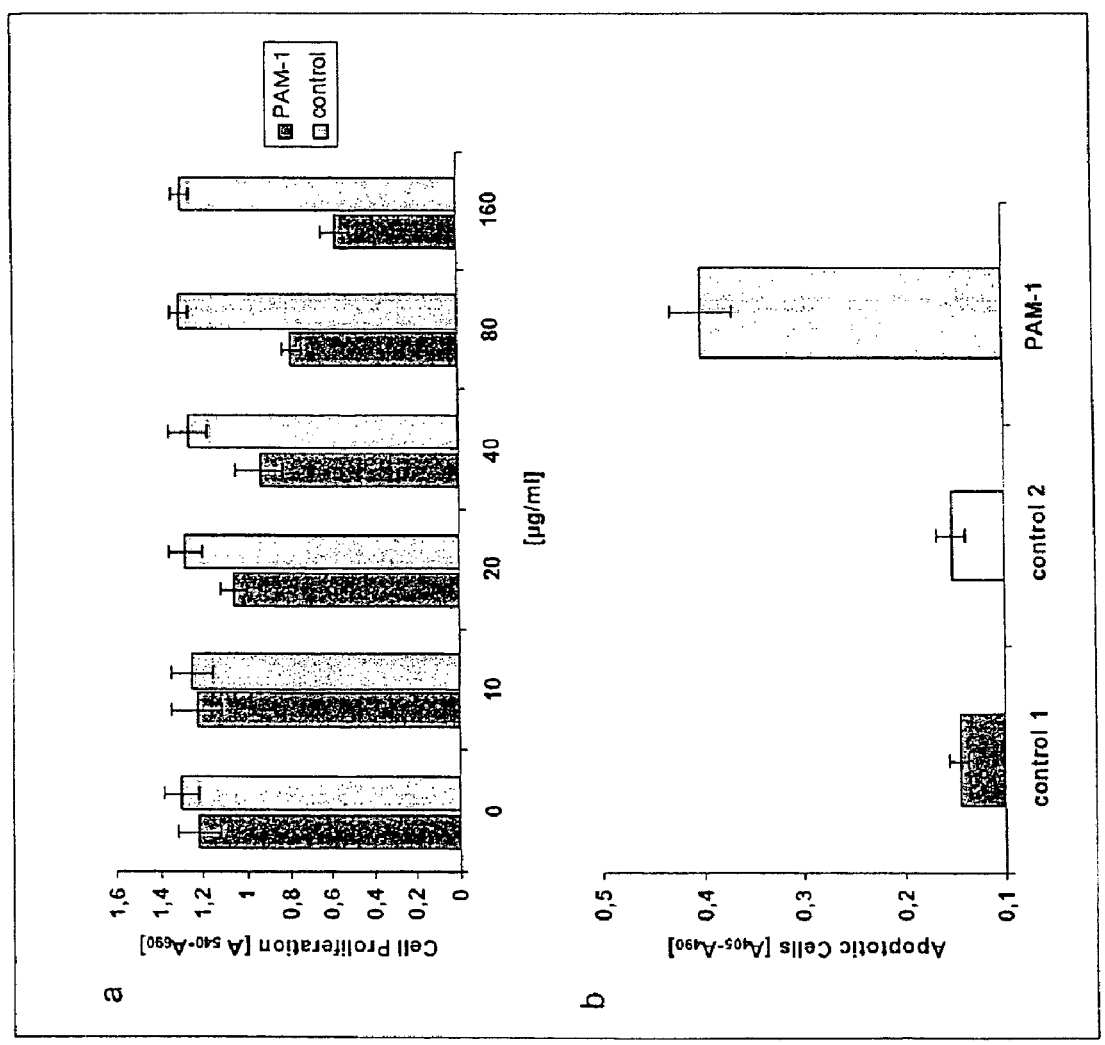
FIGS. 13A and 13B are graphs showing functional analyses of fragmented PAM-1 antibody in vitro. The consequences of fragmented PAM-1 antibody treatment on the proliferation of stomach cancer cell line 23132/87 was measured by MTT proliferation assay (FIG. 13A) and Cell Death Detection ELISA$^{PLUS}$ apoptosis assay (FIG. 13B).

To define the in vitro activity of the fragmented PAM-1 we used the colorimetric mitochondrial hydroxylase assay (MTT). We incubated cell line 23132/87 with various concentrations of the fragmented PAM-1 and found that the fragmented PAM-1 antibody inhibited cell proliferation in a concentration dependent manner (FIG. 13A). In contrast the cell growth of cells treated with different concentrations of unrelated fragmented IgM is not affected.

To further investigate the inhibitory effect of fragmented PAM-1 antibody on tumor cell growth, the apoptosis-specific Cell Death Detection ELISA$^{PLUS}$ Kit was used. The experiment illustrated in FIG. 13B clearly showed that fragmented PAM-1 antibody inhibits cell growth by inducing apoptosis in stomach carcinoma cells in vitro.

PAM-1 In Vivo Activity

Figure 14:
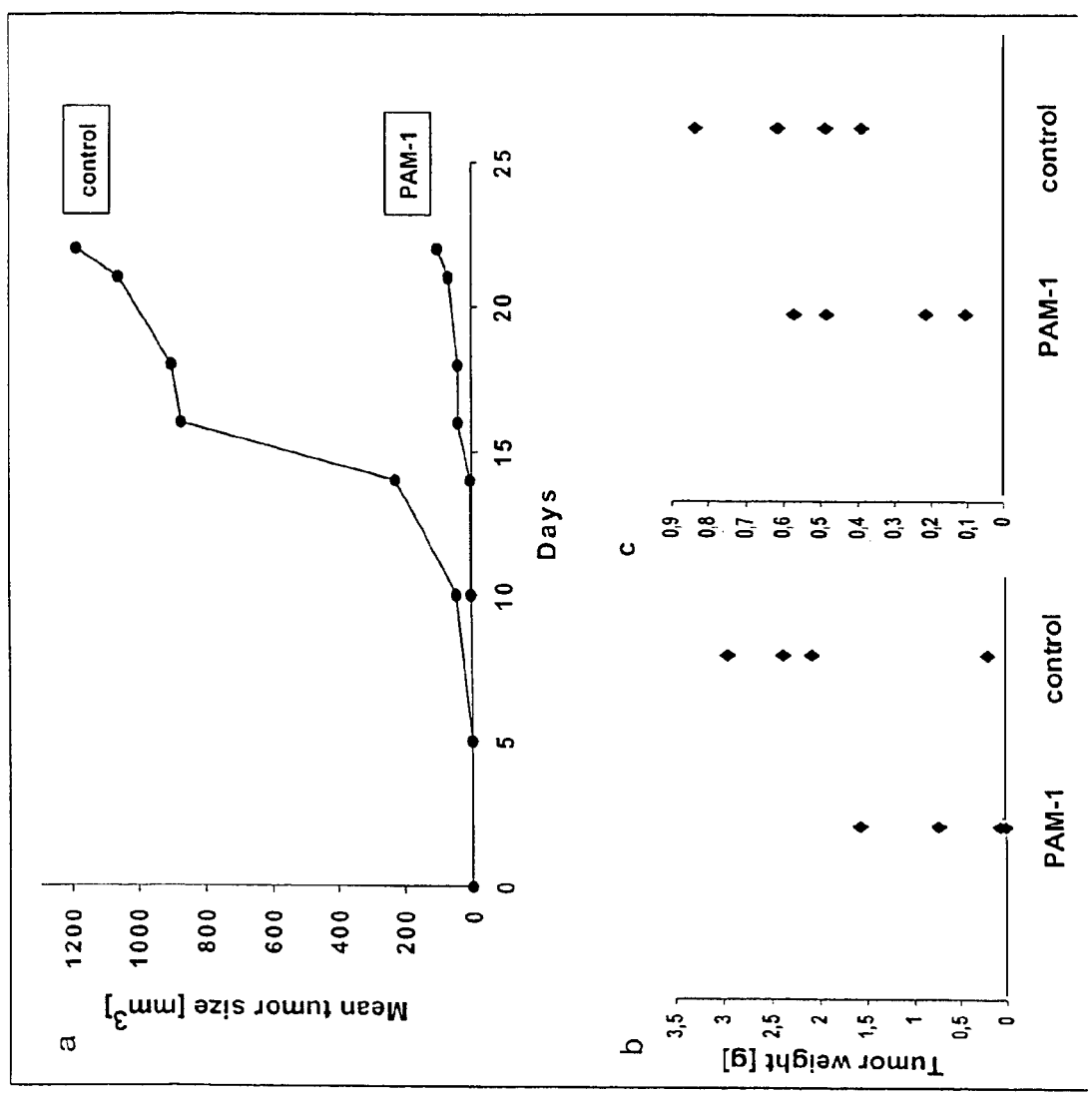
FIGS. 14A-14C are a series of graphs showing the results of in vivo experiments with human carcinoma cells treated with fragmented PAM-1 antibody in NMRI nu/nu mice.

To determine the effects of fragmented PAM-1 on tumor cell growth in vivo, a nude mouse-human stomach carcinoma cell system was used. A concentration of $2 \times 10^6$ cells derived from the human stomach carcinoma cell line 23132 were injected intraperitoneal (i.p.) into NMRI nu/nu mice. Four days after the inoculation of tumor cells, 200 µg of fragmented PAM-1 antibody, diluted in PBS, was injected i.p. Control mice received the same quantity of unrelated fragmented human IgM. Throughout the duration of the study, tumor growth was controlled macroscopically. After 23 days the mice were sacrificed. The control mice developed measurable tumors i.p. from day 5 onwards. A steep increase in tumor size was observed until day 23. In comparison mice treated with fragmented PAM-1 antibody did not develop detectable tumors before day 10. Moreover, the tumors which developed during the course of the experiment showed a significant reduction in growth and size. (FIG. 14A).

The study was also extended to include an inspection of organs and tissues of the mice for hidden spread of tumors and other alterations. In two additional experiments mice were inoculated i.p. with gastric cancer received fragmented PAM-1 or control antibody. After 23 days mice were inspected for tumor-growth. The control group showed expanded tumor spreading into the peritoneum, diaphragm, kidney, stomach, intestine, liver and spleen (the spleen was enlarged in all cases). In contrast, mice treated with fragmented PAM-1 antibody showed a reduced spread of tumors and in addition there were no enlarged spleens observable. In both experiments the overall weight of tumor mass was significantly reduced by the PAM-1 antibody (FIGS. 14B and 14C).

Figure 15:
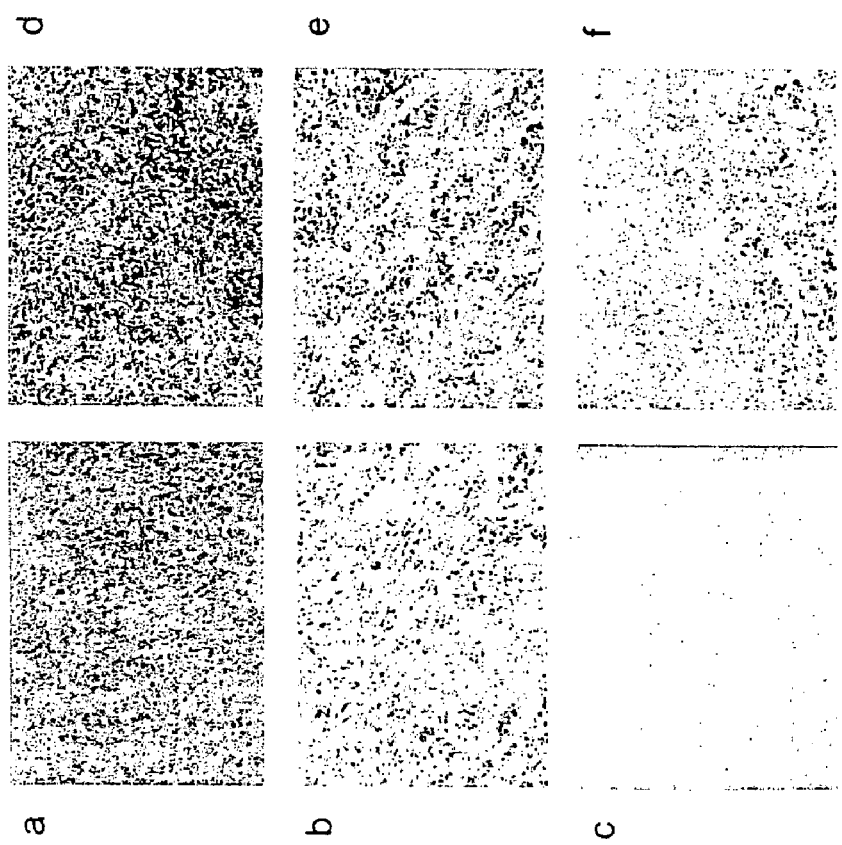
FIGS. 15A-15F are a series of images showing immunoperoxidase staining of paraffin-embedded tumor sections with Klenow FragEL DNA fragmentation Kit for apoptosis. Sections were obtained from mice treated with either unrelated fragmented IgM (FIGS. 15A-15C) or fragmented PAM-1 antibody (FIGS. 15D-15F).

Morphological analysis of the tumors revealed that tumors from mice treated with fragmented PAM-1 antibody exhibited not only a reduced size, but also regressive changes in growth pattern like tumor-regression, infiltration and a high number of pyknotic cells (FIGS. 15A and 15D). In situ staining of the tumors for apoptotic activity showed that the tumors from mice treated with fragmented PAM-1 antibody have a significantly higher number of tumor cells undergoing apoptosis compared to control mice (FIGS. 15C and 15F). FIGS. 15B and 15E show immunoperoxidase staining with an apoptosis-positive control in which all cell nucleic are stained.

EXAMPLE 5

In Vivo Imaging of a Neoplasm

A patient suspected of having a neoplasm, such as stomach cancer, may be given a dose of radioiodinated PAM-1 antibody or fragment thereof, or another tumor-specific polypeptide, and radiolabeled unspecific antibody using the methods described herein. Localization of the tumor for imaging may be effected according to the procedure of Goldenberg et al. (N. Engl. J. Med., 298:1384, 1978). By I.V. an infusion of equal volumes of solutions of $^{131}$I-PAM-1 antibody and Tc-99m-labeled unspecific antibody may be administered to a patient. Prior to administration of the reagents I.V., the patient is typically pre-tested for hypersensitivity to the antibody preparation (unlabeled) or to antibody of the same species as the antibody preparation. To block thyroid uptake of $^{131}$I, Lugol's solution is administered orally, beginning one or more days before injection of the radioiodinated antibody, at a dose of 5 drops twice or three-times daily. Images of various body regions and views may be taken at 4, 8, and 24 hours after injection of the labeled preparations. If present, the neoplasm, e.g., a stomach adenocarcinoma, is detected by gamma camera imaging with subtraction of the Tc-99m counts from those of $^{131}$I, as described for $^{131}$I-labeled anti-CEA antibody and Tc-99m-labeled human serum albumin by DeLand et al. (Cancer Res. 40:3046, 1980). At 8 hours after injection, imaging is usually clear and improves with time up to the 24 hour scans.

EXAMPLE 6

Treatment of a Neoplasm Using Labeled Antibody Mixtures

A patient diagnosed with a neoplasm, for example, a patient diagnosed with a stomach adenocarcinoma, may be treated with PAM-1 antibodies or fragments thereof as follows. Lugol's solution may be administered, e.g., 7 drops 3 times daily, to the patient. Subsequently, a therapeutic dose of $^{131}$I-PAM-1 antibody may be administered to the patient. For example, a $^{131}$I dose of 50 mCi may be given weekly for 3 weeks, and then repeated at intervals adjusted on an individual basis, e.g., every three months, until hematological toxicity interrupts the therapy. The exact treatment regimen is generally determined by the attending physician or person supervising the treatment. The radioiodinated antibodies may be administered as slow I.V. infusions in 50 ml of sterile physiological saline. After the third injection dose, a reduction in the size of the primary tumor and metastases may be noted, particularly after the second therapy cycle, or 10 weeks after onset of therapy.

EXAMPLE 7

Treatment Using Conjugated Antibodies

A patient diagnosed with a neoplasm, for example, a patient with stomach cancer that has metastasized, may be treated with solutions of $^{131}$I-PAM-1, $^{10}$B-PAM-1, and a Tc-99m labeled unspecific antibody. An amount of $^{131}$I-labeled PAM-1 antibody (in 50 ml of sterile physiological saline) sufficient to provide 100 mCi of $^{131}$I activity based on a 70 kg patient weight may be administered to the patient. This dosage is equal to 3.3 mg of an antibody having 40-80 Boron atoms and 8-16 Boron-10 atoms per antibody molecule. The neoplasm is first precisely localized using the procedure of Example 5. In addition, Lugol's solution should be continuously administered to the patient, as in the previous example. A well-collimated beam of thermal neutrons may then be focused on the defined tumor locations. Irradiation with an external neutron beam dose of 400-800 rads, delivered in a period of from 8-20 min, is effected for each tumor locus, and is optionally repeated with administration of the tumor-locating antibody, with or without the radiolabel, at intervals adjusted on an individual basis, but usually not exceeding a total dose of 3200 rads unless simultaneous external irradiation therapy is indicated. If desired, in addition to this therapy, an anti-tumor agent, such as a chemotherapeutic agent, may also be administered to the patient.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

International Patent Application Nos. PCT/IB03/01335 and PCT/IB03/03487, U.S. Pat. Nos. 5,367,060, 5,641,869, 6,207,646, 6,384,018, and all other references cited herein are hereby incorporated by reference.

---

What is claimed is:

1. A method of identifying a candidate therapeutic compound, said method comprising the steps of (a) contacting a cell expressing a polypeptide comprising the amino acid sequence of SEQ ID NO:6, or a fragment thereof comprising amino acids 469-518 of SEQ ID NO:6 or amino acids 739-748 of SEQ ID NO:6, with a test compound, wherein said test compound specifically binds to the polypeptide comprising the sequence of SEQ ID NO:6, or the fragment comprising amino acids 469-518 of SEQ ID NO:6 or amino acids 739-748 of SEQ ID NO:6; and (b) determining whether said test compound induces apoptosis of said cell and not of a control cell contacted with said test compound, wherein a test compound that induces apoptosis of said cell and not of said control cell is a candidate therapeutic compound.

2. The method of claim 1, wherein said fragment comprises amino acids 469-518 of SEQ ID NO:6 and amino acids 739-748 of SEQ ID NO:6.

3. The method of claim 1, wherein said cell is adenocarcinoma cell line 23132 (DSMZ Accession No. DSM ACC 201).

4. The method of claim 2, wherein said fragment comprises a contiguous sequence of SEQ ID NO:6, wherein said contiguous sequence comprises amino acids 469-518 of SEQ ID NO:6 and amino acids 739-748 of SEQ ID NO:6.

5. The method of claim 1, wherein said test compound is an antibody or an antigen-binding fragment.

6. The method of claim 5, wherein said test compound is an antigen-binding fragment.

7. The method of claim 5, wherein said antibody or antibody fragment is a human antibody or a human antigen-binding fragment.

8. The method of claim 1, wherein said cell is a stomach carcinoma cell.

* * * * *

UNITED STATES PATENT AND TRADEMARK OFFICE
CERTIFICATE OF CORRECTION

PATENT NO. : 7,378,247 B2  Page 1 of 1
APPLICATION NO. : 10/764730
DATED : May 27, 2008
INVENTOR(S) : Muller-Hermelink et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 526 days Delete the phrase "by 0 days" and insert -- by 15 days --

Signed and Sealed this

Twentieth Day of January, 2009

JON W. DUDAS
*Director of the United States Patent and Trademark Office*